(12) United States Patent
Batra et al.

(10) Patent No.: US 9,765,047 B2
(45) Date of Patent: Sep. 19, 2017

(54) PROCESS FOR MAKING BERAPROST

(71) Applicant: United Therapeutics Corporation, Silver Spring, MD (US)

(72) Inventors: Hitesh Batra, Herndon, VA (US); Liang Guo, Vienna, VA (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

(21) Appl. No.: 15/234,580

(22) Filed: Aug. 11, 2016

(65) Prior Publication Data

US 2017/0044126 A1   Feb. 16, 2017

Related U.S. Application Data

(60) Provisional application No. 62/204,145, filed on Aug. 12, 2015.

(51) Int. Cl.
  *C07D 307/93*   (2006.01)

(52) U.S. Cl.
  CPC .................. *C07D 307/93* (2013.01)

(58) Field of Classification Search
  None
  See application file for complete search history.

(56) References Cited

U.S. PATENT DOCUMENTS

| | | | |
|---|---|---|---|
| 4,474,802 A | 10/1984 | Ohno et al. | |
| 4,775,692 A | 10/1988 | Ohno et al. | |
| 4,880,939 A | 11/1989 | Ohno et al. | |
| 5,202,447 A | 4/1993 | Ohno et al. | |
| 7,345,181 B2 | 3/2008 | Kim et al. | |
| 8,779,170 B2 | 7/2014 | Sharma et al. | |
| 9,181,212 B2 | 11/2015 | Sharma et al. | |
| 9,334,255 B2 | 5/2016 | Sharma et al. | |
| 9,388,154 B2 * | 7/2016 | Yiannikouros | C07D 307/93 |
| 2012/0323025 A1 | 12/2012 | Sharma et al. | |
| 2016/0244422 A1 | 8/2016 | Sharma et al. | |

FOREIGN PATENT DOCUMENTS

| | | |
|---|---|---|
| WO | WO 2012/174407 A1 | 12/2012 |
| WO | WO 2013/040068 A2 | 3/2013 |
| WO | WO 2015/179427 A1 | 11/2015 |

OTHER PUBLICATIONS

Das et al., "Recent Developments in the Synthesis of Prostaglandins and Analogues," Chem. Rev., 2007, 107:3286-3337.

Nagase et al., "Synthesis of (+)-5,6,7-trinor-4,8-inter-m-phenylene $PGI_2^{1)}$," Tetrahedron Letters, 1990, 31(31):4493-4494.

* cited by examiner

*Primary Examiner* — Timothy R Rozof

(74) *Attorney, Agent, or Firm* — Foley & Lardner LLP

(57) ABSTRACT

A method is described for making single isomers of synthetic beraprost diol, a key intermediate for making 314-d isomer of beraprost. The method requires fewer steps than the known methods for making these compounds and can be used to scale up the reaction more easily to produce commercial quantities.

33 Claims, 18 Drawing Sheets

| | NAME | RT | RT RATIO | AREA | % AREA |
|---|---|---|---|---|---|
| 11 | | 2.695 | | 481 | 0.00 |
| 12 | | 2.994 | | 104376 | 1.07 |
| 13 | | 3.709 | | 1753 | 0.02 |
| 14 | | 3.980 | | 7424 | 0.08 |
| 15 | | 4.506 | | 21390 | 0.22 |
| 16 | CYCLIZED ACETATE | 4.694 | | 145685 | 1.49 |
| 17 | E/Z ISOMER | 5.331 | | 2011715 | 20.53 |
| 18 | E/Z ISOMER ISOMERIZED ACETATE | 5.762 | | 7285735 | 74.34 |
| 19 | | 6.255 | | 70069 | 0.71 |
| 20 | | 7.067 | | 22444 | 0.23 |
| 21 | | 7.685 | | 58191 | 0.59 |
| 22 | | 8.648 | | 2315 | 0.02 |
| 23 | | 8.903 | | 23640 | 0.24 |
| 24 | | 9.090 | | 7751 | 0.08 |
| 25 | | 9.240 | | 3040 | 0.03 |
| 26 | | 9.461 | | 2566 | 0.03 |
| 27 | | 9.687 | | 7102 | 0.07 |

PROCESS FOR MAKING BERAPROST

CROSS-REFERENCE TO RELATED APPLICATIONS

This application claims priority from U.S. Provisional Application No. 62/204,145, filed Aug. 12, 2015, the entire contents of which are incorporated by reference in their entirety.

FIELD OF THE INVENTION

The present application relates to a process for selectively producing single-isomer benzoprostacyclin derivatives, including beraprost and its derivatives.

BACKGROUND OF THE INVENTION

Prostacyclin derivatives are useful pharmaceutical compounds and possess activities such as platelet aggregation inhibition, gastric secretion reduction, lesion inhibition, and bronchodilation.

Beraprost is a synthetic benzoprostacyclin analogue of natural prostacyclin that is currently under clinical trials for the treatment of pulmonary hypertension and vascular disease (excluding renal disease) in North America and Europe.

Beraprost and related benzoprostacyclin analogues of the formula (I), as defined below, are disclosed, for example, in U.S. Pat. No. 5,202,447 and Tetrahedron Lett. 31, 4493 (1990).

Furthermore, as described in U.S. Pat. No. 7,345,181, several synthetic methods are known to produce benzoprostacyclin analogues.

Known synthetic methods generally require one or more resolutions of intermediates to obtain a pharmacologically active isomer of beraprost, such as beraprost 314-d, or a related benzoprostacyclin analogue. Also, current pharmaceutical formulations of beraprost or a related benzoprostacyclin analogue may consist of several isomers of the pharmaceutical compound, and only one of which is primarily responsible for the pharmacologic activity of the drug.

Isolation of isomers of beraprost compounds from current synthetic methods requires multiple preparative HPLC or chromatographic purification procedures or multiple recrystallizations, which are not preferable or feasible on a commercially applicable scale. Therefore, it is desired to achieve an efficient, commercially applicable synthetic route to the isomers of beraprost or a related benzoprostacyclin analogue.

SUMMARY OF THE INVENTION

In some embodiments, the present invention provides a process for preparing a compound of the following formula:

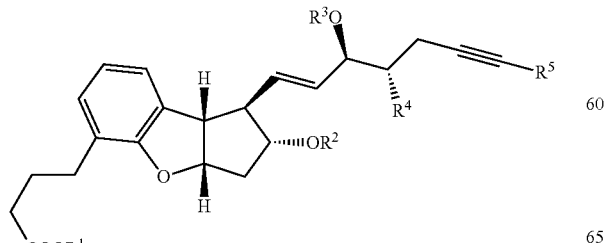

(I)

wherein $R^1$ represents a cation, H, or $C_{1-12}$ alkyl, $R^2$ and $R^3$ each represent H or a hydroxy protective group $R^4$ represents H or $C_{1-3}$ alkyl, and $R^5$ represents H or $C_{1-6}$ alkyl, comprising:

(1) reacting a compound of the following formula:

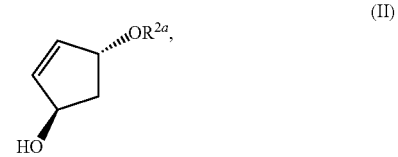

(II)

wherein $R^{2a}$ is H or an hydroxy protective group with a compound of the following formula:

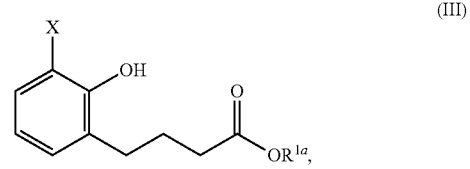

(III)

wherein $R^{1a}$ is a cation, H, or $C_{1-12}$ alkyl, X is halogen to form a compound of the following formula:

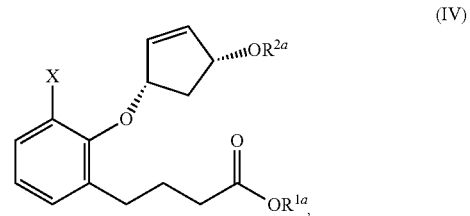

(IV)

wherein $R^{1a}$, $R^{2a}$ and X are each defined above;

(2) cyclizing a compound of formula (IV) to form a compound of the following formula:

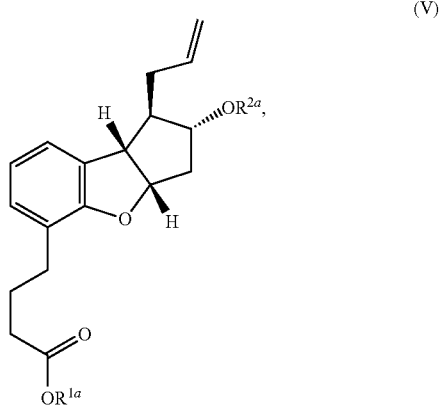

(V)

wherein $R^{1a}$ and $R^{2a}$ are each defined above;

(3) isomerizing an allyl of the compound of formula (V) to form a propenyl resulting in a compound of the following formula:

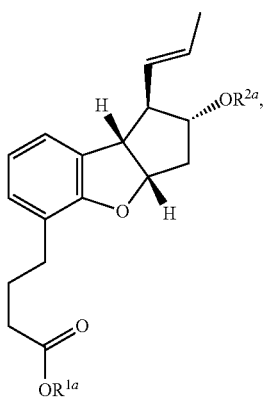

(VI)

wherein $R^{1a}$ and $R^{2a}$ are each defined above;

(4) ozonolysis and in situ reduction to convert the propenyl of the compound of formula (VI) to an alcohol resulting in a compound of the following formula:

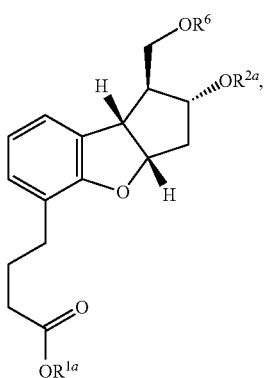

(VII)

wherein $R^{1a}$ and $R^{2a}$ are each defined above, $R^6$ is H or a hydroxy protective group;

(5) deprotecting an acetate of the compound of formula (VII) to form a compound of the following formula:

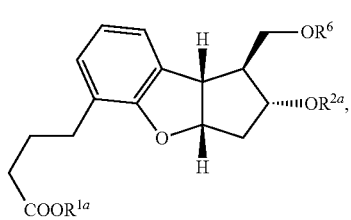

(VIII)

wherein $R^{1a}$, $R^{2a}$ and $R^6$ are each defined above;

(6) selectively deprotecting the primary hydroxy protective group, followed by oxidation of the primary hydroxy group to form an aldehyde, followed by coupling with a side-chain of the formula:

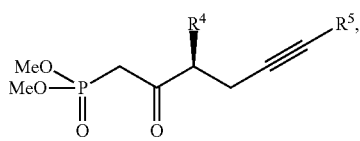

(IX)

wherein $R^4$ and $R^5$ are each defined above, to form a compound of the following formula:

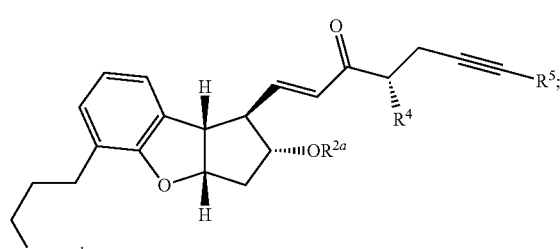

(X)

(7) reduction of the ketone, deprotection of any remaining hydroxy protective group and optionally converting the $R^{1a}$ into a cation or H to form a compound of the following formula:

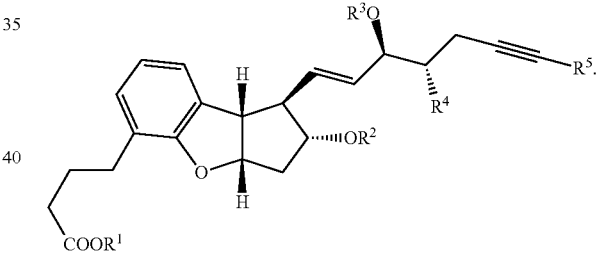

(I)

In some embodiments, the present invention provides a method that produces the compound of formula (I) as a substantially pure single isomer.

In some embodiments, $R^2$, $R^3$, $R^{2a}$ and $R^6$ each independently represent an acetate, a silyl ester (for example trimethylsilyl, triethylsilyl, t-butyldimethylsilyl, t-butyldiphenylsilyl, phenyldimethylsilyl, tetrahydropyranyl), benzoate ester, benzyl or substituted benzyl.

In some embodiments, $R^{1a}$ is $CH_3$ and $R^{2a}$ and $R^6$ are both H. In some embodiments, X is bromo, iodo, or chloro.

In some embodiments, azobisisobutyronitrile is used as a radical initiator in step (2).

In some embodiments, a catalytic amount of carbonylchlorohydridotris(triphenylphosphine) ruthenium (II) is used in step (3).

In some embodiments, step (4) produces an in situ trapped aldehyde intermediate represented by the compound of formula (XI)

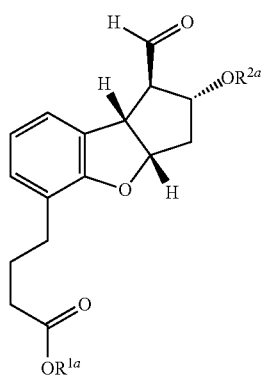
(XI)

wherein $R^{1a}$ and $R^{2a}$ is each defined above.

In some embodiments, sulfuric acid is used in step (5).

In another aspect, the present invention also provides a process for preparing a compound of the following formula:

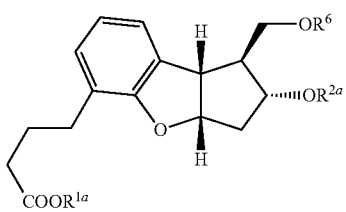
(VIII)

wherein $R^{1a}$ represents a cation, H, or $C_{1\text{-}12}$ alkyl and $R^{2a}$ and $R^6$ each represent H, a hydroxyl protective group, an acetate protective group, a silyl ether, benzoate ester, benzyl, or substituted benzyl comprising:

(1) performing a Mitsunobu reaction on the compound of the following formula:

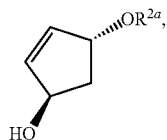
(II)

wherein $R^{2a}$ is defined above,
with a compound of the following formula:

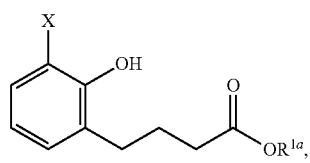
(III)

wherein $R^{1a}$ is defined above, X is halogen to form a compound of the following formula:

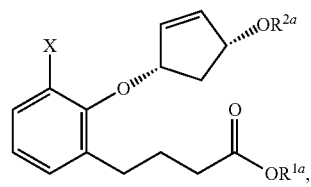
(IV)

wherein $R^{1a}$, $R^{2a}$ and X is each defined above;

(2) radical cyclization of formula (IV) to form a compound of the following formula:

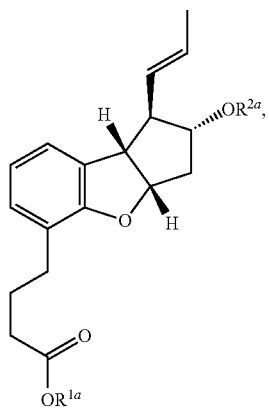
(V)

wherein $R^{1a}$ and $R^{2a}$ is each defined above;

(3) isomerizing the allyl of the compound of formula (V) to form a propenyl resulting in a compound of the following formula:

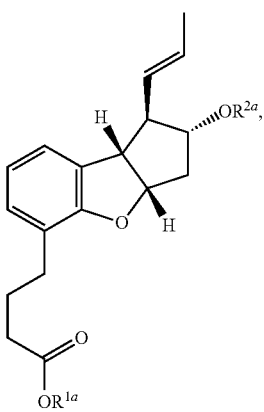
(VI)

wherein $R^{1a}$ and $R^{2a}$ is each defined above;

(4) ozonolysis and in situ reduction to convert the propenyl of the compound of formula (VI) to form an alcohol resulting in a compound of the following formula:

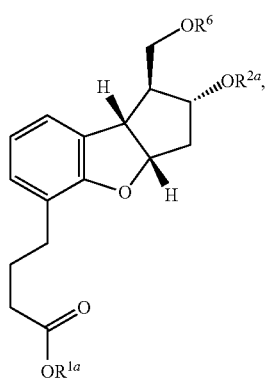

(VII)

wherein $R^{1a}$, $R^{2a}$ and $R^6$ are each defined above;

(5) deprotection of the acetate of the compound of formula (VII) to form a compound of the following formula:

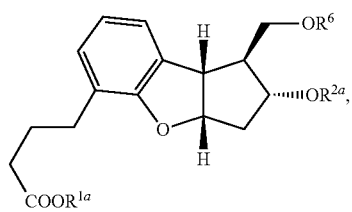

(VIII)

wherein $R^{1a}$, $R^{2a}$ and $R^6$ is each defined above.

In some embodiments, the compound of formula (VIII) is produced as a substantially pure single isomer.

In some embodiments, $R^{2a}$ and $R^6$ each independently represent an acetate, a silyl ester (for example, trimethylsilyl, triethylsilyl, t-butyldimethylsilyl, t-butyldiphenylsilyl, phenyldimethylsilyl, tetrahydropyranyl), benzoate ester, benzyl or substituted benzyl.

In some embodiments, $R^{1a}$ is $CH_3$, and $R^{2a}$ and $R^6$ are both H. In some embodiment, X is chloro, bromo or iodo.

In some embodiments, azobisisobutyronitrile is used in step (2) as a radical initiator.

In some embodiments, a catalytic amount of carbonylchlorohydridotris(triphenylphosphine) ruthenium (II) is used in step (3).

In some embodiments, sulfuric acid is used in step (5).

In some embodiments, the present invention provides a method that can produce a compound of formula (I), as defined below, in a substantially isomerically pure form. In some embodiments, the present invention provides a method for preparing a compound of formula (I) in fewer steps than the prior art. In a preferred embodiment, the present invention provides a method for preparing a compound of formula (I) in commercially useful quantities. In another preferred embodiment, the present invention provides a method that can produce the beraprost diol intermediates represented by formula (VIII), as defined below, in a substantially isomerically pure form, which can be used for the production of pharmaceutical compounds represented by the general formula (I) or other similar compounds. In yet another preferred embodiment, the present invention provides a method comprising a key radical cyclization step for the synthesis of tricyclic beraprost and its derivatives on a larger scale, preferably more than about 2 grams, more preferably more than about 10 grams. In other embodiments, the invention relates to any of the compounds in the reaction schemes depicted herein in a more pure form compared to those obtained by presently known methods, including an isomerically more pure form.

In some embodiments, the synthesis of beraprost diol (7) is carried out in five steps. The first step of the synthesis comprises the coupling of (1R,4R)-4-hydroxycyclopent-2-en-1-yl acetate and 2-bromophenol-6-carbomethoxypropane using a Mitsunobu reaction to obtain bromophenyl acetoxycyclopentenyl ether (3) with a yield of about 89.5%. The second step comprises radical cyclization and in situ radical trapping by reacting with allyltributyltin using azobisisobutyronitrile as a radical initiator. This step permits the formation of a tricyclic core in a stereochemical fashion. The stereochemistry is governed by the stereochemistry of the coupled compound bromophenyl acetoxycyclopentenyl ether (3) at the ether linkage and acetate group, as shown by the chiral purity of beraprost diol (99.9% by HPLC). In some embodiments, the isolated yield for this step is 65.5%. The fourth step comprises isomerizing the allyl group of allyl acetoxycyclopentabenzofuran (4) to propenyl group by using catalytic amount of carbonylchlorohydridotris(triphenylphosphine)ruthenium (II) to obtain alkenyl acetoxycyclopentabenzofuran (5) in 92.6% yield. The propenyl group of alkenyl acetoxycyclopentabenzofuran (5) is converted into alcohol functionality by the process of ozonolysis and in situ reduction using sodium borohydride, which provides hydroxy acetoxycyclopentabenzofuran (6) in 85.5% yield (over two steps). The last step involves deprotecting the acetate group using concentrated sulfuric acid to obtain beraprost diol (7), which is crystallized from MTBE in 80% yield. In some embodiments, the yield may be greater than 80%, greater than 85%, greater than 90%, or greater than 95%. In a preferred embodiment, the overall yield of this process over 5 steps is 37%, or greater than 37% with a chiral purity of 99.9% or more by HPLC. In some embodiments, the overall yield is greater than 40%, greater than 45%, or greater than 50%.

In some embodiments, a method of producing beraprost diol comprises the steps shown below.

Scheme 1: Synthesis of Chiral Beraprost Diol by Radical Cyclization

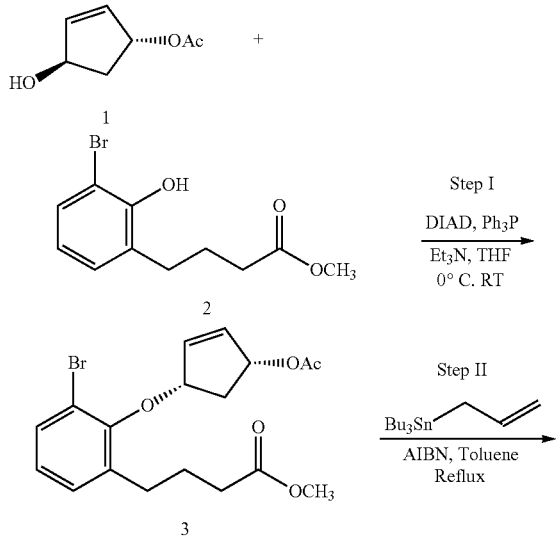

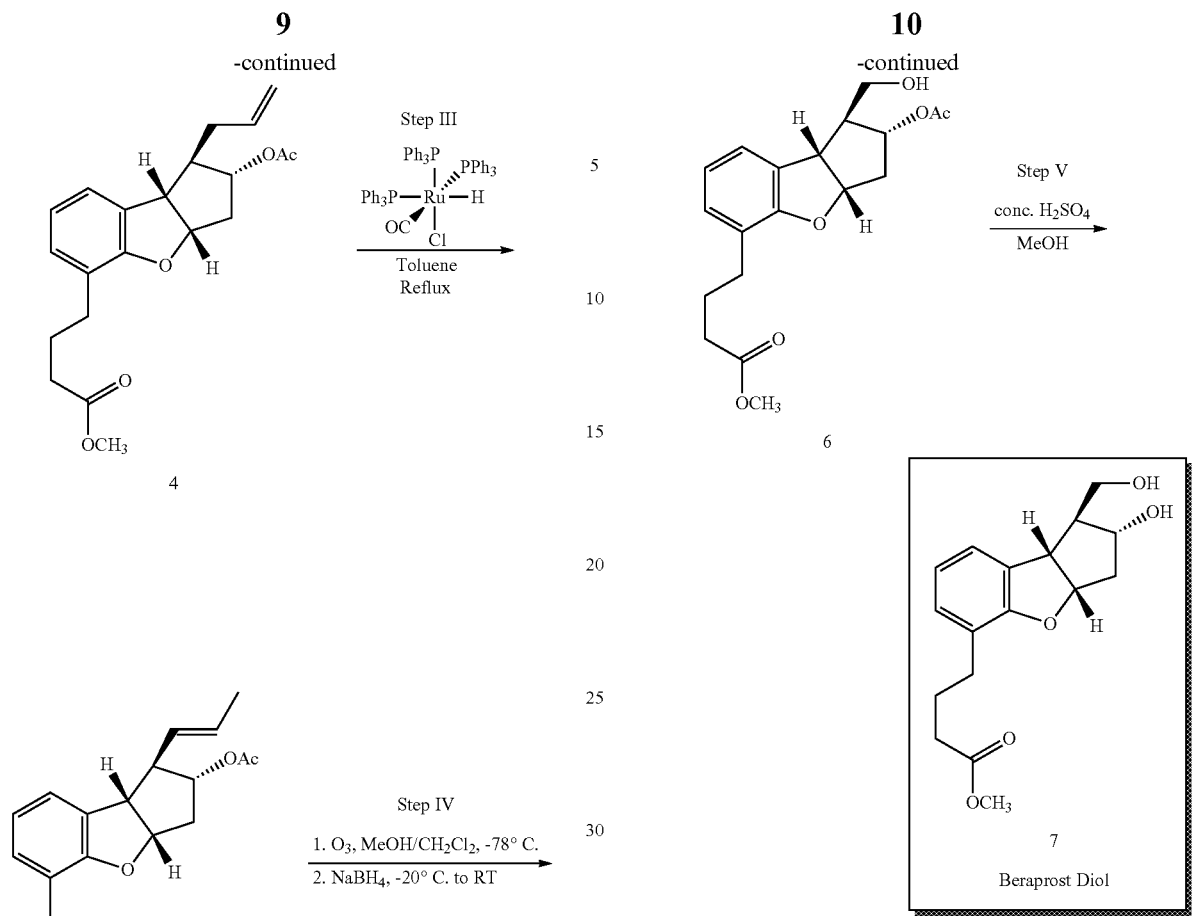

In some embodiments, the methods described herein are advantageous over the previous methods for making beraprost or its derivatives as it directly produces the optically active diol, and thus does not require separating the desired isomer from a racemic mixture. In addition, in some embodiments, the methods described herein can be used to synthesize beraprost in only seven or eight steps, which is the shortest chiral route to obtain the beraprost 314d isomer as well as its derivatives.

In some embodiments, the synthesis of beraprost is carried out according to the following scheme.

Scheme 2: Synthesis of Beraprost

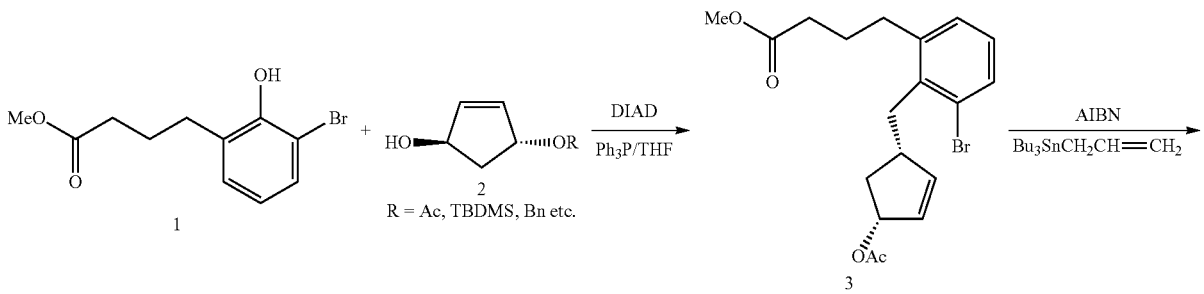

11

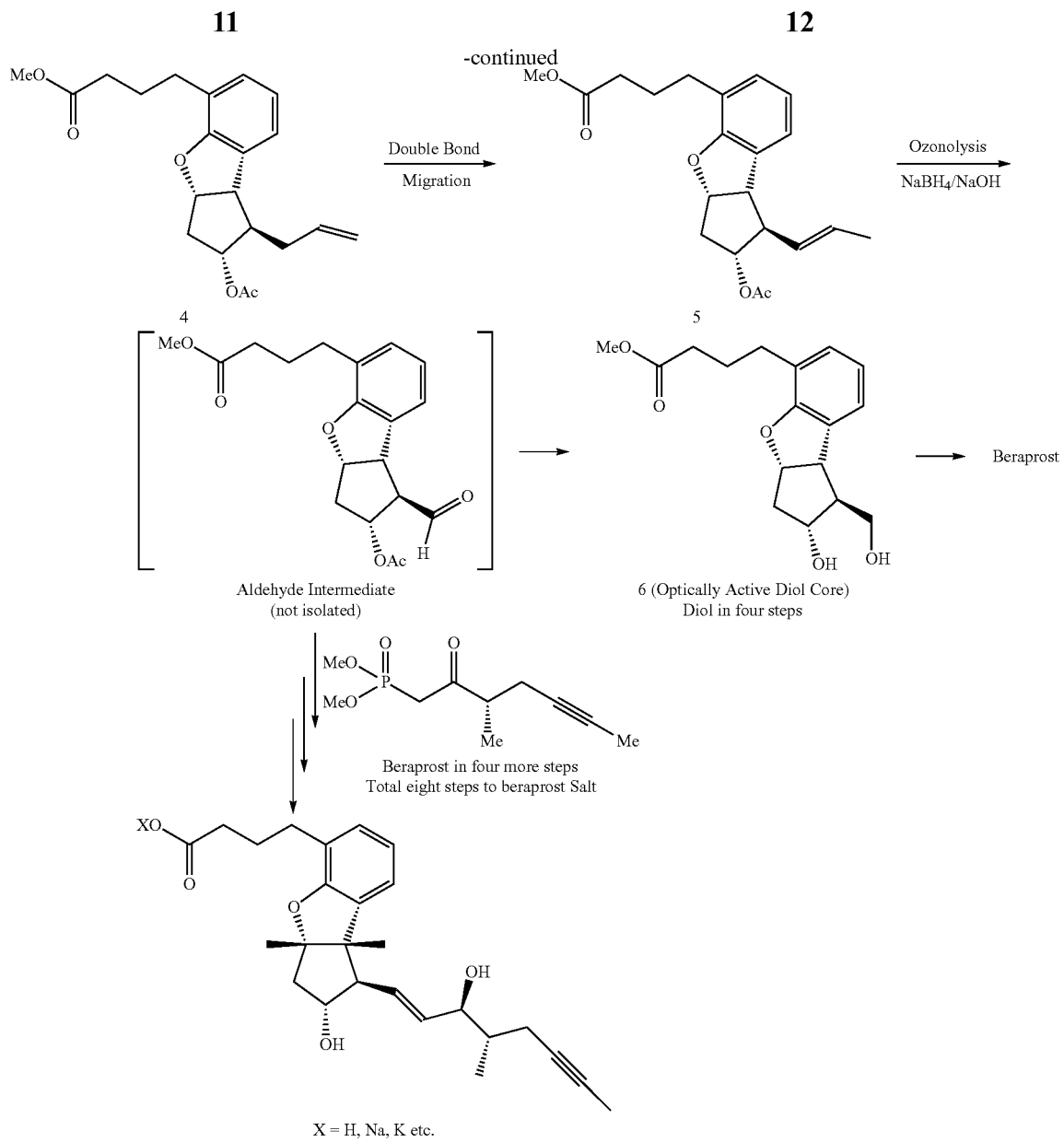

In some embodiments, the present invention provides a process for preparing a compound of the following formula:

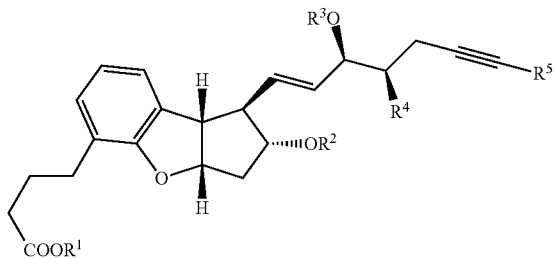

wherein $R^1$ represents a cation, H, or $C_{1-12}$ alkyl,
$R^2$ and $R^3$ each represent H or a hydroxy protective group,
$R^4$ represents H or $C_{1-3}$ alkyl, and
$R^5$ represents H or $C_{1-6}$ alkyl, comprising:
(1) reacting a compound of the following formula:

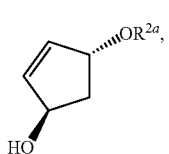

wherein $R^{2a}$ is H or an hydroxy protective group, with a compound of the following formula:

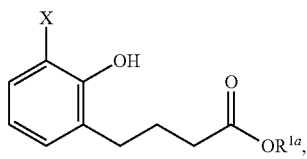 (III)

wherein $R^{1a}$ is a cation, H, or $C_{1-12}$ alkyl, X is a halogen selected from chloro, bromo and iodo,
to form a compound of the following formula:

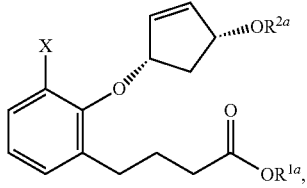 (IV)

wherein $R^{1a}$, $R^{2a}$ and X are each defined above;
(2) cyclizing a compound of formula (IV) to form a compound of the following formula:

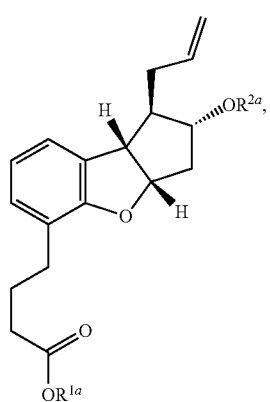 (V)

wherein $R^{1a}$ and $R^{2a}$ are each defined above;
(3) isomerizing an allyl of the compound of formula (V) to form a propenyl resulting in a compound of the following formula:

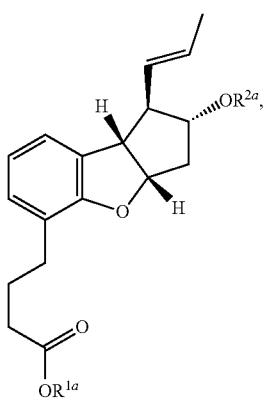 (VI)

wherein $R^{1a}$ and $R^{2a}$ are each defined above;

(4) ozonolysis and in situ reduction to convert the propenyl of the compound of formula (VI) to form an alcohol resulting in a compound of the following formula:

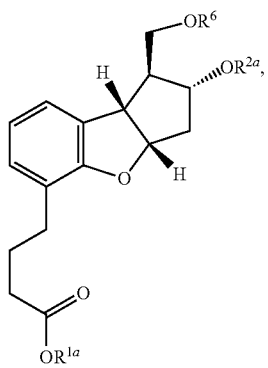 (VII)

wherein $R^{1a}$ and $R^{2a}$ are each defined above, $R^6$ is H or a hydroxy protective group;
(5) deprotecting an acetate of the compound of formula (VII) to form a compound of the following formula:

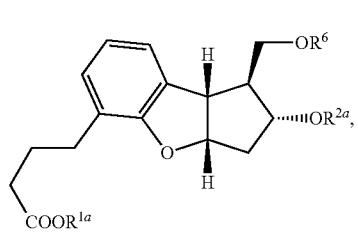 (VIII)

wherein $R^{1a}$, $R^{2a}$ and $R^6$ are each defined above;
(6) selectively deprotecting the primary hydroxy protective group, followed by oxidation of the primary hydroxy group to form an aldehyde, followed by coupling with a side-chain of the formula:

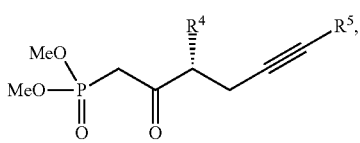 (XIII)

wherein $R^4$ and $R^1$ are each defined above to form a compound of the following formula:

(XIV)

(7) reduction of the ketone, deprotection of any remaining hydroxy protective group and optionally converting the $R^{1a}$ into a cation or H to form a compound of the following formula:

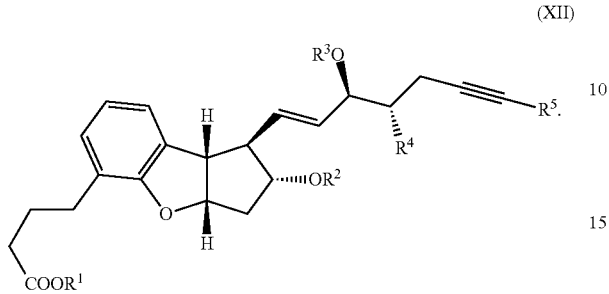

(XII)

In some embodiments, the present invention provides a method that produces the compound of formula (XII) as a substantially pure single isomer.

In some embodiments, $R^2$, $R^3$, $R^{2a}$ and $R^6$ each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl.

In some embodiments, $R^{1a}$ is $CH_3$ and $R^{2a}$ and $R^6$ are both H.

In some embodiments, azobisisobutyronitrile is used as a radical initiator in step (2).

In some embodiments, a catalytic amount of carbonylchlorohydridotris(triphenylphosphine) ruthenium (II) is used in step (3).

In some embodiments, sulfuric acid is used in step (5).

In some embodiments, the present invention provides a process for preparing a compound of the following formula:

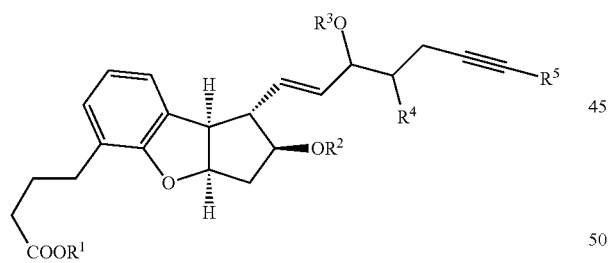

(XV)

wherein $R^1$ represents a cation, H, or $C_{1-12}$ alkyl,
$R^2$ and $R^3$ each represent H or a hydroxy protective group,
$R^4$ represents H or $C_{1-3}$ alkyl, and
$R^5$ represents H or $C_{1-6}$ alkyl, comprising:
(1) reacting a compound of the following formula:

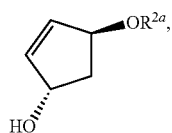

(XVI)

wherein $R^{2a}$ is H or an hydroxy protective group, with a compound of the following formula:

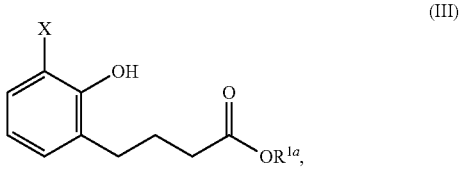

(III)

wherein $R^{1a}$ is a cation, H, or $C_{1-12}$ alkyl, X is a halogen selected from chloro, bromo and iodo,
to form a compound of the following formula:

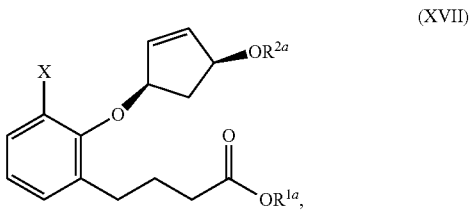

(XVII)

wherein $R^{1a}$, $R^{2a}$ and X are each defined above;
(2) cyclizing a compound of formula (XVII) to form a compound of the following formula:

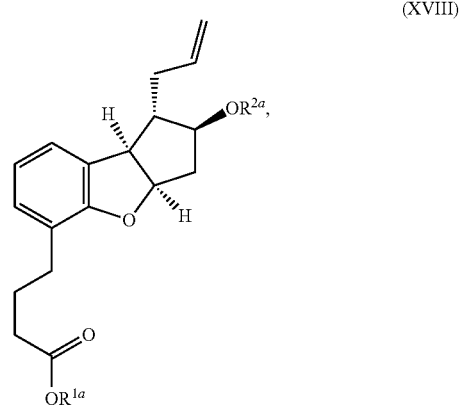

(XVIII)

wherein $R^{1a}$ and $R^{2a}$ are each defined above;
(3) isomerizing an allyl of the compound of formula (XVIII) to form a propenyl resulting in a compound of the following formula:

(XIX)

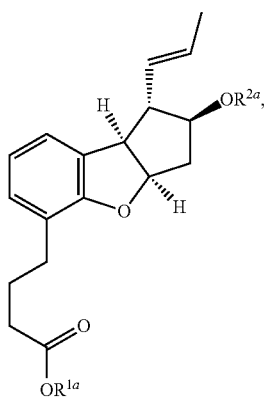

wherein $R^{1a}$ and $R^{2a}$ are each defined above;

(4) ozonolysis and in situ reduction to convert the propenyl of the compound of formula (XIX) to form an alcohol resulting in a compound of the following formula:

(XX)

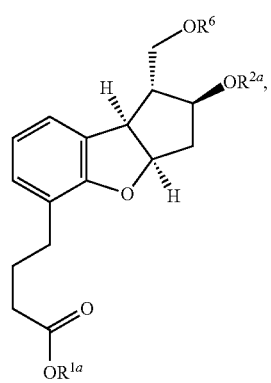

wherein $R^{1a}$ and $R^{2a}$ are each defined above, $R^6$ is H or a hydroxy protective group;

(5) deprotecting an acetate of the compound of formula (XX) to form a compound of the following formula:

(XXI)

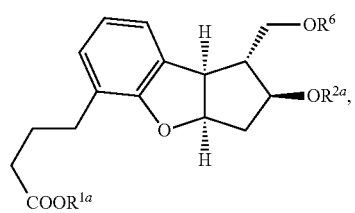

wherein $R^{1a}$, $R^{2a}$ and $R^6$ are each defined above;

(6) selectively deprotecting the primary hydroxy protective group, followed by oxidation of the primary hydroxy group to form an aldehyde, followed by coupling with a side-chain of the formula:

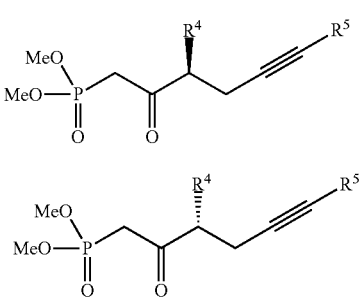

wherein $R^4$ and $R^5$ are each defined above to form a compound of the following formula:

(XXIII)

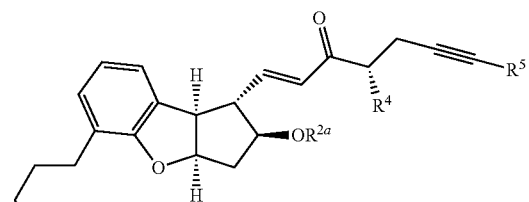

or (XXIV)

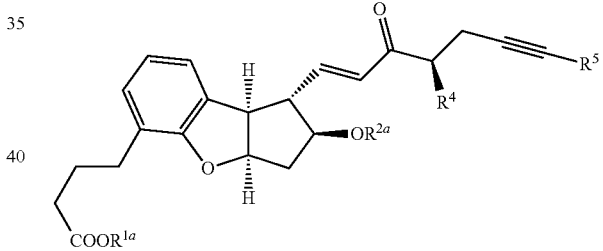

(7) reduction of the ketone, deprotection of any remaining hydroxy protective group and optionally converting the $R^{1a}$ into a cation or H to form a compound of the following formula:

(XV)

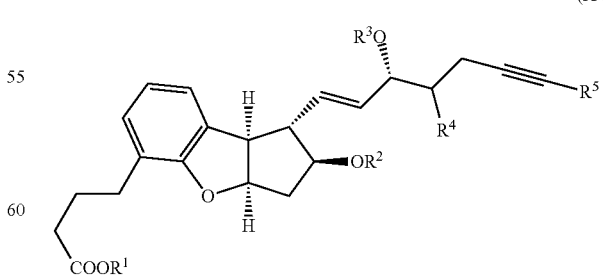

In some embodiments, the present invention provides a method that produces the compound of formula (XV) as a substantially pure single isomer of the formula

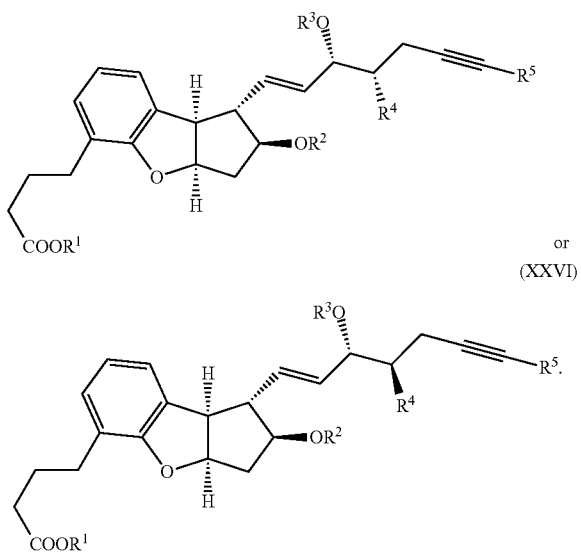

(XXV)

or (XXVI)

In some embodiments, $R^2$, $R^3$, $R^{2a}$ and $R^6$ each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl.

In some embodiments, $R^{1a}$ is $CH_3$ and $R^{2a}$ and $R^6$ are both H.

In some embodiments, azobisisobutyronitrile is used as a radical initiator in step (2).

In some embodiments, a catalytic amount of carbonylchlorohydridotris(triphenylphosphine) ruthenium (II) is used in step (3).

In some embodiments, sulfuric acid is used in step (5).

In some embodiments, the present invention provides a process for preparing four single isomers of the formula (I), (XII), (XXV) and (XXVI). In some embodiment, a method of producing the four isomers comprises the steps shown below.

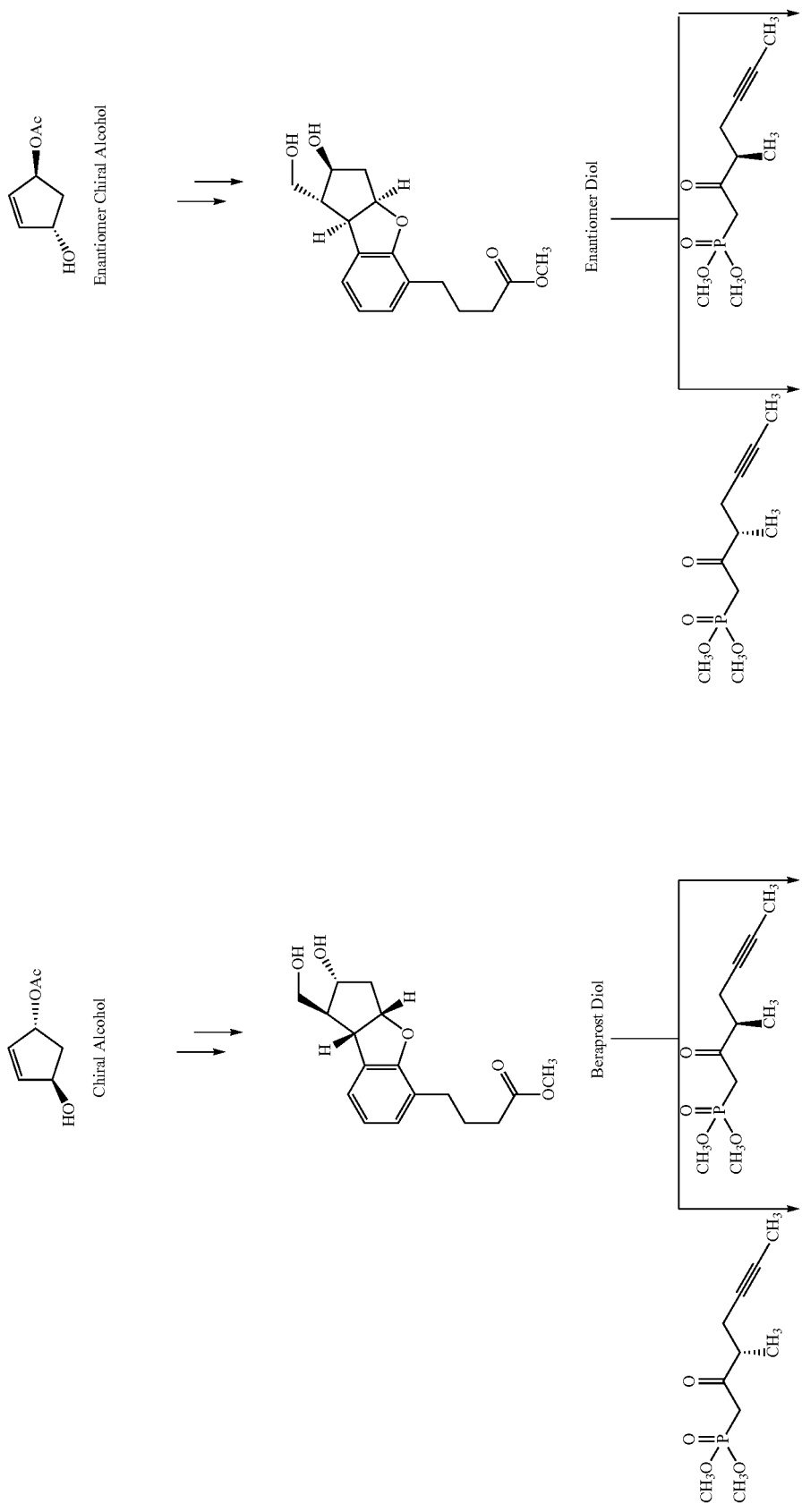
Scheme 3. Synthesis of Four Isomers of Esuberaprost

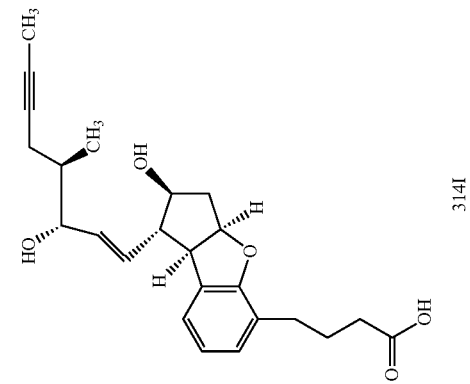
314I
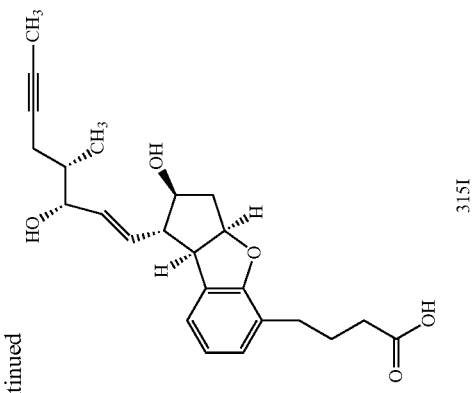
315I
-continued
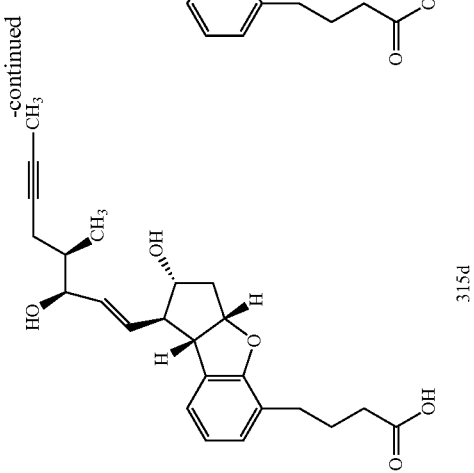
315d
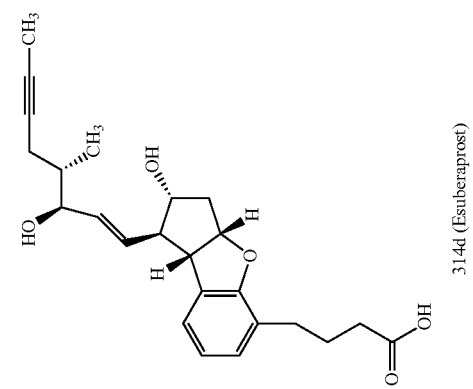
314d (Esuberaprost)

In some embodiments, the present invention provides a process for preparing a compound of the following formula:

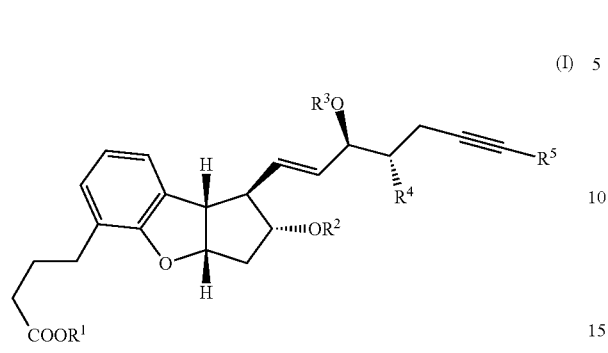
(I)

wherein $R^1$ represents a cation, H, or $C_{1-12}$ alkyl,
$R^2$ and $R^3$ each represent H or a hydroxy protective group,
$R^4$ represents H or $C_{1-3}$ alkyl, and
$R^5$ represents H or $C_{1-6}$ alkyl, comprising:
(1) protecting a hydroxyl group of a compound of the following formula:

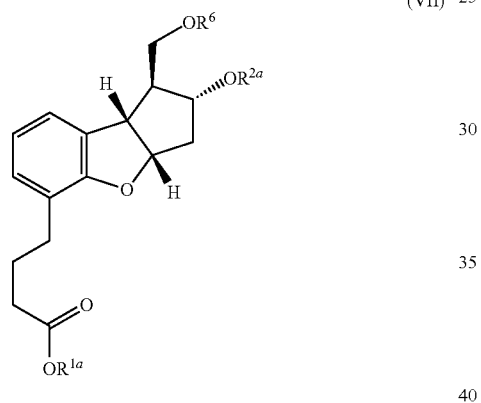
(VII)

wherein $R^{1a}$ is a cation, H, or $C_{1-12}$ alkyl; $R^{2a}$ and $R^6$ are each H or a hydroxy protective group, to produce a compound of the following formula:

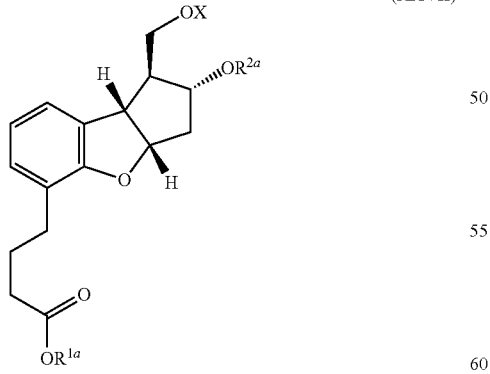
(XXVII)

wherein X is a trityl protecting group, tertiary butyldimethyl silyl (TBDMS), triethyl silyl (TES), methoxy methane (MOM), tertiary butyldiphenyl silyl (TBDPS), acetate, benzoate, or benzyl;
(2) protecting a hydroxyl group of the compound of (XXVII) to form a compound of the following formula:

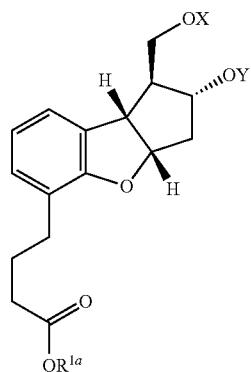
(XXVIII)

wherein Y is tertiary butyldimethyl silyl (TBDMS) group, triethyl silyl (TES), methoxy methane (MOM), tertiary butyldiphenyl silyl (TBDPS), acetate, benzoate, or benzyl;
(3) deprotection one of the hydroxyl protective groups to form a compound of the following formula:

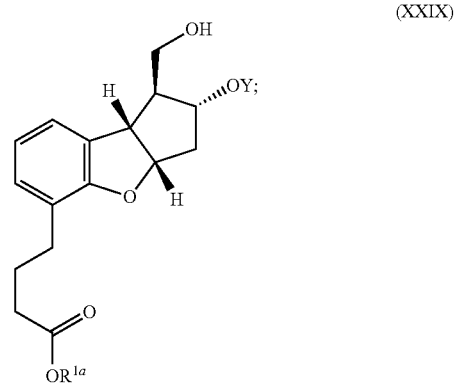
(XXIX)

(4) oxidation of a hydroxyl group of the compound to form a compound of the following formula:

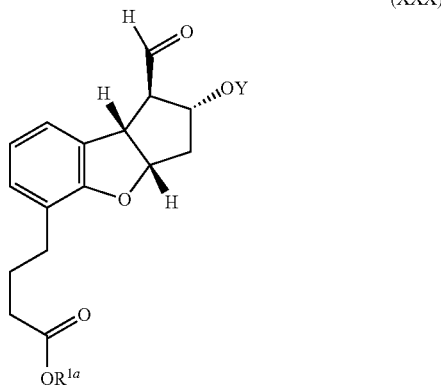
(XXX)

(5) Reacting with stannanes to form a compound of the following formula:

to form a compound of the following formula:

(XXXI)

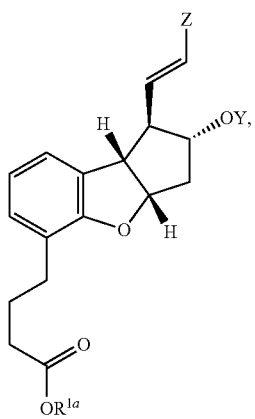

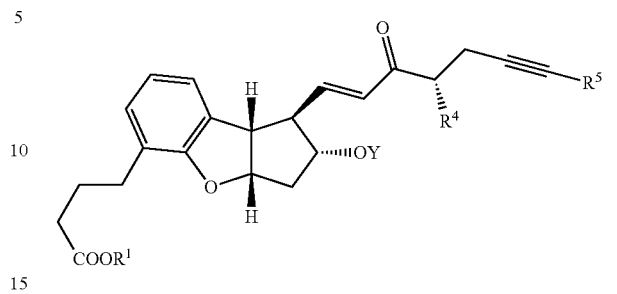

wherein $R^1$, $R^2$, $R^4$ and $R^5$ are each defined above, (7) deprotecting the protective group Y and reducing the ketone of the compound of the formula (XXXIII) to form a compound of the following formula:

wherein Z is tributyl tin (SnBu3);

(6) coupling with a compound of the following formula:

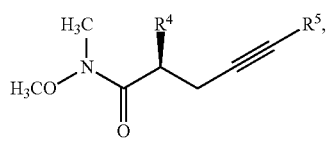

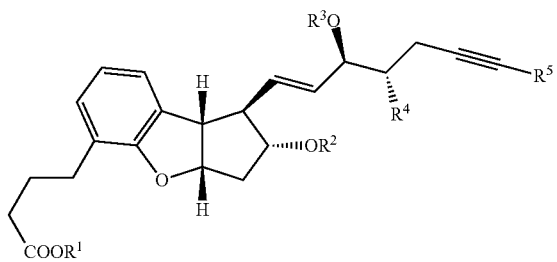

In some embodiments, the methods described herein produce the compound of formula (I) as a substantially pure single isomer.

In some embodiments, a method of producing a compound of formula (I) comprises the steps shown below.

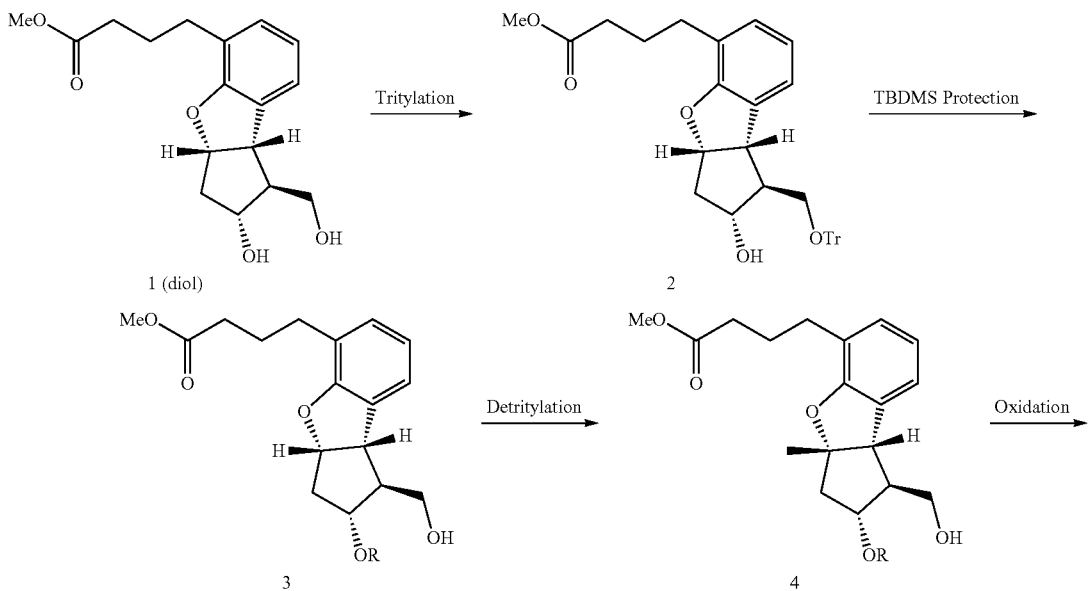

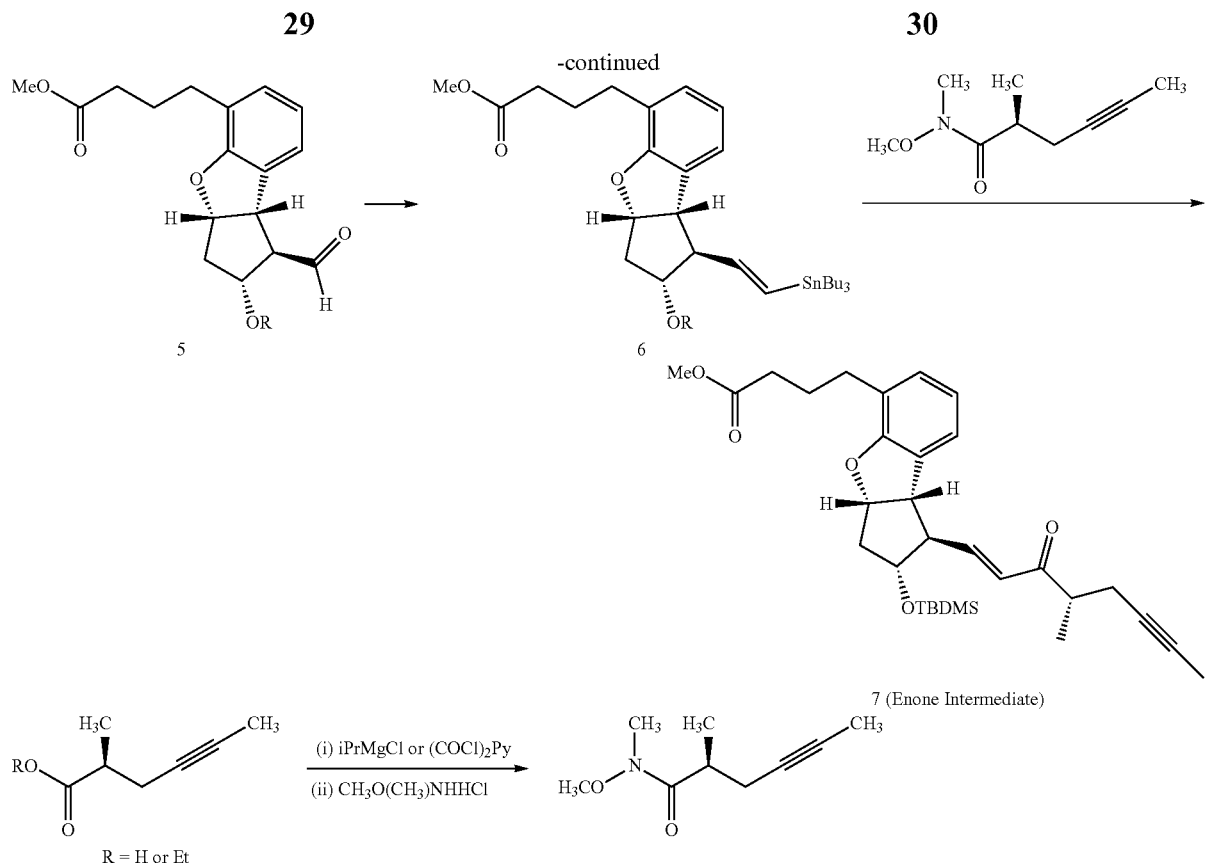

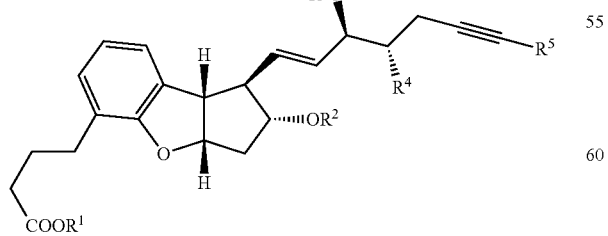

In some embodiment, the methods described herein can be used to prepare a compound of formula (I) without the formation of keto-phosphonate side chain from Weinreb amide, and thus avoids the use of butyl lithium which is a strong base. Under strong basic conditions, the methyl group on the keto-phosphate side chain can racemize and hence lose the optical purity (chiral purity). In contrast, the methods described herein use Weinreb amide, which not only reduces the step of conversion to phosphate but also avoids the problem of racemization and reduces impurities in the subsequent steps. Therefore, in some embodiments, the methods described herein provide the advantage of easily obtaining a desired single isomer of esuberaprost with high chiral impurity.

In some embodiments, the a process for preparing a compound of the following formula:

(I)

[structure with R³O, R⁴, R⁵, OR², COOR¹]

wherein R¹ represents a cation, H, or $C_{1\text{-}12}$ alkyl, R² and R³ each represent H or a hydroxy protective group, R⁴ represents H or $C_{1\text{-}3}$ alkyl, and R⁵ represents H or $C_{1\text{-}6}$ alkyl, comprises:

(1) reacting a compound of the following formula:

(XXXIV)

[structure with R¹OOC, OR²]

with a compound of the following formula:

(XXXV)

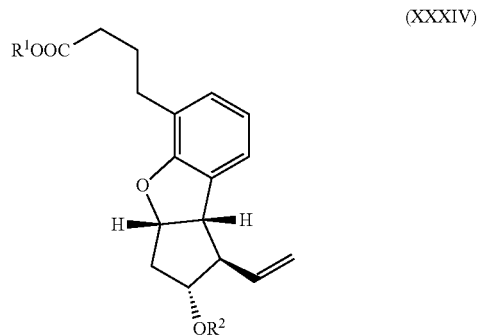

in a Grubbs II metathesis reaction, and (2) base hydrolysis to produce the compound of formula (I).

In some embodiments, the present invention provides a method that produces the compound of formula (I) as a substantially pure single isomer.

In some embodiments, a method of producing a compound of formula (I) comprises the steps shown below.

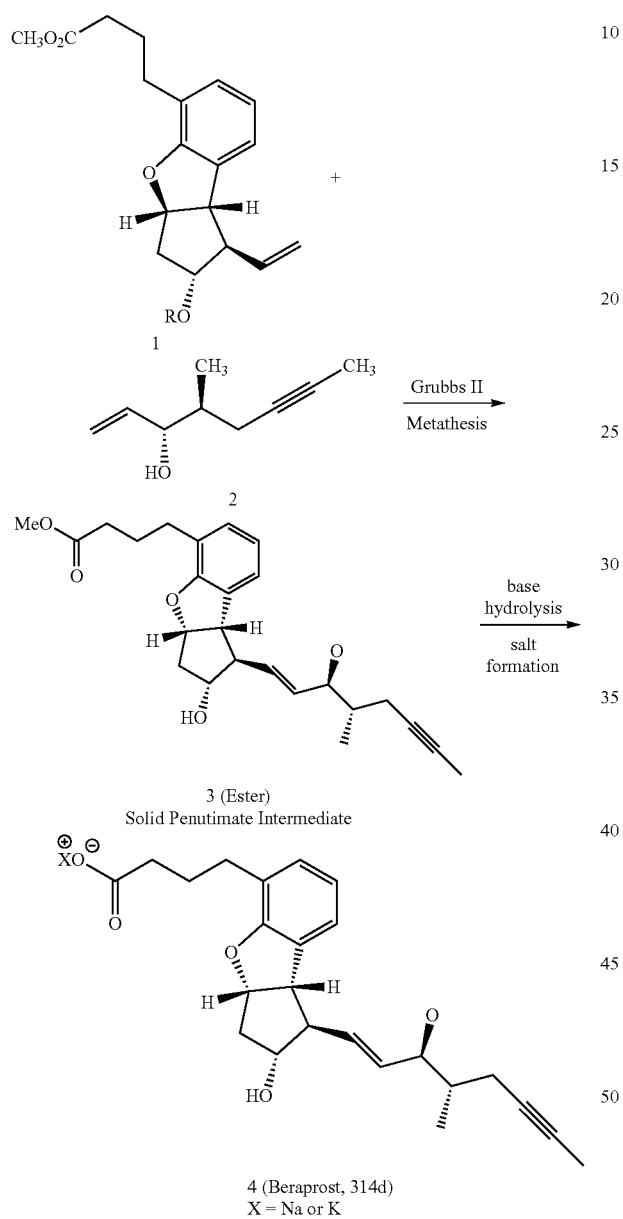

FIGS. 9a and 9b show HPLC profile of compound (6).
FIG. 10 shows $^1$H NMR spectrum of compound (7).
FIG. 11 shows HPLC profile of crude sample of compound (7).
FIG. 12 shows HPLC profile of compound (7).
FIG. 13 shows HPLC profile of compound (7) spiked with reference.
FIG. 14 shows HPLC profile of compound (7) spiked with racemic diol.
FIG. 15 shows $^{13}$C NMR spectrum of compound (7).
FIG. 16 shows mass spectrum of compound (7).

DETAILED DESCRIPTION OF THE PREFERRED EMBODIMENTS

Unless otherwise specified, "a" or "an" means "one or more." In one embodiment, a method for making a substantially pure isomer of beraprost or its related derivatives of following formula:

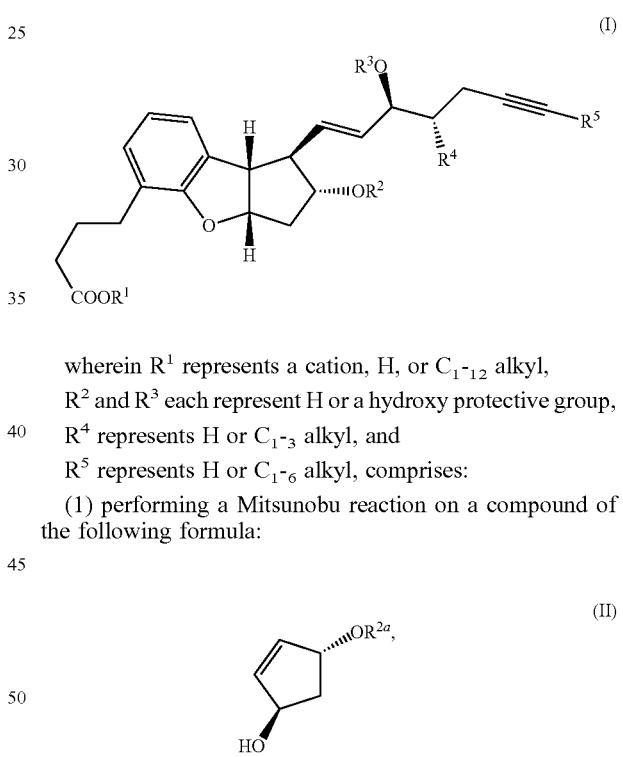

wherein $R^1$ represents a cation, H, or $C_{1}$-$_{12}$ alkyl,
$R^2$ and $R^3$ each represent H or a hydroxy protective group,
$R^4$ represents H or $C_{1}$-$_3$ alkyl, and
$R^5$ represents H or $C_{1}$-$_6$ alkyl, comprises:

(1) performing a Mitsunobu reaction on a compound of the following formula:

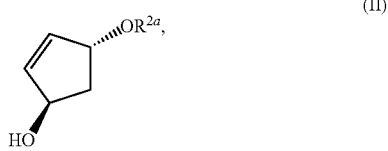

wherein $R^{2a}$ is H or an hydroxy protective group,
with a compound of the following formula:

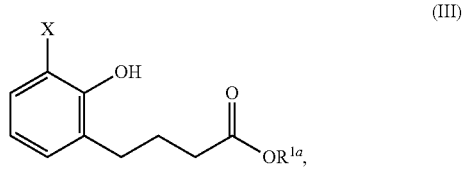

wherein $R^{1a}$ is a cation, H, or $C_{1}$-$_{12}$ alkyl, X is halogen

Figure 1:
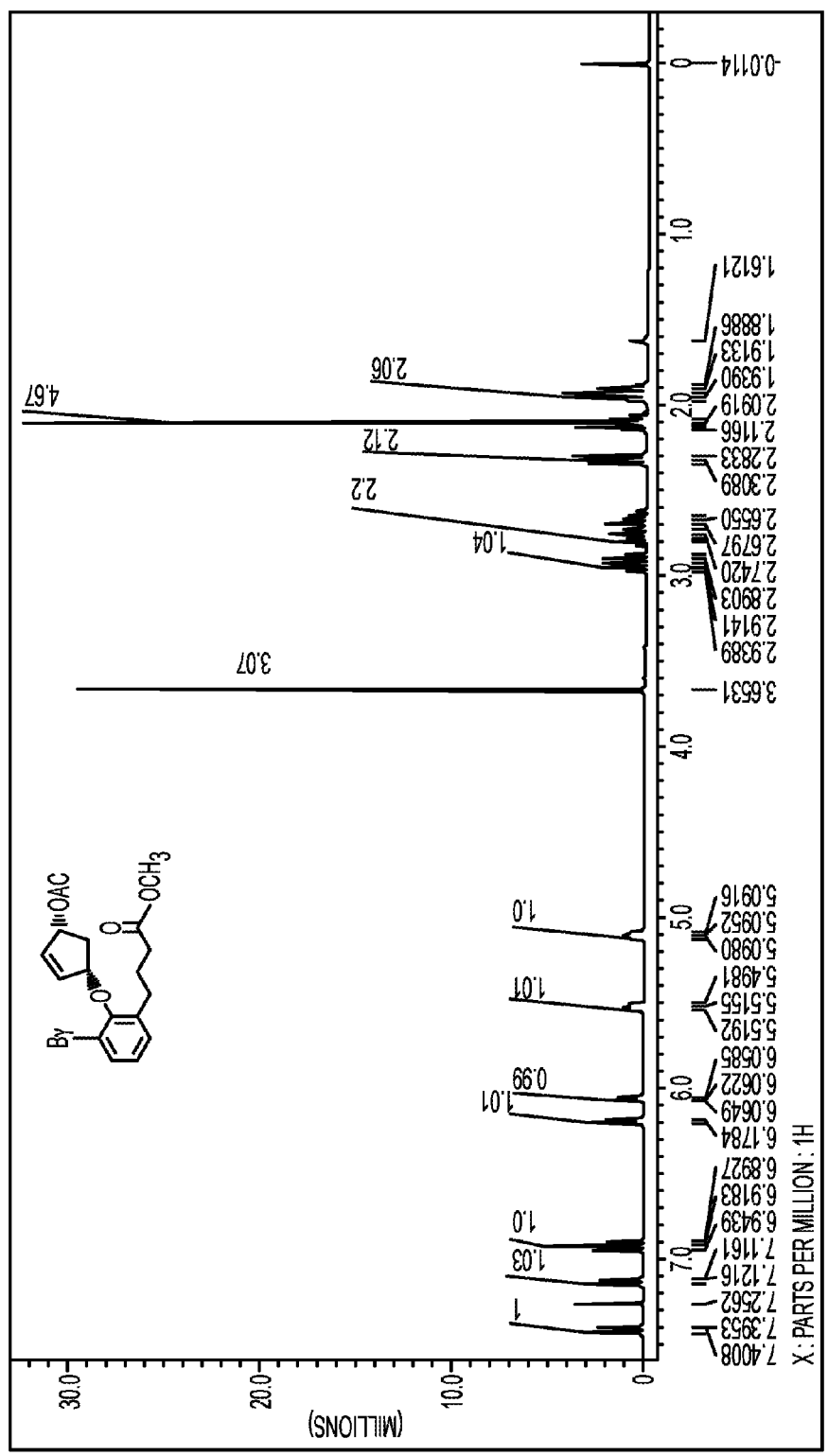
FIG. 1 shows $^1$H NMR spectrum of compound (3).
Figure 2:
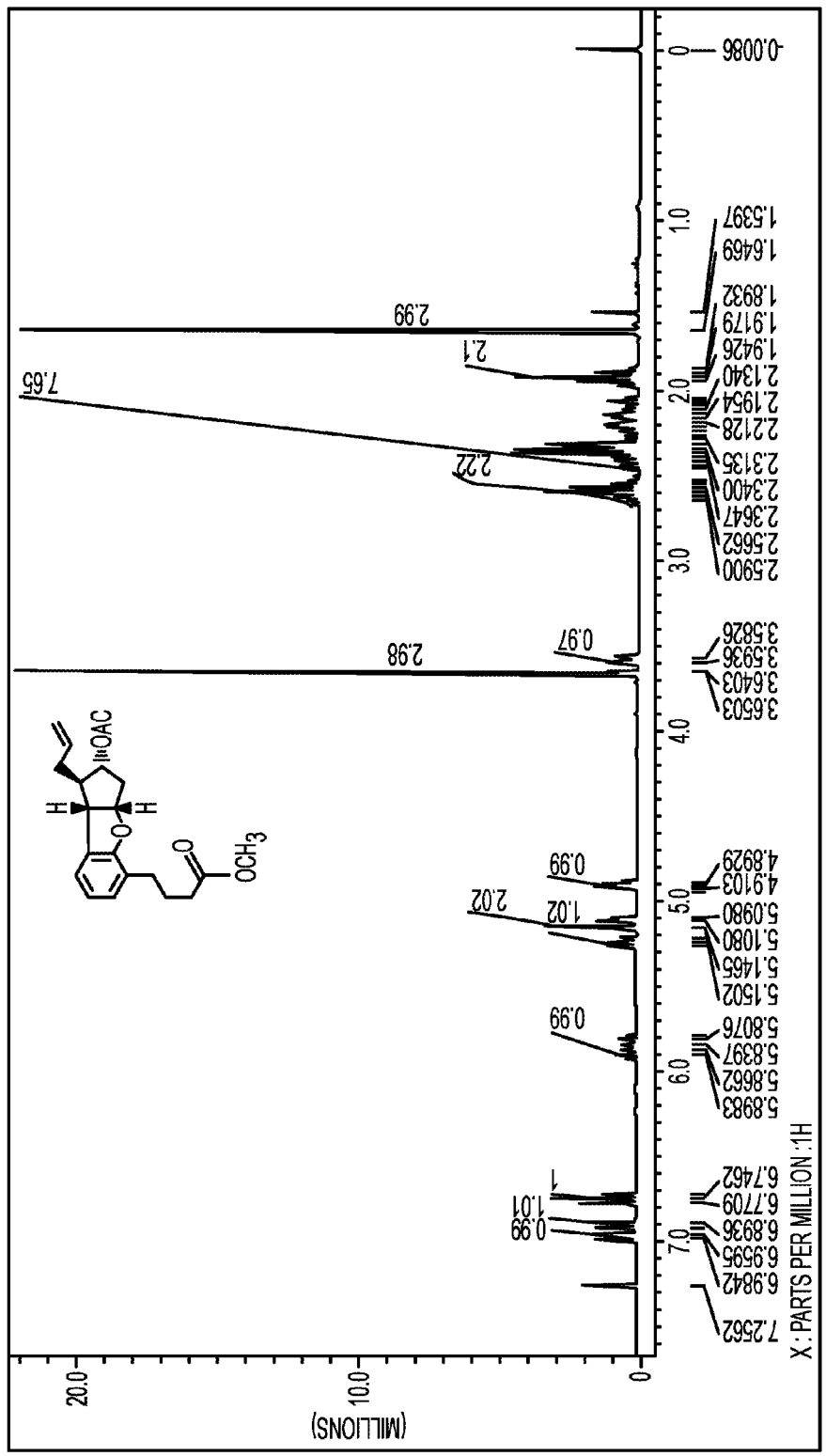
FIG. 2 shows $^1$H NMR spectrum of compound (4).
Figure 3:
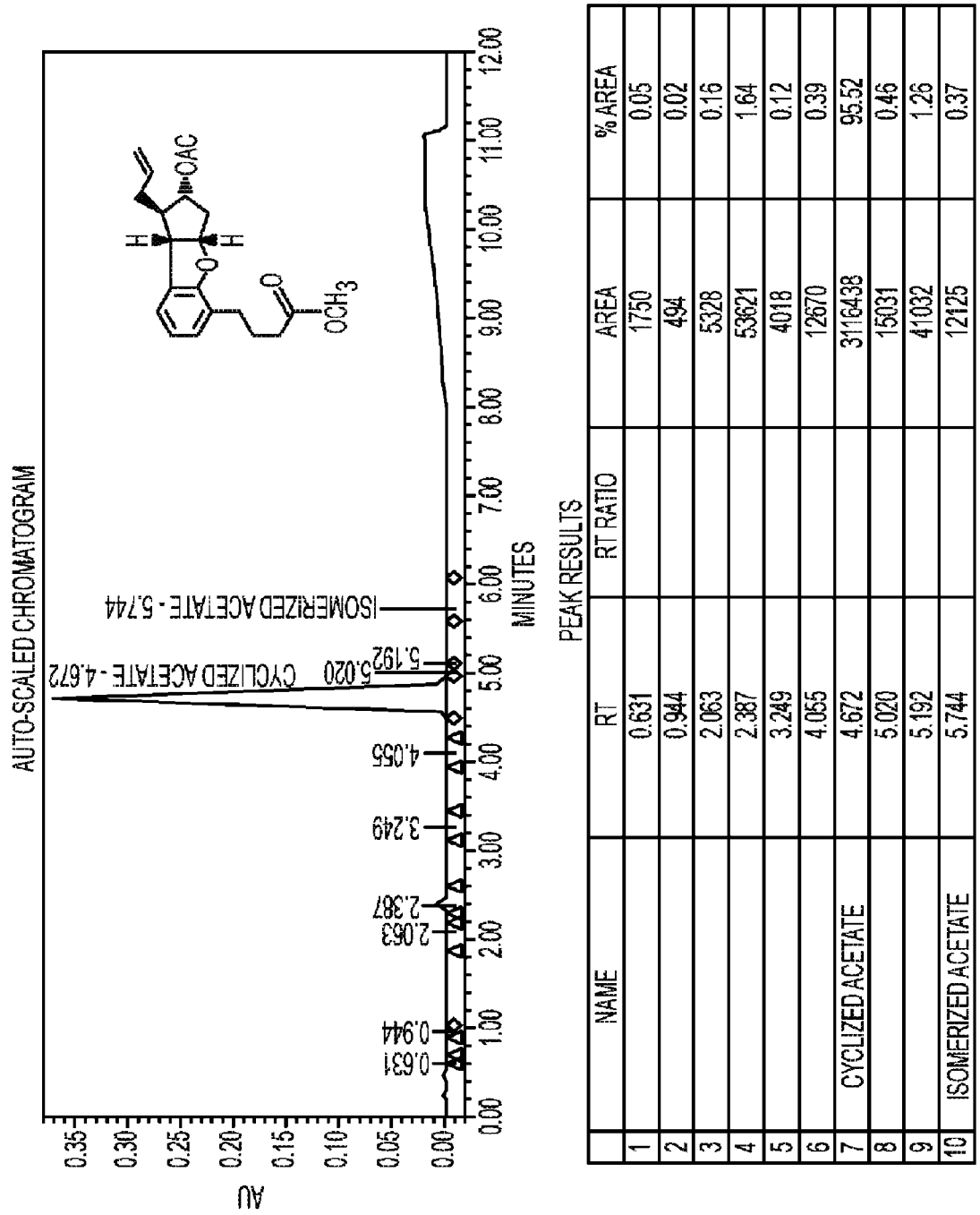
FIG. 3 shows HPLC profile of compound (4).
Figure 4:
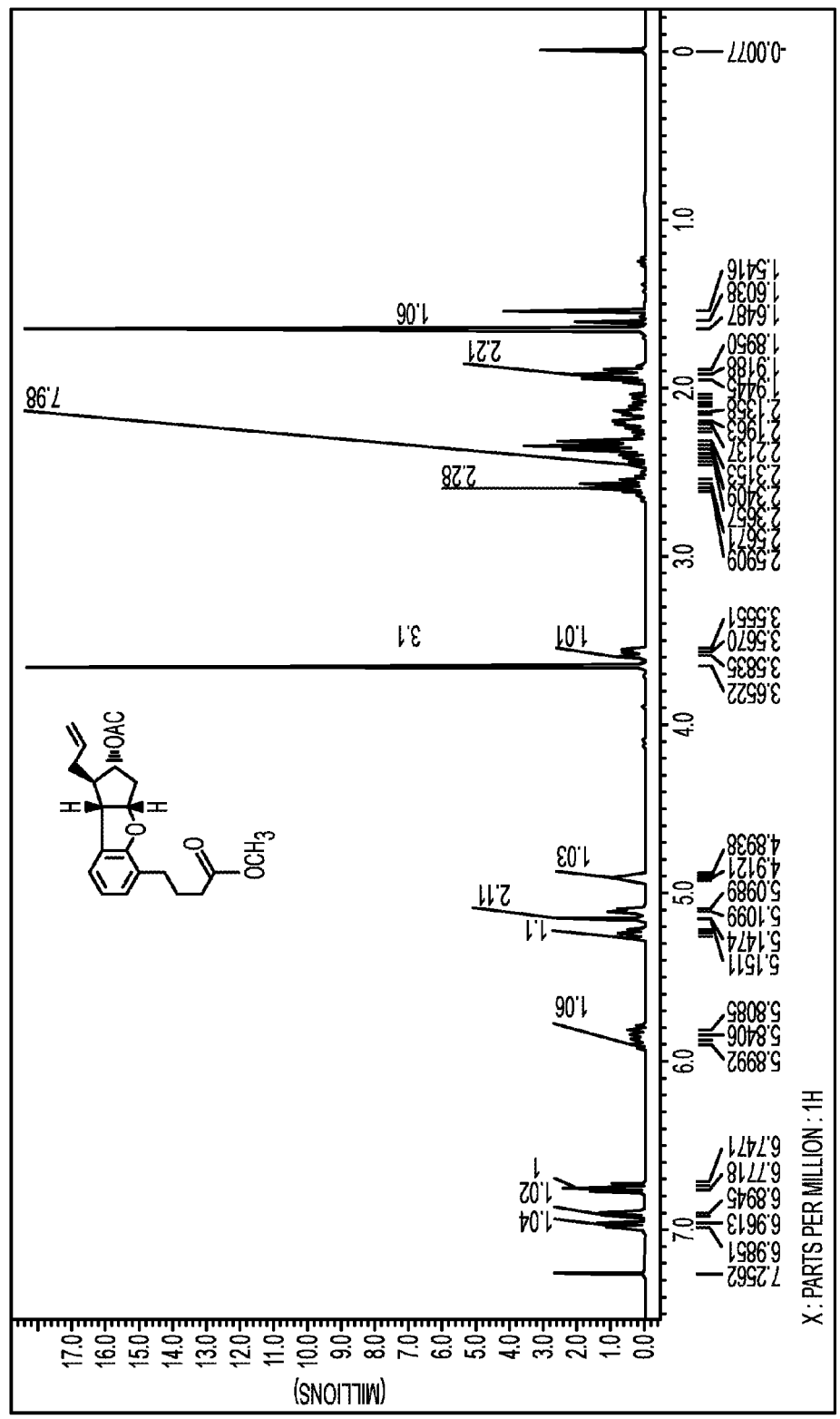
FIG. 4 shows $^1$H NMR spectrum of compound (4).
Figure 5:
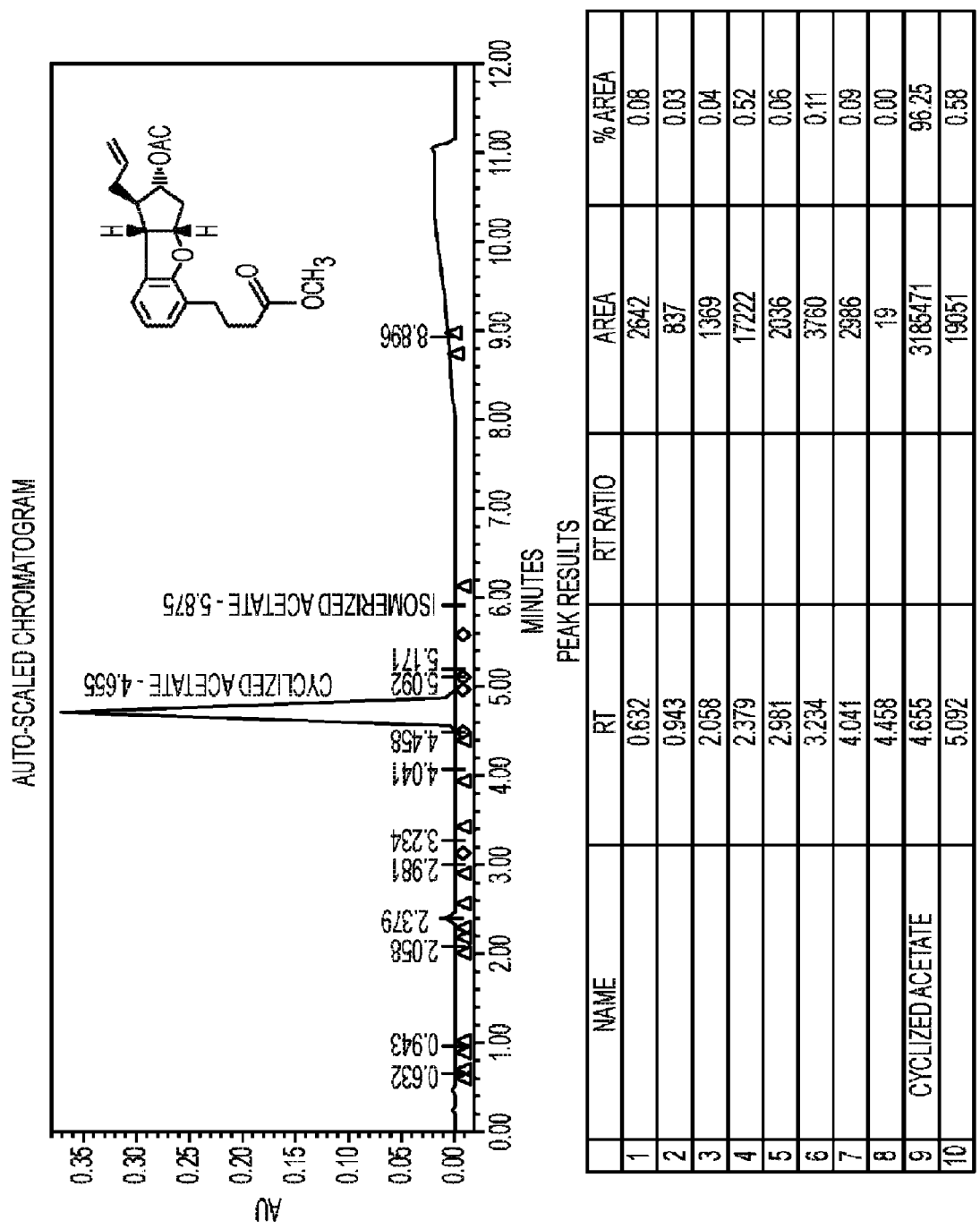
FIG. 5 shows HPLC profile of compound (4).
Figure 6:
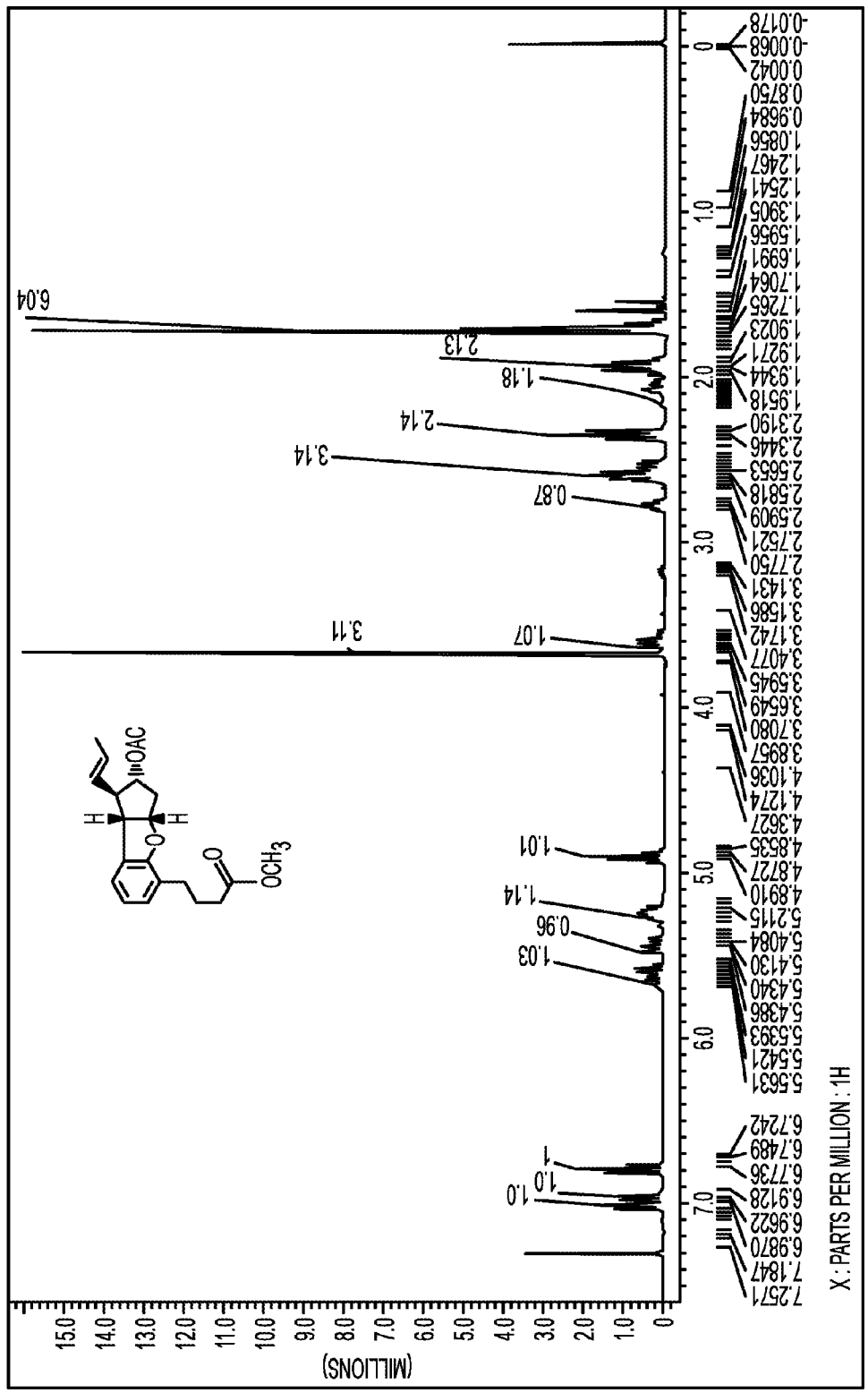
FIG. 6 shows $^1$H NMR spectrum of compound (5).
Figure 7A:
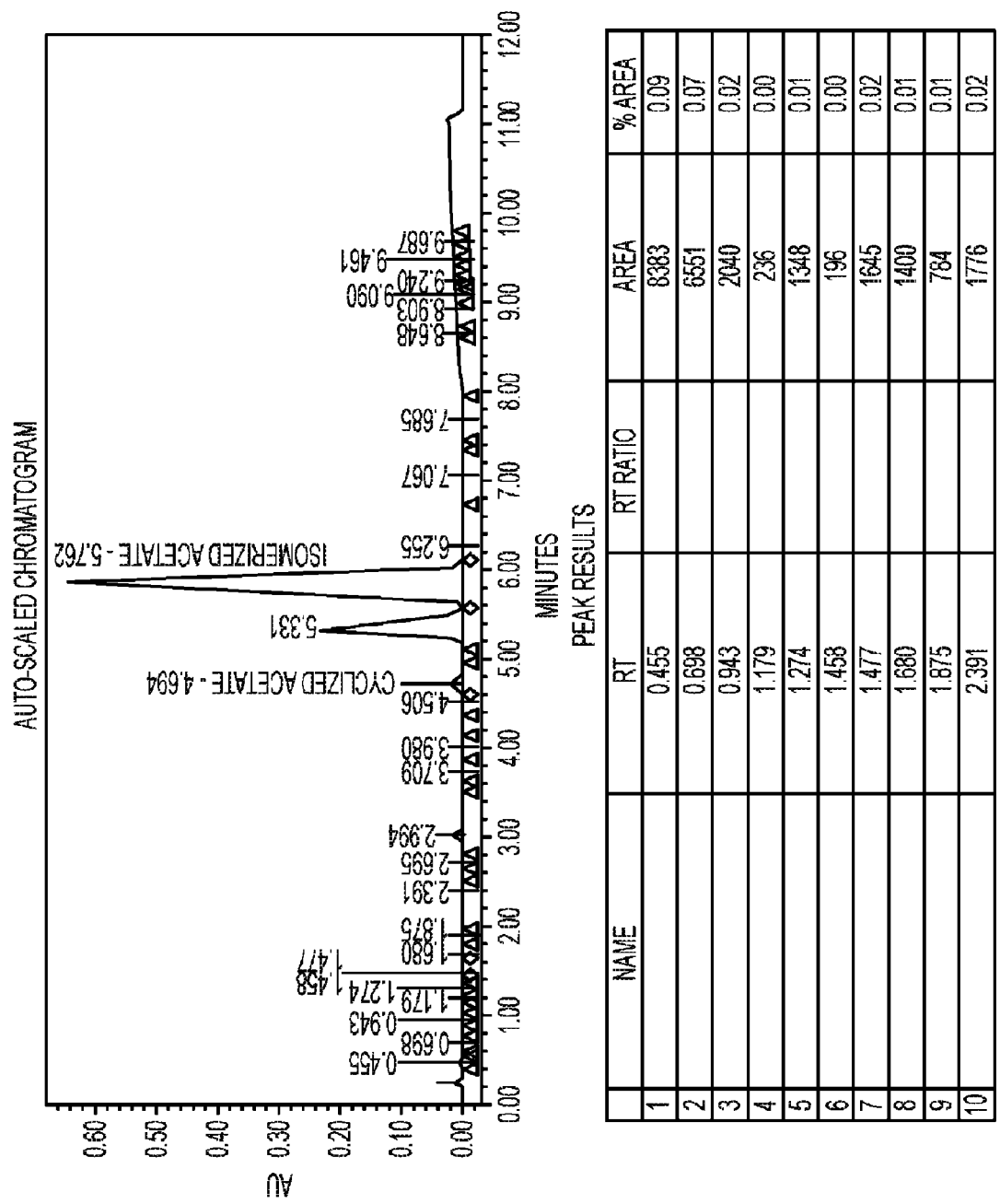
FIGS. 7a and 7b show HPLC profile of compound (5).
Figure 7B:
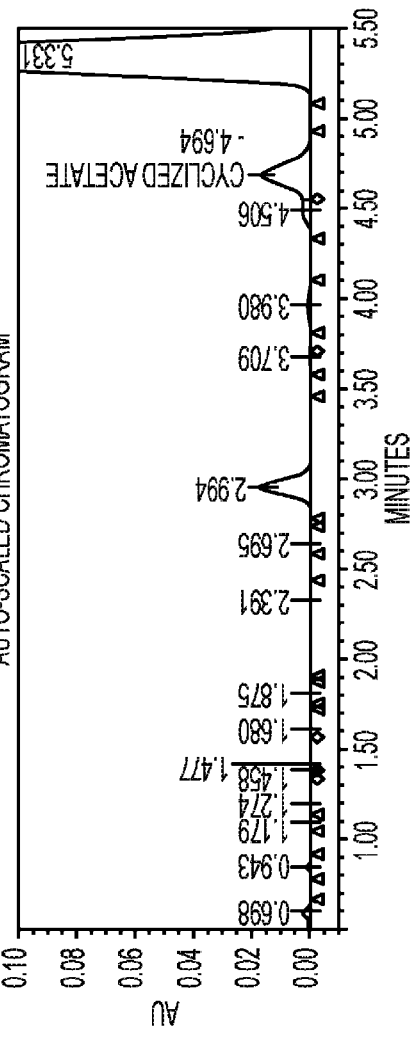
Figure 8:
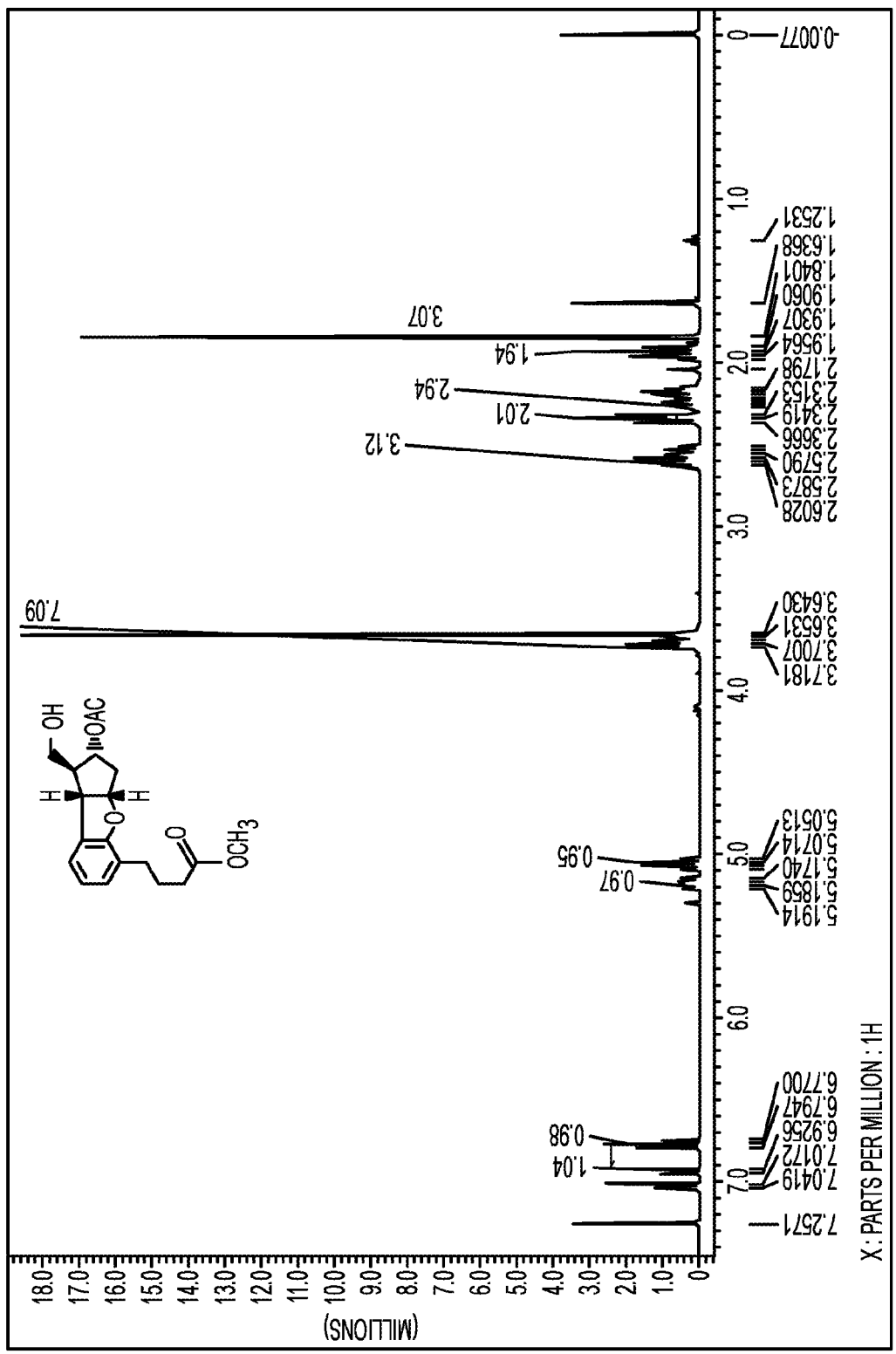
FIG. 8 shows $^1$H NMR spectrum of compound (6).
Figure 9A:
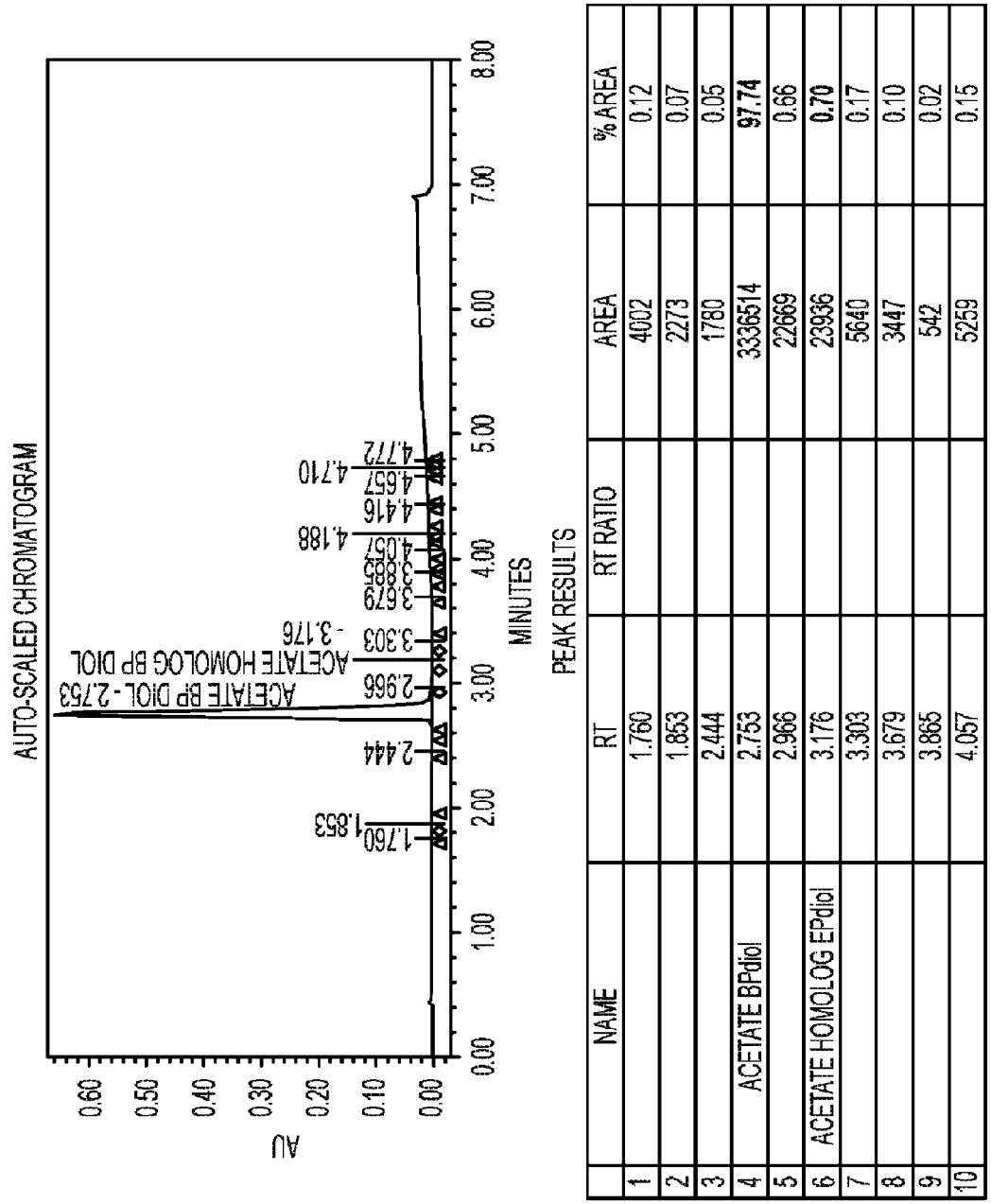
Figure 9B:
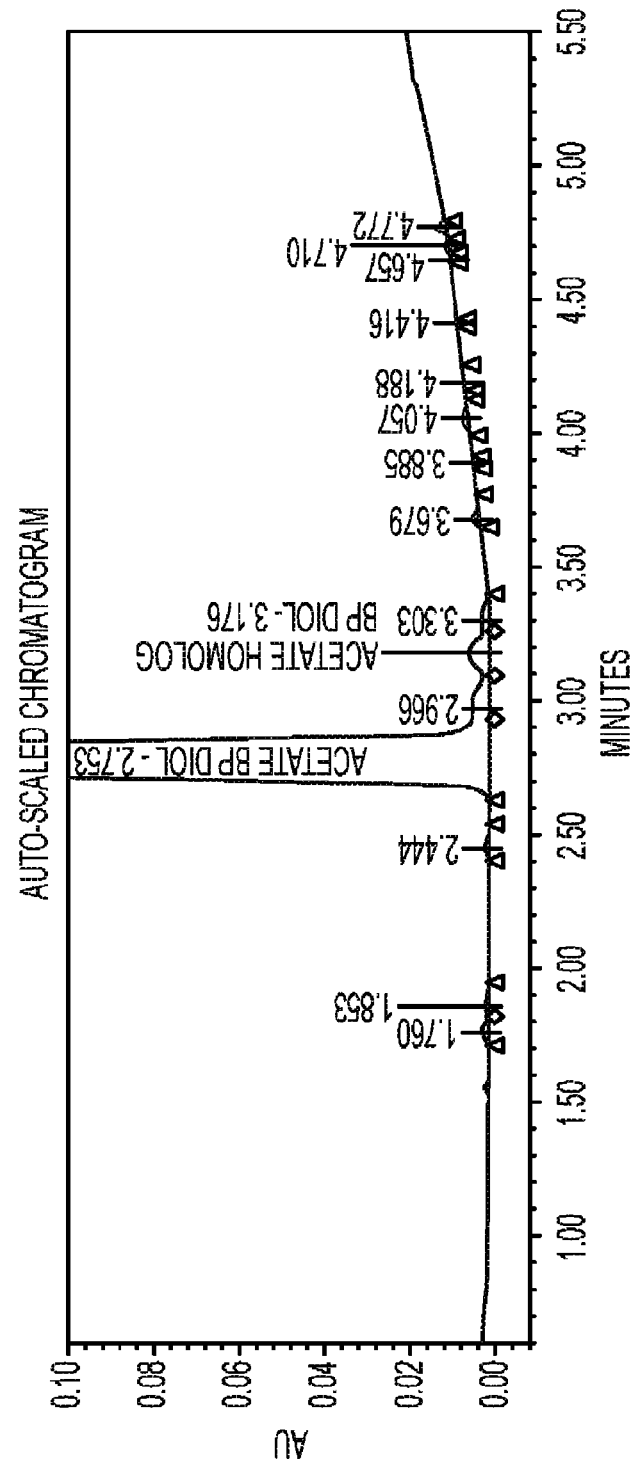
Figure 10:
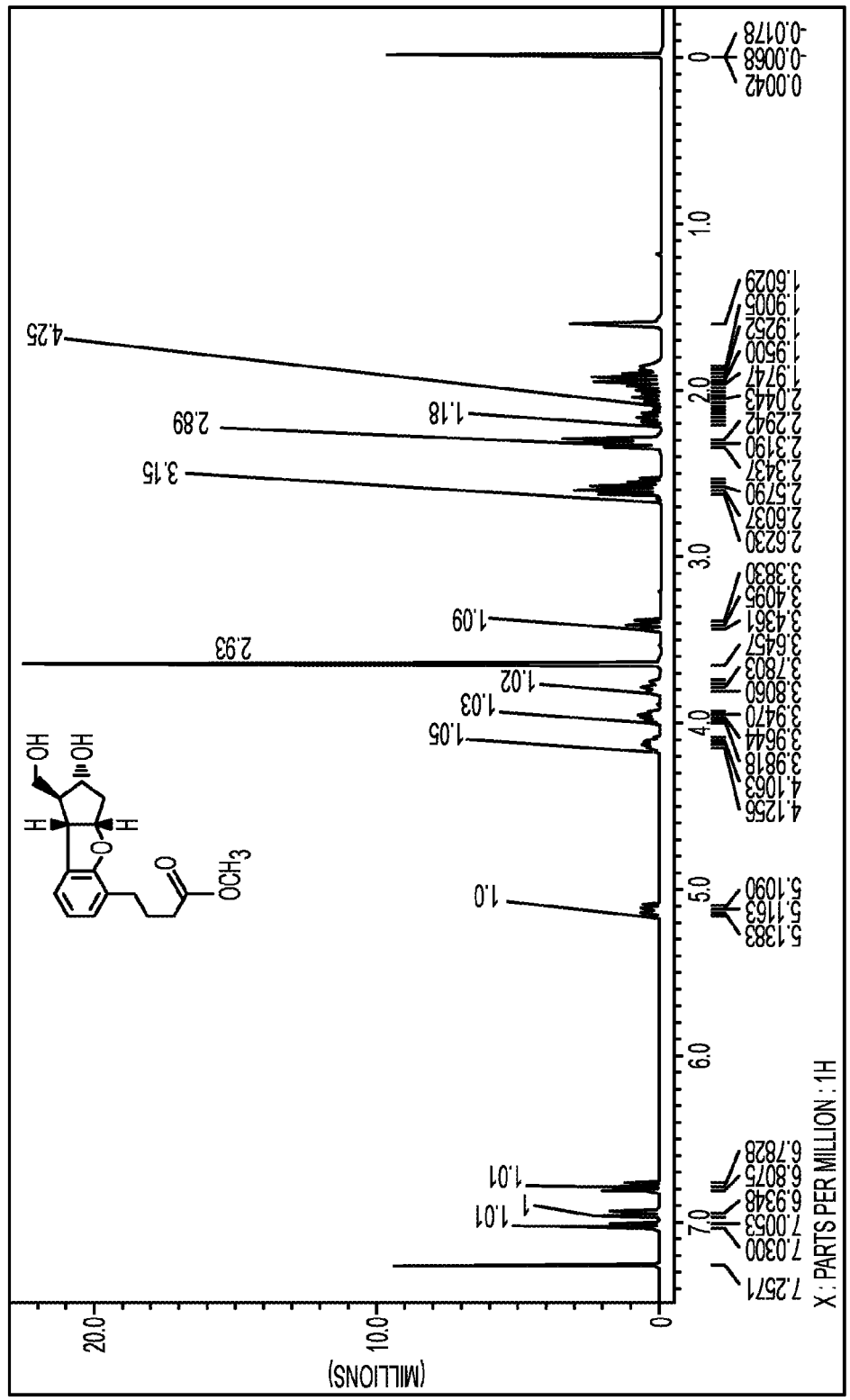
Figure 11:
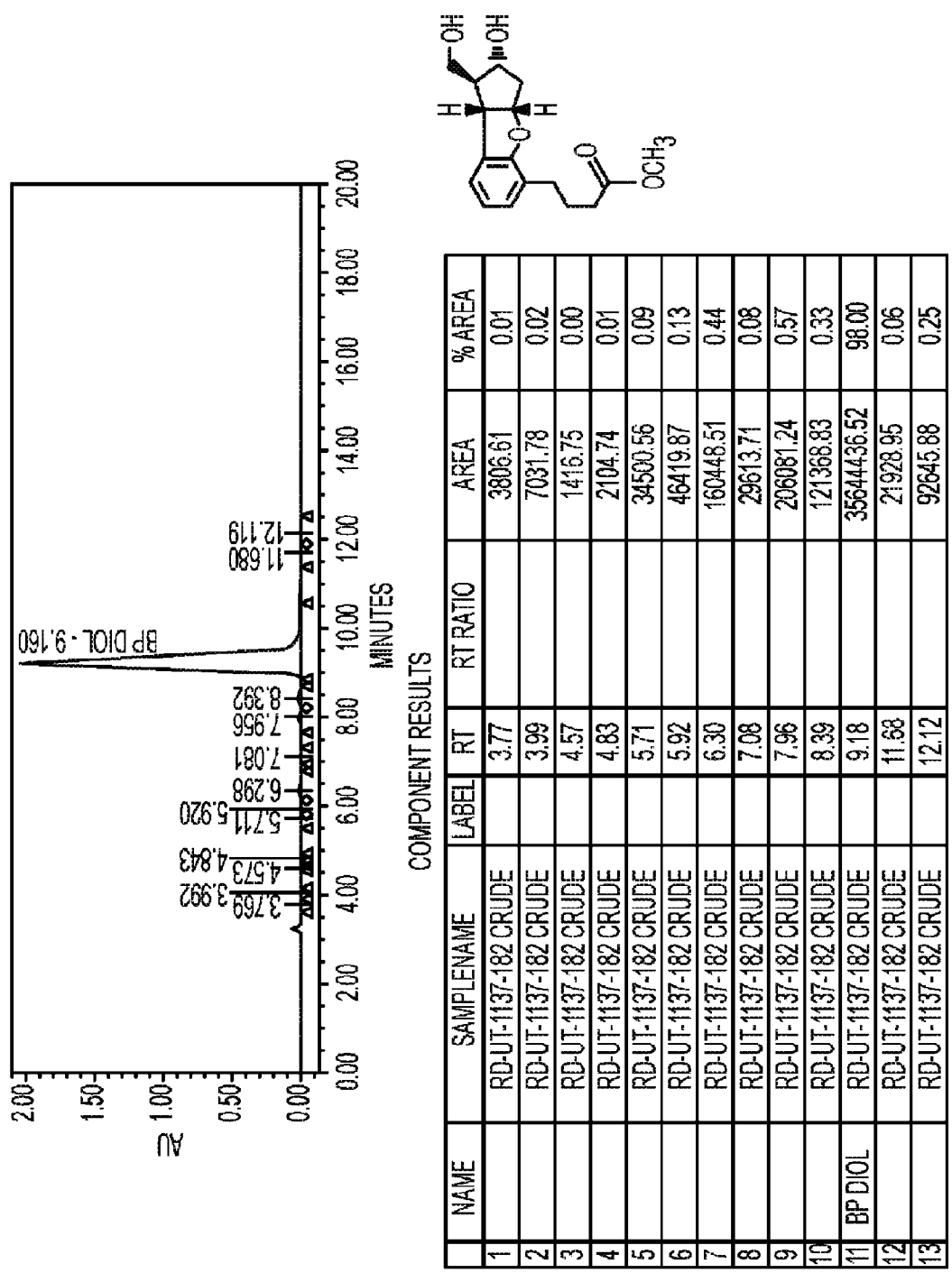
Figure 12:
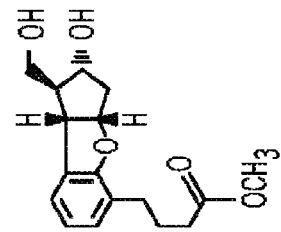
Figure 12:
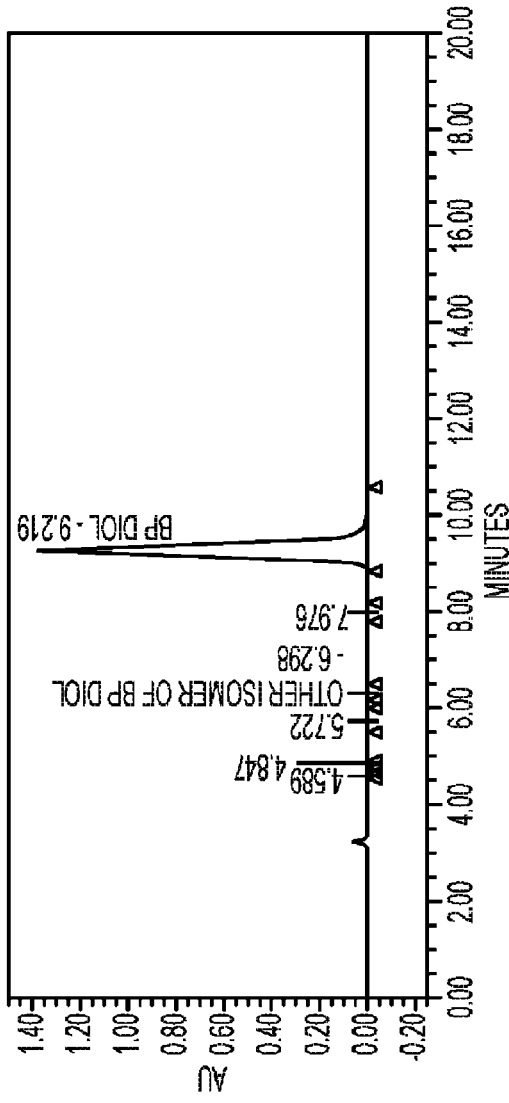
Figure 13:
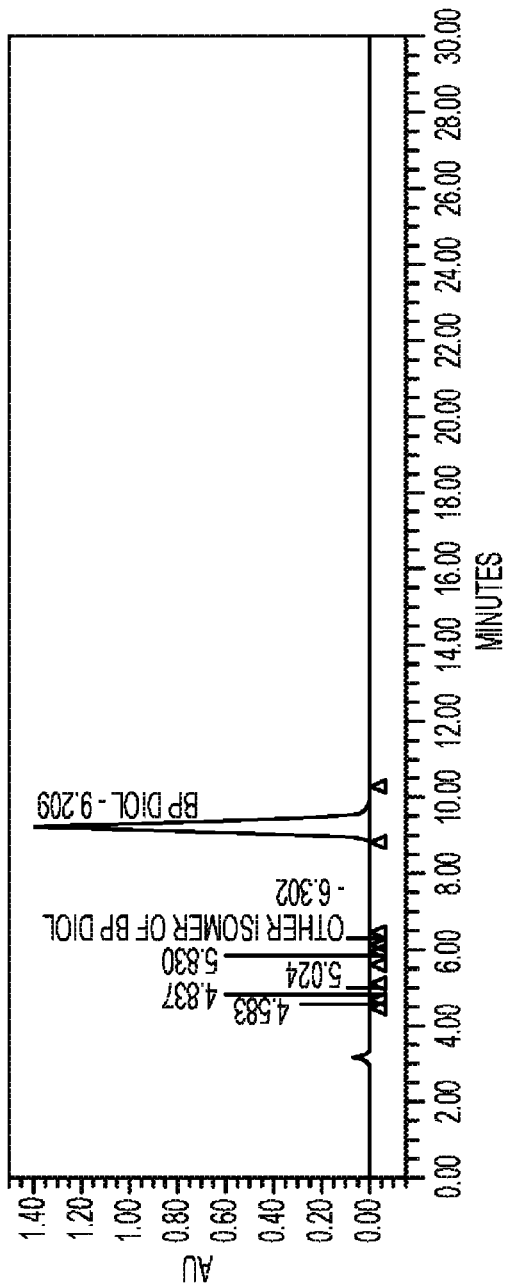
Figure 13:
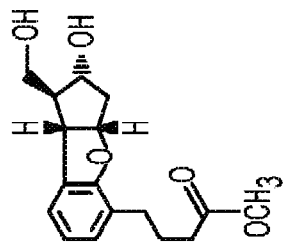
Figure 14:
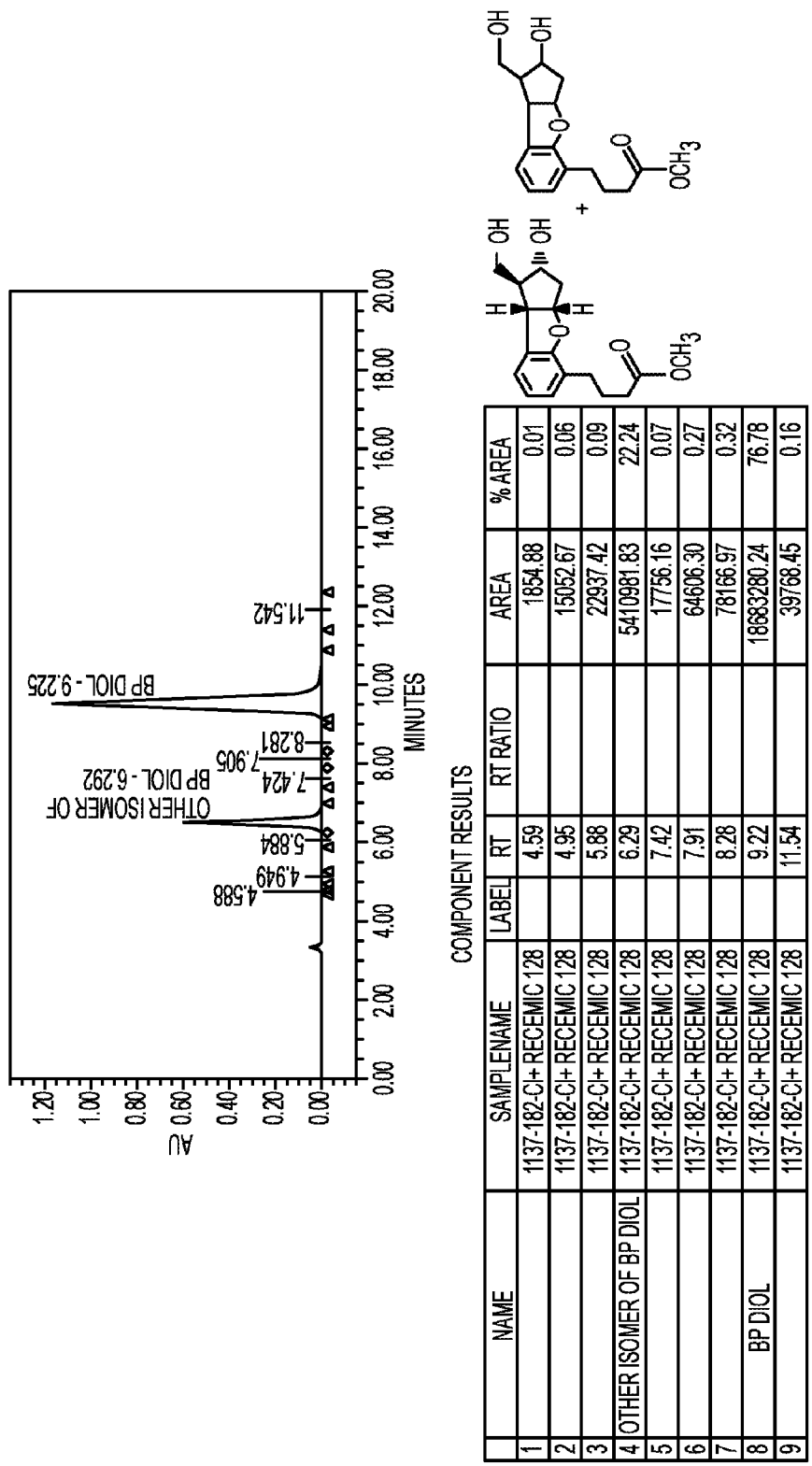
Figure 15:
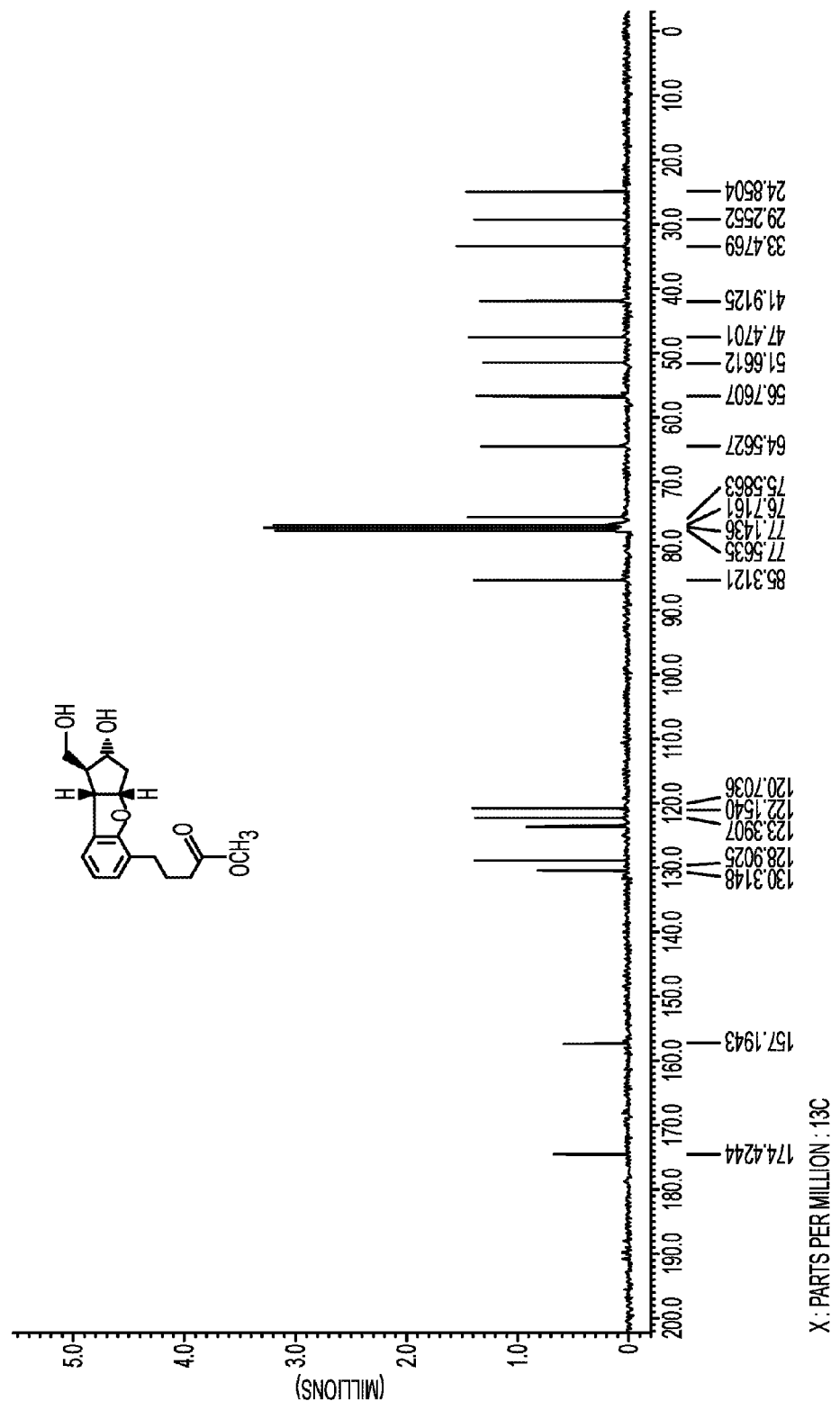
Figure 16:
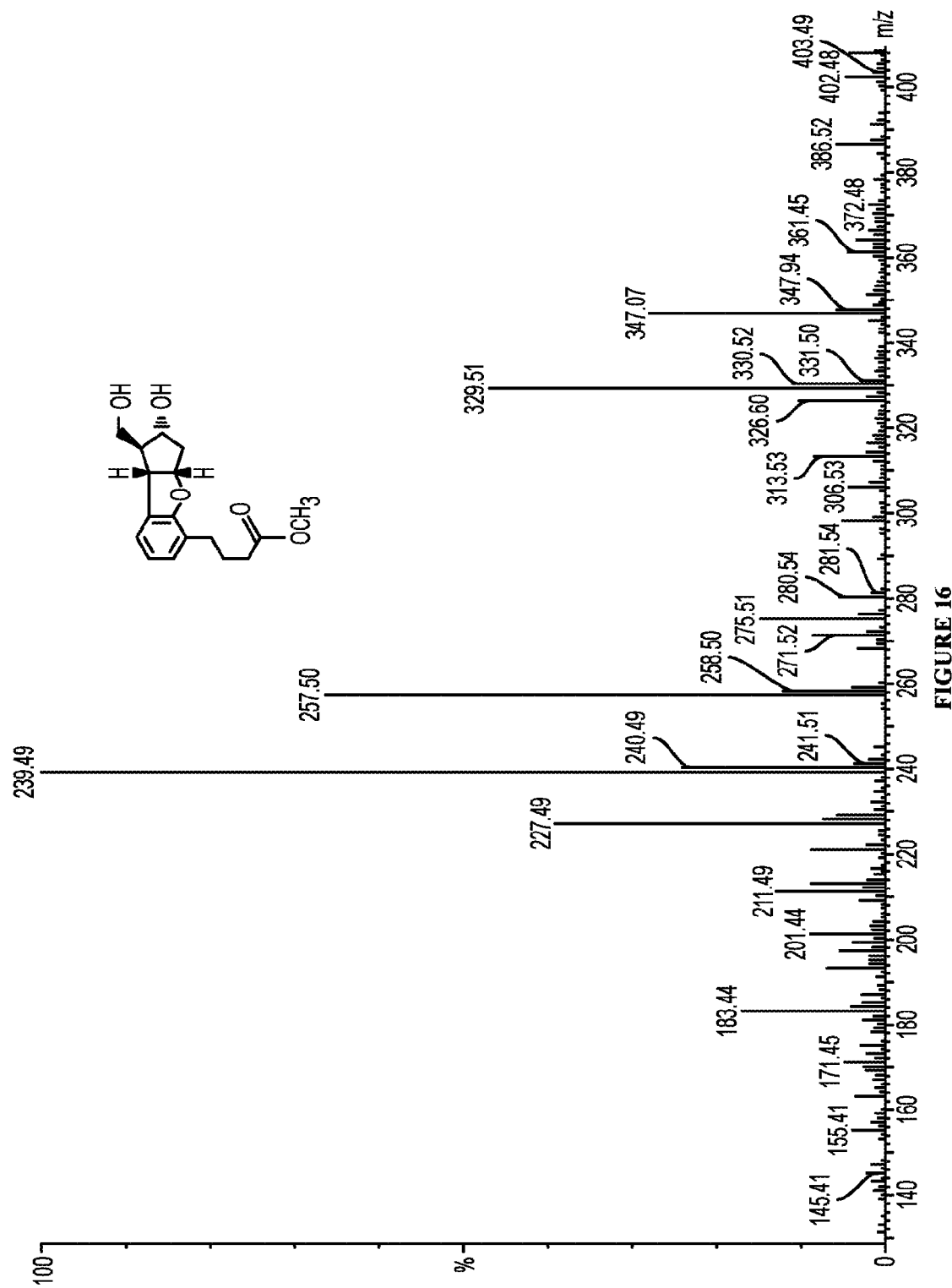

to form a compound of the following formula:

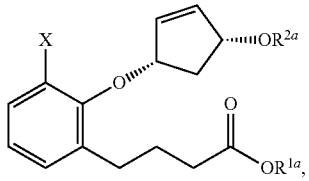 (IV)

wherein $R^{1a}$, $R^{2a}$ and X are each defined above;

(2) radical cyclization of formula (IV) to form a compound of the following formula:

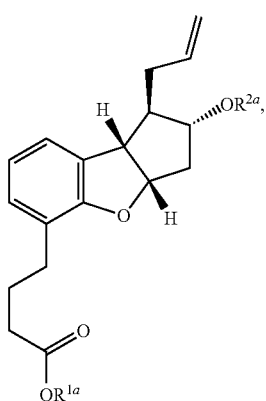 (V)

wherein $R^{1a}$ and $R^{2a}$ are each defined above;

(3) isomerizing the allyl of the compound of formula (V) to form a propenyl resulting in a compound of the following formula:

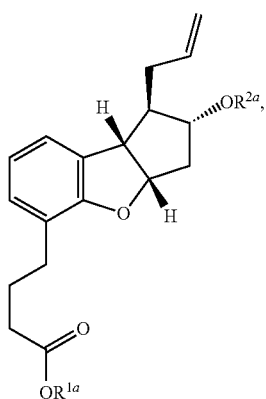 (VI)

wherein $R^{1a}$ and $R^{2a}$ are each defined above;

(4) ozonolysis and in situ reduction to convert the propenyl of the compound of formula (VI) to form an alcohol resulting in a compound of the following formula:

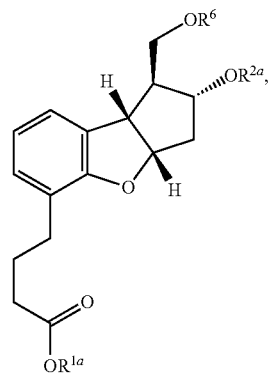 (VII)

wherein $R^{1a}$ and $R^{2a}$ are each defined above, $R^6$ is H or a hydroxy protective group;

(5) deprotection of the acetate of the compound of formula (VII) to form a compound of the following formula:

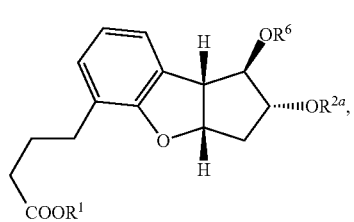 (VIII)

wherein $R^{1a}$, $R^{2a}$, and $R^6$ are each defined above;

(6) selectively deprotecting the primary hydroxy protective group, followed by oxidation of the primary hydroxy group to the corresponding aldehyde, followed by coupling with a side-chain of the formula:

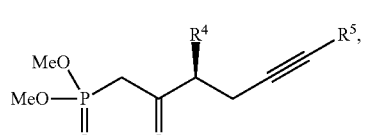 (IX)

wherein $R^4$ and $R^5$ are each defined above to form a compound of the following formula:

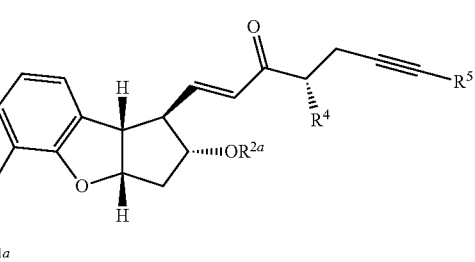 (X)

(7) reduction of the ketone, deprotection of any remaining hydroxy protective group, and optionally converting the $R^{1a}$ into a cation or H to form a compound of the following formula:

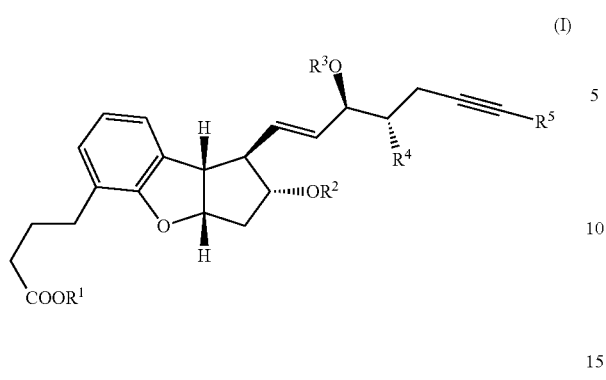

(I)

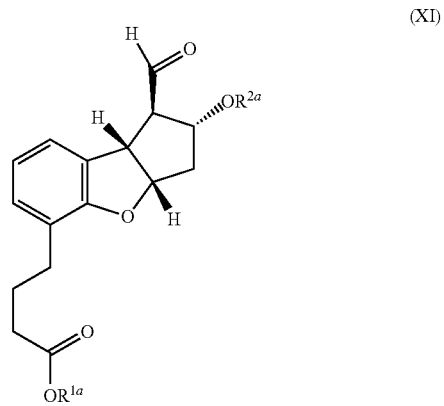

(XI)

Beraprost 314-d is known as the pharmacologically active isomer of beraprost, which exists as a racemic mixture of four isomers and beraprost 314-d can exist as a pharmaceutically acceptable salt. This compound is represented by the compound of formula (I) wherein $R^1$ is a cation or H, $R^2$ and $R^3$ are H, and $R^4$ and $R^5$ are $CH_3$.

In a preferred embodiment, the compound of formula (I) is produced as a substantially pure single isomer without need for separating the desired isomer from other isomers. "Substantially pure" can mean greater than 90% of the desired isomer, greater than 95% of the desired isomer, or greater than 98% of the desired isomer. In some embodiments, $R^2$ and $R^3$, $R^{2a}$, and $R^6$ of the compound of formula (I) each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl. In a preferred embodiment, $R^{1a}$ is $CH_3$, $R^{2a}$ and $R^6$ are both H.

In some embodiments, the radical cyclization of step (2) uses azobisisobutyronitrile as a radical initiator however, it is not limited to only azobisisobutyronitrile there are various other reagents that can be sued as radical initiators including but not limited to 4,4'-Azobis(4-cyanovaleric acid), 4,4'-Azobis(4-cyanovaleric acid), 1,1'-Azobis(cyclohexanecarbonitrile), 2,2'-Azobis(2-methylpropionitrile) and 2,2'-Azobis(2-methylpropionamidine) dihydrochloride.

In some embodiments, the isomerization of step (3) uses a catalytic amount of carbonylchlorohydridotris(triphenylphosphine) ruthenium (II). The isomerization can also be performed by using various other catalysts, including metal catalysts, such as ruthenium metal complexes, such as ruthenium hydride complex and Grubbs catalyst, rhodium metal, such as rhodium chloride ($RhCl_3.xH_2O$), and palladium metal, such as palladium chloride ($PdCl_2$).

In some embodiments, the deprotection of step (5) uses sulfuric acid. However, various other inorganic acids such as HCl and $HNO_3$ can also be used.

In some embodiments, $R^{2a}$ can be a protecting group know to a person of ordinary skill in the art, for example, an alkyl, benzyl (Bn), trimethylsilyl (TMS), tert-butyldimethylsilyl (TBDMS), tert-butyldiphenylsilyl (TBDPS), or an acetate (Ac) group.

In some embodiments, step (4) of the claimed method produces an in situ trapped aldehyde intermediate represented by the compound of formula (XI).

In some embodiments, the reduction of the ketone of formula X may be achieved using a non-selective reducing agent, such as for example sodium borohydride with cerium trichloride heptahydrate, and the subsequent diastereomers separated, or alternatively a chiral reducing agent capable of selectively reducing the ketone may be used to obtain substantially one isomer of the resulting alcohol. Selective reducing agents are known in the art and include, for example, (R)-(+)-2-Butyl-CBS-oxazaborolidine and catecholborane, (R)-(+)-2-Methyl-CBS-oxazaborolidine and catecholborane, (+) DIP-chloride, $NaBH_4$ and 2-(3-Nitrophenyl)-1,3,2-dioxaborolane-4S,5S-dicarboxylic acid (D-TarB-$NO_2$), modified DIBAL reagents, and modified LAH agents.

In one embodiment, the compound of formula (I) is produced as a single isomer represented by formula (I) and in substantially isomerically pure form. In one embodiment, the product represented by formula (I) comprises 90% of the resulting isomeric mixture, or preferably 95% of the resulting isomeric mixture, or more preferably 98% of the resulting isomeric mixture, or even more preferably 99% of the resulting isomeric mixture, and most preferably greater than 99% of the resulting isomeric mixture.

In some embodiments, the beraprost diol of formula (I) is crystallized from MTBE in about 80% yield. In some embodiments, the method produces the compound of formula (I) with a yield of at least 37%. In some embodiments, the method produces the compound of formula (I) with a chiral purity of 99.9% by HPLC.

In some embodiments, a process for preparing a compound of the following formula:

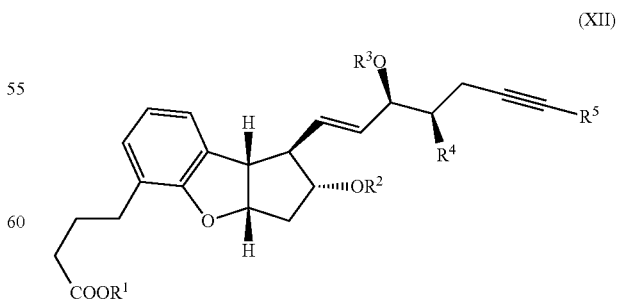

(XII)

wherein $R^1$ represents a cation, H, or $C_1$-$_{12}$ alkyl,
$R^2$ and $R^3$ each represent H or a hydroxy protective group,
$R^4$ represents H or $C_1$-$_3$ alkyl, and $R^5$ represents H or $C_{1-6}$ alkyl, comprises:

(1) reacting a compound of the following formula:

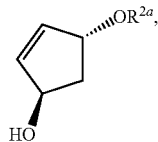
(II)

wherein $R^{2a}$ is H or an hydroxy protective group,
with a compound of the following formula:

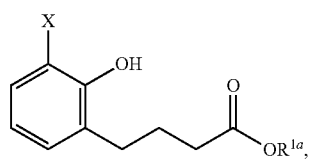
(III)

wherein $R^{1a}$ is a cation, H, or $C_1$-$_{12}$ alkyl, X is a halogen selected from chloro, bromo and iodo,
to form a compound of the following formula:

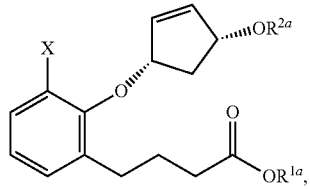
(IV)

wherein $R^{1a}$, $R^{2a}$ and X are each defined above;

(2) cyclizing a compound of formula (IV) to form a compound of the following formula:

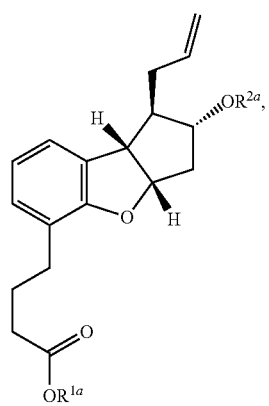
(V)

wherein $R^{1a}$ and $R^{2a}$ are each defined above;

(3) isomerizing an allyl of the compound of formula (V) to form a propenyl resulting in a compound of the following formula:

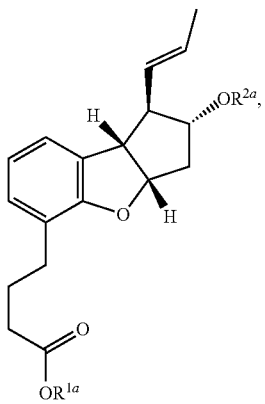
(VI)

wherein $R^{1a}$ and $R^{2a}$ are each defined above;

(4) ozonolysis and in situ reduction to convert the propenyl of the compound of formula (VI) to form an alcohol resulting in a compound of the following formula:

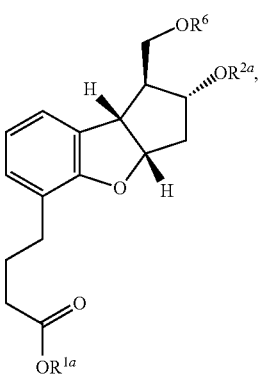
(VII)

wherein $R^{1a}$ and $R^{2a}$ are each defined above, $R^6$ is H or a hydroxy protective group;

(5) deprotecting an acetate of the compound of formula (VII) to form a compound of the following formula:

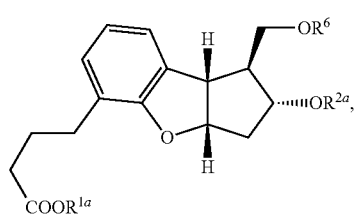
(VIII)

wherein $R^{1a}$, $R^{2a}$ and $R^6$ are each defined above;

(6) selectively deprotecting the primary hydroxy protective group, followed by oxidation of the primary hydroxy group to form an aldehyde, followed by coupling with a side-chain of the formula:

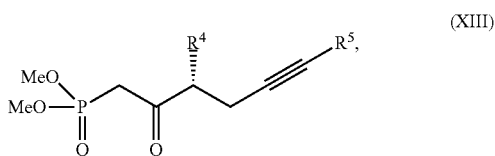
(XIII)

wherein R⁴ and R⁵ are each defined above to form a compound of the following formula:

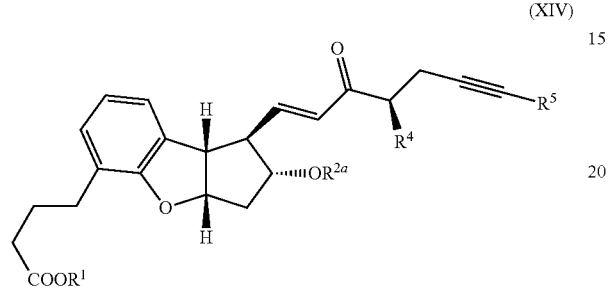
(XIV)

(7) reduction of the ketone, deprotection of any remaining hydroxy protective group and optionally converting the $R^{1a}$ into a cation or H to form a compound of the following formula:

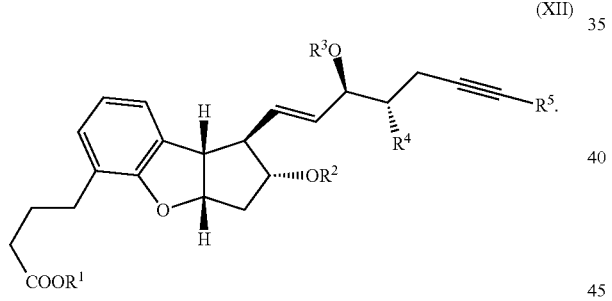
(XII)

In some embodiments, the present invention provides a method that produces the compound of formula (XII) as a substantially pure single isomer.

In some embodiments, $R^2$, $R^3$, $R^{2a}$ and $R^6$ each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl.

In some embodiments, $R^{1a}$ is $CH_3$ and $R^{2a}$ and $R^6$ are both H.

In some embodiments, azobisisobutyronitrile is used as a radical initiator in step (2).

In some embodiments, a catalytic amount of carbonylchlorohydridotris(triphenylphosphine) ruthenium (II) is used in step (3).

In some embodiments, sulfuric acid is used in step (5).

In some embodiments, the present invention provides a process for preparing a compound of the following formula:

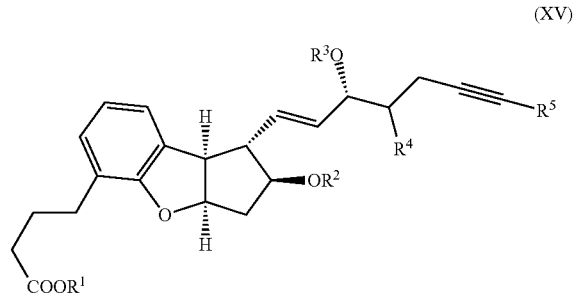
(XV)

wherein $R^1$ represents a cation, H, or $C_{1-12}$ alkyl,
$R^2$ and $R^3$ each represent H or a hydroxy protective group,
$R^4$ represents H or $C_{1-3}$ alkyl, and
$R^5$ represents H or $C_{1-6}$ alkyl, comprising:
(1) reacting a compound of the following formula:

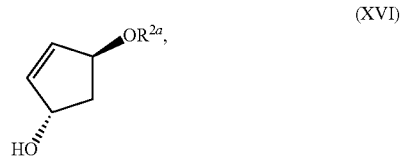
(XVI)

wherein $R^{2a}$ is H or an hydroxy protective group,
with a compound of the following formula:

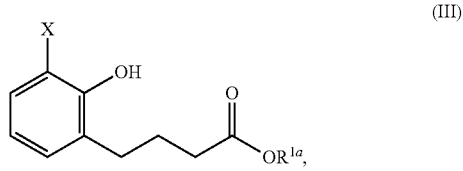
(III)

wherein $R^{1a}$ is a cation, H, or $C_{1-12}$ alkyl, X is a halogen selected from chloro, bromo and iodo,
to form a compound of the following formula:

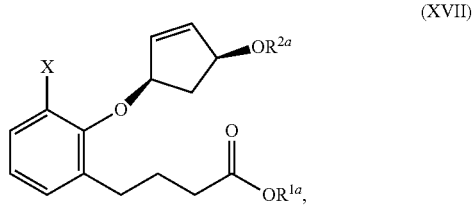
(XVII)

wherein $R^{1a}$, $R^{2a}$ and X are each defined above;
(2) cyclizing a compound of formula (XVII) to form a compound of the following formula:

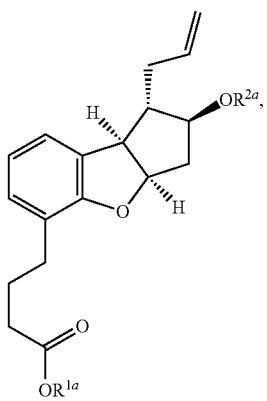

(XVIII)

wherein $R^{1a}$ and $R^{2a}$ are each defined above;

(3) isomerizing an allyl of the compound of formula (XVIII) to form a propenyl resulting in a compound of the following formula:

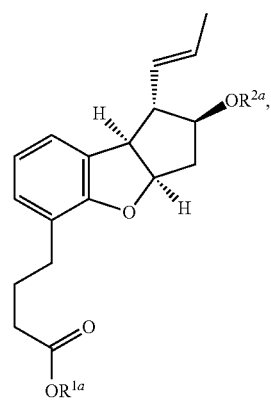

(XIX)

wherein $R^{1a}$ and $R^{2a}$ are each defined above;

(4) ozonolysis and in situ reduction to convert the propenyl of the compound of formula (XIX) to form an alcohol resulting in a compound of the following formula:

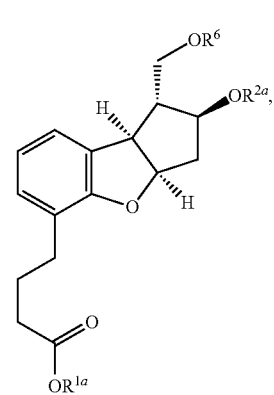

(XX)

wherein $R^{1a}$ and $R^{2a}$ are each defined above, $R^6$ is H or a hydroxy protective group;

(5) deprotecting an acetate of the compound of formula (XX) to form a compound of the following formula:

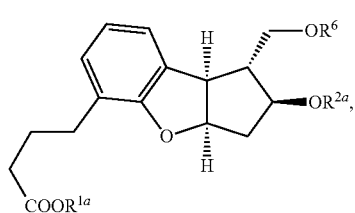

(XXI)

wherein $R^{1a}$, $R^{2a}$ and $R^6$ are each defined above;

(6) selectively deprotecting the primary hydroxy protective group, followed by oxidation of the primary hydroxy group to form an aldehyde, followed by coupling with a side-chain of the formula:

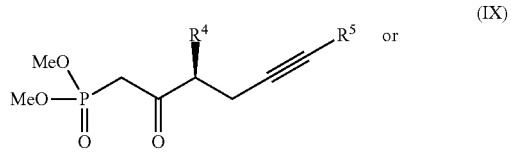

(IX)

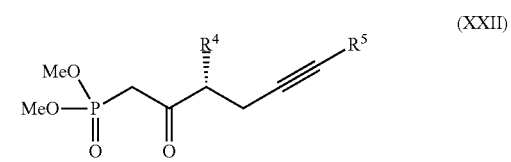

(XXII)

wherein $R^4$ and $R^5$ are each defined above to form a compound of the following formula:

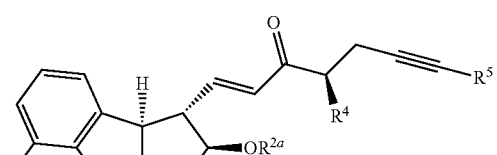

(XXIII)

(XXIV)

(7) reduction of the ketone, deprotection of any remaining hydroxy protective group and optionally converting the $R^{1a}$ into a cation or H to form a compound of the following formula:

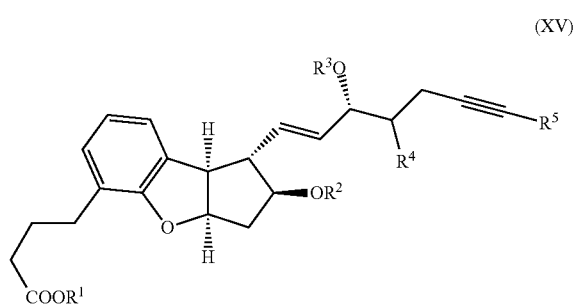

(XV)

In some embodiments, the methods described herein produce the compound of formula (XV) as a substantially pure single isomer of the formula

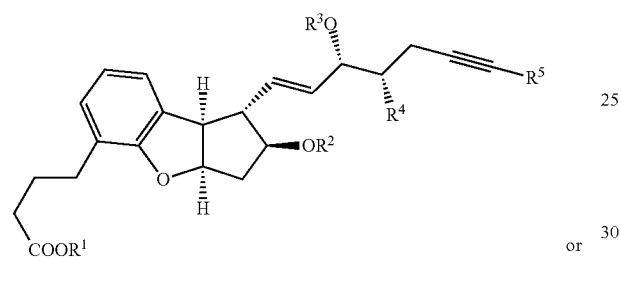

(XXV)

or

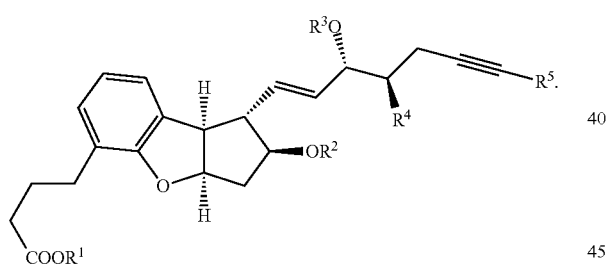

(XXVI)

In some embodiments, $R^2$, $R^3$, $R^{2a}$ and $R^6$ each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl.

In some embodiments, $R^{1a}$ is $CH_3$ and $R^{2a}$ and $R^6$ are both H.

In some embodiments, azobisisobutyronitrile is used as a radical initiator in step (2).

In some embodiments, a catalytic amount of carbonylchlorohydridotris(triphenylphosphine) ruthenium (II) is used in step (3).

In some embodiments, sulfuric acid is used in step (5).

In some embodiments, the present invention provides a process for preparing a compound of the following formula:

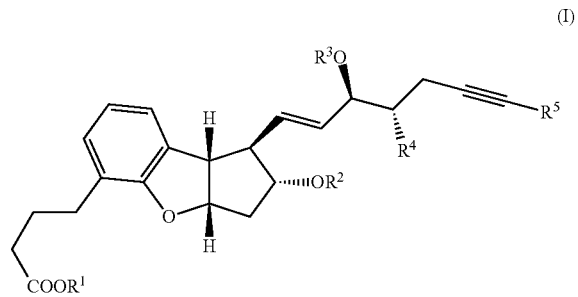

(I)

wherein $R^1$ represents a cation, H, or $C_{1-12}$ alkyl,
$R^2$ and $R^3$ each represent H or a hydroxy protective group,
$R^4$ represents H or $C_{1-3}$ alkyl, and
$R^5$ represents H or $C_{1-6}$ alkyl, comprising:

(1) protecting a hydroxyl group of a compound of the following formula:

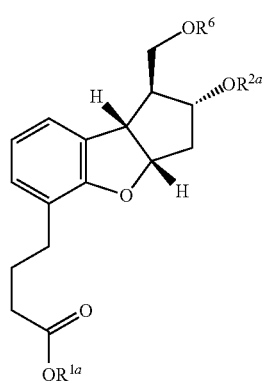

(VII)

wherein $R^{1a}$ is a cation, H, or $C_{1-12}$ alkyl; $R^{2a}$ and $R^6$ are each H or a hydroxy protective group, to produce a compound of the following formula:

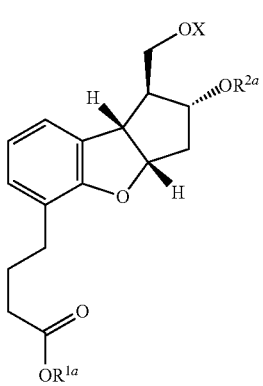

(XXVII)

wherein X is a trityl protecting group;

(2) protecting a hydroxyl group of the compound of (XXVII) to form a compound of the following formula:

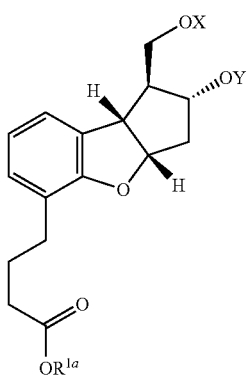

(XXVIII)

wherein Y is TBDMS group;

(3) deprotection one of the hydroxyl protective groups to form a compound of the following formula:

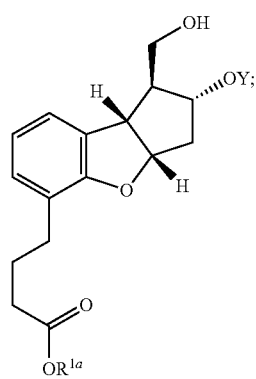

(XXIX)

(4) oxidation of a hydroxyl group of the compound to form a compound of the following formula:

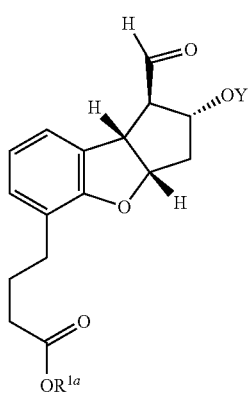

(XXX)

(5) Reacting with stannanes to form a compound of the following formula:

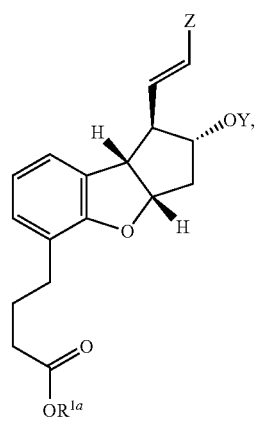

(XXXI)

where in Z is $SnBu_3$ (6) coupling with a compound of the following formula:

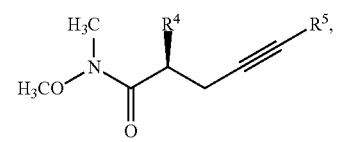

(XXXII)

to form a compound of the following formula:

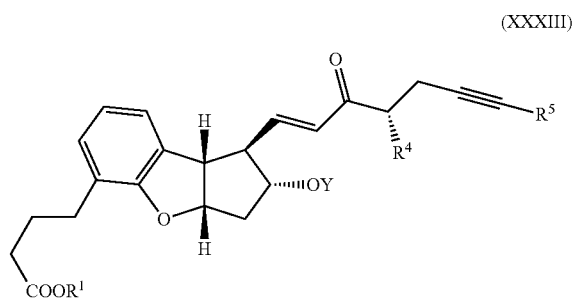

(XXXIII)

wherein $R^1$, $R^2$, $R^4$ and $R^5$ are each defined above, (7) deprotecting the protective group Y and reducing the ketone of the compound of the formula (XXXIII) to form a compound of the following formula:

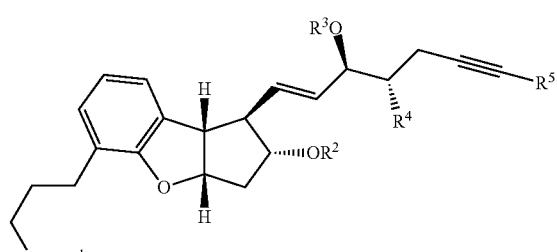

(I)

In some embodiments, the present invention provides a method that produces the compound of formula (I) as a substantially pure single isomer.

In some embodiments, the present invention provides a process for preparing a compound of the following formula:

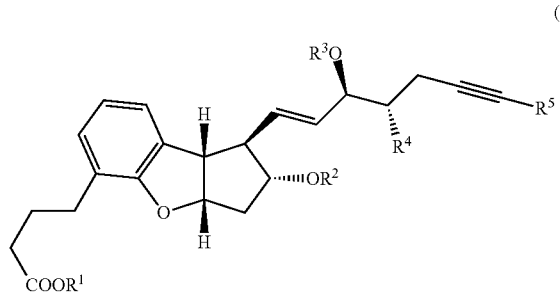
(I)

wherein R¹ represents a cation, H, or $C_{1-12}$ alkyl,
R² and R³ each represent H or a hydroxy protective group,
R⁴ represents H or $C_{1-3}$ alkyl, and
R⁵ represents H or $C_{1-6}$ alkyl, comprising:
(1) reacting a compound of the following formula:

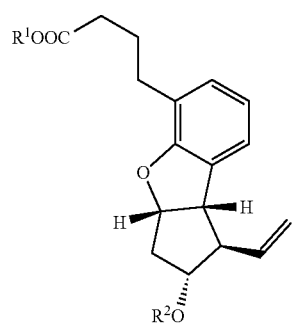
(XXXIV)

with a compound of the following formula:

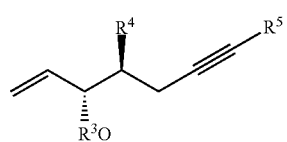
(XXXV)

in a Grubbs II metathesis reaction, and
(2) base hydrolysis to produce the compound of formula (I).

In some embodiments, the methods described herein produce the compound of formula (I) as a substantially pure single isomer.

The present invention is further illustrated by, though in no way limited to, the following examples.

EXAMPLE 1

Synthesis of Bromophenyl Acetoxycyclopentenyl Ether (3)

A 500 mL, three necked, round bottom flask fitted with a dropping funnel, argon inlet and a rubber septum was charged with a solution of (1R,4R)-4-hydroxycyclopent-2-en-1-yl acetate (1) (10.0 g, 70.34 mmol), 2-bromophenol-6-carbomethoxypropane (2) (21.1 g, 77.37 mmol), triphenylphosphine (20.29 g, 77.37 mmol) and triethylamine (7.8 g, 77.37 mmol) in anhydrous tetrahydrofuran (100 mL). To this, diisopropyl azodicarboxylate (15.6 g, 77.37 mmol) was added drop wise at 0° C. over a period of 45 mins. After complete addition, reaction mixture was allowed to attain room temperature slowly. The progress of the reaction was monitored by a TLC with dimensions of 2.5×7.5 cm was used to elute reaction mixture in 20% ethyl acetate and hexanes to confirm complete consumption of starting material. At this stage, the reaction was complete and quenched with a saturated solution of ammonium chloride (150 mL). The organic layer was separated and aqueous layer was extracted with ethyl acetate (2×100 mL). The combined organic layers were washed with brine, dried over sodium sulfate and evaporated in vacuo to obtain crude product (78 g). This was combined with Lot #RD-UT-1137-169 (1 g scale) and purified by chromatography to obtain pure bromophenyl acetoxycyclopentenyl ether (3) (27.5 g, 89.5%). Specifically, a filter-type column of diameter 11.5 cm and 18 cm in length packed with silica gel (551.7 g) was used for purification using ethyl acetate and hexanes. The polarity of the solvent was increased from 0 to 13%. This compound was characterized by ¹H NMR.

TABLE 1

Materials used in Example 1

| Name | MW | Lot No. | Amount | mmol | Eq. |
|---|---|---|---|---|---|
| (1R,4R)-4-hydroxycyclopent-2-en-1-yl acetate (1) | 142.16 | SSL-0080-148-30 | 10.0 g | 70.34 | 1.0 |
| 2-Bromopenol-6-carbomethoxypropane (2) | 273.12 | 20141104 | 21.1 g | 77.37 | 1.1 |
| Diisopropyl azodicarboxylate (DIAD) | 202.21 | T-09-0210 | 15.6 g | 77.37 | 1.1 |
| Triphenylphosphine | 262.29 | MKBK2887V | 20.29 g | 77.37 | 1.1 |
| Triethylamine | 101.19 | T-11-0541 | 7.8 g | 77.37 | 1.1 |
| Tetrahydrofuran (anhydrous) | NA | SHBD8022V | 100 mL | NA | NA |
| Silica gel (230-400 mesh) | NA | 80107 | 551.7 g | NA | NA |

The reaction in Example 1 is described in the scheme below:

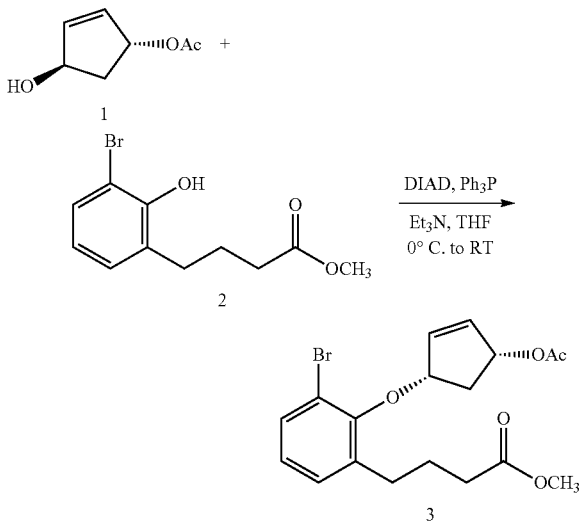

EXAMPLE 2

Synthesis of Allyl Acetoxycyclopentabenzofuran (4)

A 1000 mL, three necked, round bottom flask fitted with a condenser, a dropping funnel and a rubber septum was charged with a solution of bromophenyl acetoxycyclopentenyl ether (3) (27.0 g, 68.00 mmol) and allyltributylstannane (135.1 g, 408.00 mmol) in anhydrous toluene (50 mL) and heated to 110° C. under argon. The reaction system was evacuated to remove atmospheric air and replaced with argon. To this solution a suspension of AIBN (5.6 g, 34.00 mmol) in toluene (100 mL) was added in one portion and heating was continued at reflux temperature for 10 minutes. The progress of the reaction was monitored by a TLC with dimensions of 2.5×7.5 cm was used to elute reaction mixture in 25% ethyl acetate and hexanes to confirm complete consumption of starting material. A longer TLC helped in resolving the spot closer to the Rf value of starting material. At this stage, the reaction was complete and the reaction mixture was cooled to ambient temperature. This reaction mixture was concentrated in vacuo to remove toluene to half the original volume and then loaded directly onto the silica gel packed column for purification. Specifically, a filter-type column of diameter 11.5 cm and 18 cm length was packed with silica gel (579.7 g) was used for purification using ethyl acetate and hexanes. The polarity of the solvent was increased from 0 to 9%. A smaller filter type column of diameter 9.5 cm and 15 cm length packed with silica gel (396.2 g) was used for purifying impure fractions using the above solvents and polarity. The pure fractions yielded 8.9 g (Lot #RD-UT-1137-175-I) with 95.5% purity (by UPLC) and impure fractions were purified again by a second column chromatography to yield 7.03 g (Lot #RD-UT-1137-175-II) with 96.26% purity (by UPLC). The total isolated yield of allyl acetoxycyclopentabenzofuran (4) was 15.9 g (65.5%). The compound was characterized by $^1$H NMR.

TABLE 2

| Material used in Example 2 | | | | | |
|---|---|---|---|---|---|
| Name | MW | Lot No. | Amount | mmol | Eq. |
| Bromophenyl acetoxycyclopentenyl ether (3) | 397.27 | RD-UT-1137-172 | 27.0 g | 68.00 | 1.0 |
| Allyltributylstannane | 331.12 | 05013BJV | 135.1 g | 408.00 | 6.0 |
| Azobisisobutyronitrile (AIBN) | 164.21 | MKBJ4237V | 5.6 g | 34.00 | 0.5 |
| Toluene (anhydrous) | NA | SHBD4769V | 150 mL | NA | NA |
| Silica gel (230-400 mesh) | NA | 80107 | 975.9 g | NA | NA |

The reaction in Example 2 is described in the scheme below:

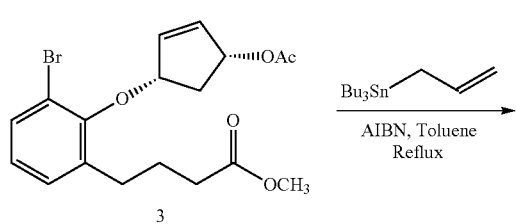

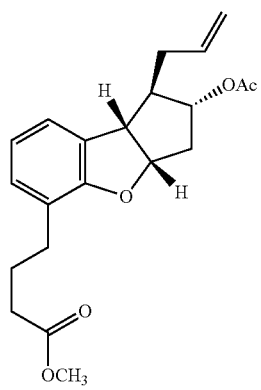

EXAMPLE 3

Synthesis of Alkenyl Acetoxycyclopentabenzofuran (5)

A 1000 mL, single necked, round bottom flask fitted with a condenser was charged with a solution of allyl acetoxycyclopentabenzofuran (4) (15.6 g, 43.52 mmol) in anhydrous toluene (500 mL). To this, carbonylchlorohydridotris(triphenylphosphine)ruthenium (II) (2.07 g, 2.17 mmol) was added and then the system was evacuated three times and replaced with argon. This was heated to reflux at 110° C. under argon. The progress of the reaction was monitored by UPLC every 20 mins for 1 hour, which showed 96% conversion and no progress beyond that point. After 1 h, the reaction was concentrated in vacuo to reduce the amount of toluene and then loaded directly onto the silica gel packed column for purification to yield alkenyl acetoxycyclopentabenzofuran (5) (14.5 g, 92.6%) (Lot #RD-UT-1137-178). Specifically, a filter-type column of diameter 11.5 cm and 18 cm in length packed with silica gel (580 g) was used for purification using ethyl acetate and hexanes. The polarity of the solvent was increased from 0 to 8%. The compound was characterized by $^1$H NMR and UPLC (ratio of product: starting material, 98.5: 1.5).

TABLE 3

| Material used in Example 3 | | | | | |
|---|---|---|---|---|---|
| Name | MW | Lot No. | Amount | mmol | Eq. |
| Allyl acetoxycyclopentabenzofuran (4) | 358.42 | RD-UT-1137-175-I | 15.6 g | 43.52 | 1.0 |
| Carbonylchlorohydridotris(triphenylphosphine)ruthenium(II) | 952.40 | RD-UT-1137-175-II | 2.07 g | 2.17 | 0.05 |
| Toluene (anhydrous) | NA | MKBP7702V | 500 mL | NA | NA |
| Silica gel (230-400 mesh) | NA | SHBD6439V | 580 g | NA | NA |

The reaction in Example 3 is described in the scheme below:

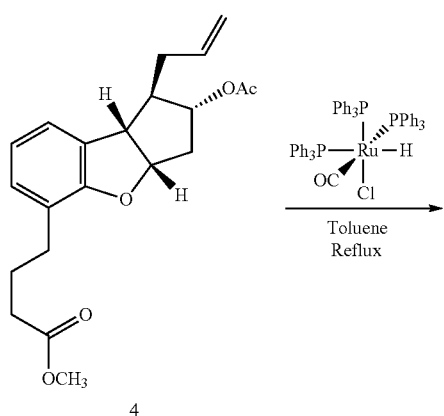

4

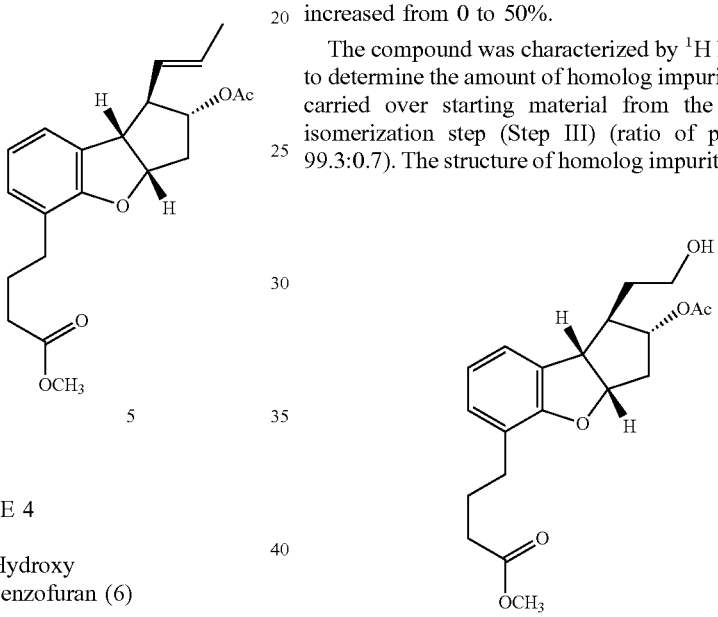

5

EXAMPLE 4

Synthesis of Hydroxy Acetoxycyclopentabenzofuran (6)

A 500 mL, three necked, round bottom flask fitted with an ozone bubbler, rubber septa was charged with a solution of alkenyl acetoxycyclopentabenzofuran (5) (14.2 g, 39.61 mmol) in anhydrous methanol (150 mL) and anhydrous dichloromethane (50 mL), and this was cooled to −78° C. Then ozone gas was bubbled through the solution for 2h. Specifically, a Wedeco GSO 10 series ozone generator was used as a source for ozone. The oxygen pressure was maintained at 0.5 psi with instrument running at power level of 81 W. Utmost care should be taken while bubbling the ozone through the reaction mixture. Excess ozone may generate side products in the reaction mixture. Progress of the reaction mixture should be monitored every 25 minutes. Time required for conversion may be higher of lager amounts.

The progress of the reaction was monitored by TLC, which indicated complete conversion of starting material. A small aliquot was quenched with dimethyl sulfide to convert ozonide to aldehyde for in process analysis using 60% ethyl acetate:hexane as mobile phase for TLC. At this stage, the temperature of the reaction mixture was increased to −20° C. and flushed with argon gas for 5 minutes.

To this solution (ozonide intermediate), sodium borohydride (2.99 g, 79.23 mmol) was added at −20° C. and stirred under argon for 0.5 h while allowing the reaction mixture to attain ambient temperature. The progress of the reaction was monitored by TLC. Specifically, a 80% ethyl acetate:hexane mobile phase was used for elution. After completion of the reaction, it was quenched with a saturated solution of ammonium chloride (30 mL) and organic volatiles were evaporated in vacuo. The residue was partitioned between ethyl acetate (200 mL) and water (200 mL). The organic layer was separated and aqueous layer was extracted with ethyl acetate (2×150 mL). The combined organic layers were washed with brine (150 mL), dried over sodium sulfate and evaporated in vacuo to obtain crude product. This was loaded on to the silica gel packed column for purification to obtain hydroxy acetoxycyclopentabenzofuran (6) (11.8 g, 85.5%) (Lot #RD-UT-1137-180). Specifically, a filter-type column of diameter 11.5 cm and 18 cm in length packed with silica gel (622 g) was used for purification using ethyl acetate and hexanes. The polarity of the solvent was increased from 0 to 50%.

The compound was characterized by $^1$H NMR and HPLC to determine the amount of homolog impurity formed due to carried over starting material from the previous olefin isomerization step (Step III) (ratio of product:homolog, 99.3:0.7). The structure of homolog impurity is given below.

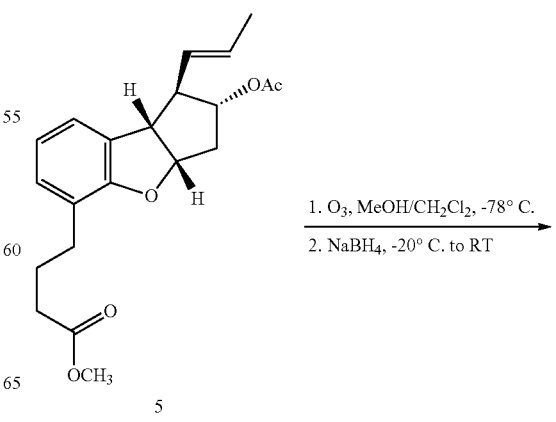

Acetate Homolog Impurity

The reaction in Example 4 is described in the scheme below:

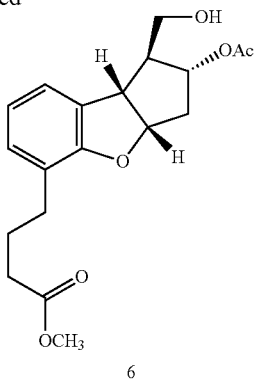

6

TABLE 4

Material used in Example 4

| Name | MW | Lot No. | Amount | mmol | Eq. |
|---|---|---|---|---|---|
| Alkenyl acetoxycyclo-pentabenzofuran (5) | 358.42 | RD-UT-1137-178 | 14.2 g | 39.61 | 1.0 |
| Methanol (anhydrous) | NA | T-08-0195 | 150 mL | NA | NA |
| Dichloromethane (anhydrous) | NA | SHBF0333V | 50 mL | NA | NA |
| Sodium borohydride | 37.83 | 0000023281 | 2.99 g | 79.23 | 2.0 |
| Silica gel (230-400 mesh) | NA | 80107 | 622 g | NA | NA |

EXAMPLE 5

Synthesis of Beraprost Diol (7)

A 500 mL, single necked, round bottom flask was charged with a solution of hydroxy acetoxycyclopentabenzofuran (6) (10.7 g, 30.71 mmol) in anhydrous methanol (150 mL). Then a solution of conc. $H_2SO_4$ (0.1 mL) in 50 mL methanol was added and stirred overnight (14 h).

Reaction rate was found to be slow based on TLC. A 5% methanol:DCM mobile phase was used for TLC elution. At this stage additional amount of conc. $H_2SO_4$ (0.27 mL in 10 mL methanol solution) was charged four times at different intervals (14 h, 21 h, 38 h, 62 h) until completion of the reaction. Reaction was found to be complete after 68 h (total conc. $H_2SO_4$ used is 1.18 mL).

At this point, the reaction mixture was cooled to 0° C. and a solution of saturated sodium bicarbonate (25 mL) was added over a period of 5 minutes until pH reached 8. This mixture was evaporated in vacuo to remove organic volatiles and the residue was partitioned between ethyl acetate (150 mL) and water (150 mL). The organic layer was separated and aqueous layer was extracted with ethyl acetate (2×100 mL). The combined organic layers were washed with brine, dried over sodium sulfate and evaporated in vacuo to obtain crude product (9.3 g). Crude product was crystallized from MTBE to obtain beraprost diol (7) (7.5 g, 80% isolated yield) (Lot #RD-UT-1137-182-0). Specifically, crude product was dissolved in 45 mL (5 volumes) MTBE by heating to reflux temperature and slowly cooled to RT. At approx. 30° C., 90 mg of pure seed (beraprost diol, Lot #13-13206-01) was added and stirred at room temperature for 2 h, which yielded thick off-white solid. This was cooled to 10° C. and stirred for 15 minutes and filtered through filter paper (No. 4) while using 5% MTBE:Hexane (50 mL) for washing. The off-white solid material was air dried until constant weight was obtained. This was characterized by $^1H$ NMR, $^{13}C$ NMR, MS, optical rotation, chiral HPLC and melting point. See summary of analytical data table for values.

The reaction in Example 5 is described in the scheme below:

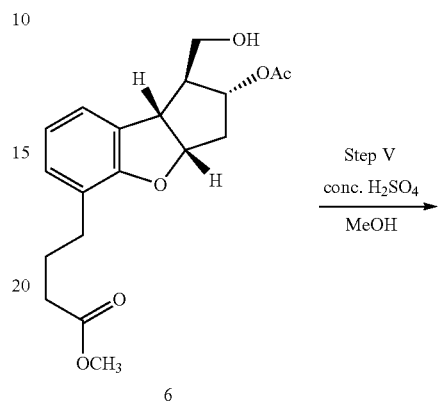

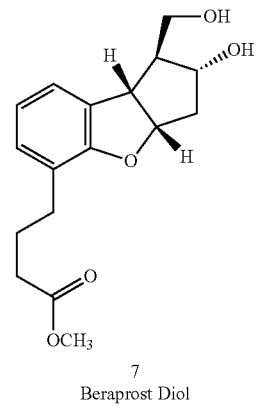

7
Beraprost Diol

TABLE 5

Material used in Example 5

| Name | MW | Lot No. | Amount | mmol | Eq. |
|---|---|---|---|---|---|
| Hydroxy acetoxycyclo-pentabenzofuran (6) | 348.40 | RD-UT-1137-180 | 10.7 g | 30.71 | 1.0 |
| Concentrated sulfuric acid | NA | T-07-0373 | 1.18 mL | NA | NA |
| Methanol (anhydrous) | NA | T-08-0195 | 240 mL | NA | NA |

A summary of Analytical Data on single isomer of Beraprost Diol is shown in the table below.

TABLE 6

Summary of Analytical Data on Single Isomer of Beraprost Diol

| S. No. | Description | Results |
|---|---|---|
| 1. | Structure | (see structure) |
| 2. | Chemical Name | methyl 4-((1S,2R,3aS,8bS)-2-hydroxy-1-(hydroxymethyl)-2,3,3a,8b-tetrahydro-1H-cyclopenta[b]benzofuran-5-yl)butanoate (or) 1H-Cyclopenta[b]benzofuran-5-butanoic acid, 2,3,3a,8b-tetrahydro-2-hydroxy-1-(hydroxymethyl)-, methyl ester, (1S,2R,3aS,8bS)- |
| 3. | CAS Number | 132203-90-8 |
| 4. | Lot Number | RD-UT-1137-182-CI |
| 5. | Molecular Formula | $C_{17}H_{22}O_5$ |
| 6. | Molecular Weight | 306.35 |
| 7. | MS | Practical Value: $[M + Na]^+$ = 329.51<br>Calculated Value: $[M + Na]^+$ = 329.35 |
| 8. | Melting Point | 64.5 to 66.3° C. |
| 9. | Optical Rotation | $[\alpha]_D$ = +25.6 at 25° C. (c 1.000, EtOH)<br>Ref: $[\alpha]_D$ = +25.6 at 24.9° C. (c 1.000, EtOH) |
| 10. | $^1$H NMR | Conforms to the structure |
| 11. | $^{13}$C NMR | Conforms to the structure |
| 12. | Purity by Chiral HPLC | 99.90% |

EXAMPLE 6

Synthesis of Beraprost Based on Scheme 4

Beraprost is synthesized according to the method shown in Scheme 4. In particular, the synthesis has the following steps: 1) tritylation of compound 1 having a tricyclic core and side chain for coupling to form compound 2; 2) TBDMS protection to form compound 3; 3) detritylation to form compound 4; 4) oxidation to form compound 5; 5) coupling with tributyl tin to form compound 6; 6) reaction with Weinreb amide to form compound 7; 7) reduction and deprotection to form Beraprost. The reaction conditions for each step is well known in the art, such as described in Das et al., Chem. Rev. (2007), 107:3286-3337.

EXAMPLE 7

Synthesis of Beraprost based on Scheme 5

Beraprost is synthesized according to the method shown in Scheme 4, including a Grubbs II metathesis step and base hydrolysis step. In particular, ruthenium metal catalyst is used for Grubb's metathesis reaction. It involves the use of Grubb's II (the second generation ruthenium catalyst) in solvents, e.g. dichloromethane, methyl tertiary butyl methylether, pentane, hexane, methanol, isopropyl alcohol, tetrahydrofuran, and acetone. The reaction conditions for each step is well known in the art, such as described in Das et al., Chem. Rev. (2007), 107:3286-3337.

What is claimed is:

1. A process for preparing a compound of the following formula:

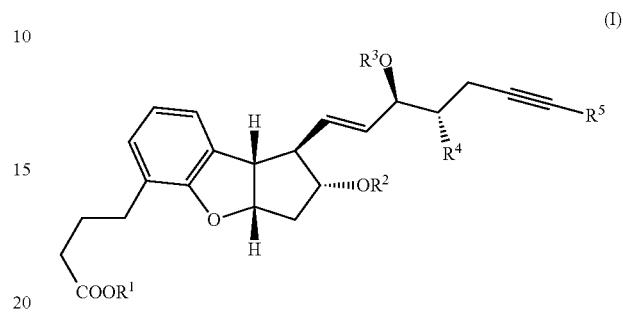

(I)

wherein $R^1$ represents a cation, H, or $C_{1-12}$ alkyl,
$R^2$ and $R^3$ each represent H or a hydroxy protective group,
$R^4$ represents H or $C_{1-3}$ alkyl, and
$R^5$ represents H or $C_{1-6}$ alkyl, comprising:
(1) reacting a compound of the following formula:

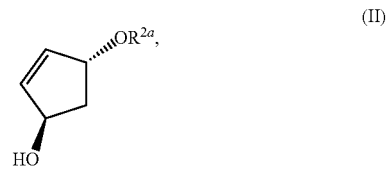

(II)

wherein $R^{2a}$ is H or an hydroxy protective group,
with a compound of the following formula:

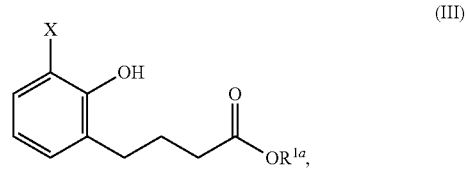

(III)

wherein $R^{1a}$ is a cation, H, or $C_{1-2}$ alkyl, X is a halogen selected from chloro, bromo and iodo,
to form a compound of the following formula:

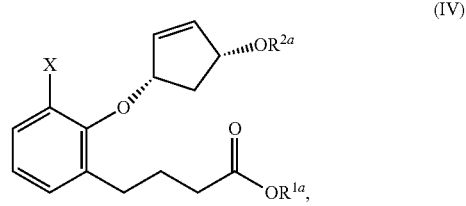

(IV)

wherein $R^{1a}$, $R^{2a}$ and X are each defined above;
(2) cyclizing a compound of formula (IV) to form a compound of the following formula:

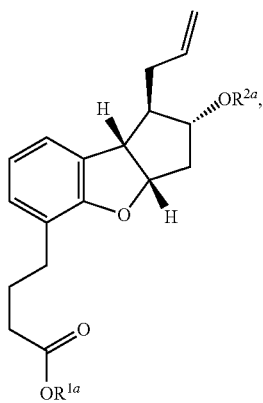
(V)

wherein $R^{1a}$ and $R^{2a}$ are each defined above;

(3) isomerizing an allyl of the compound of formula (V) to form a propenyl resulting in a compound of the following formula:

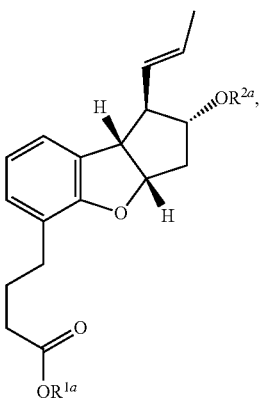
(VI)

wherein $R^{1a}$ and $R^{2a}$ are each defined above;

(4) ozonolysis and in situ reduction to convert the propenyl of the compound of formula (VI) to form an alcohol resulting in a compound of the following formula:

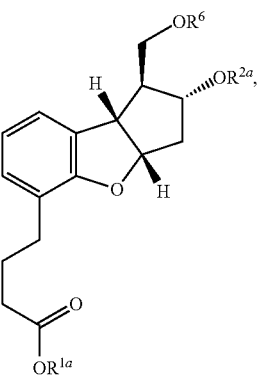
(VII)

wherein $R^{1a}$ and $R^{2a}$ are each defined above, $R^6$ is H or a hydroxy protective group;

(5) deprotecting an acetate of the compound of formula (VII) to form a compound of the following formula:

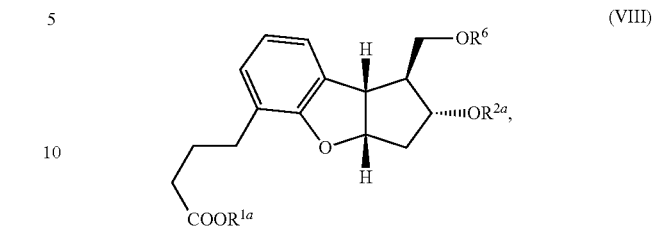
(VIII)

wherein $R^{1a}$, $R^{2a}$ and $R^6$ are each defined above;

(6) selectively deprotecting the primary hydroxy protective group, followed by oxidation of the primary hydroxy group to form an aldehyde, followed by coupling with a side-chain of the formula:

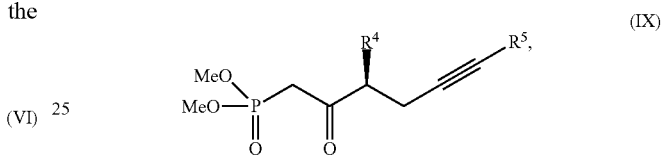
(IX)

wherein $R^4$ and $R^5$ are each defined above to form a compound of the following formula:

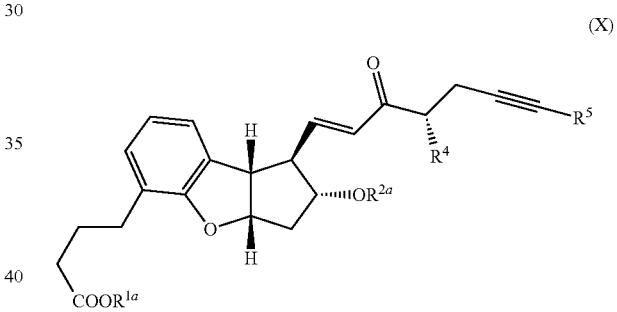
(X)

(7) reduction of the ketone, deprotection of any remaining hydroxy protective group and optionally converting the $R^{1a}$ into a cation or H to form a compound of the following formula:

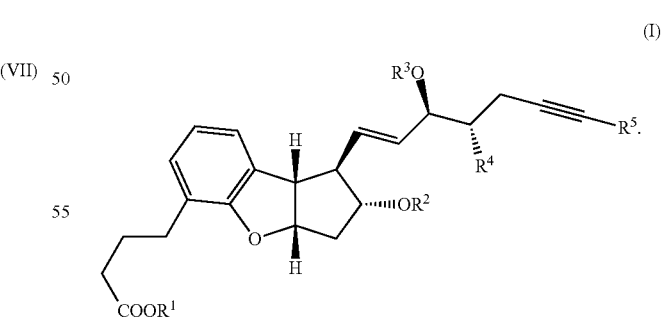
(I)

2. The process of claim 1, wherein the compound of formula (I) is produced as a substantially pure single isomer.

3. The process of claim 1, wherein $R^2$, $R^3$, $R^{2a}$ and $R^6$ each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl.

4. The process of claim 1, wherein $R^{1a}$ is $CH_3$ and $R^{2a}$ and $R^6$ are both H.

5. The process of claim 1, wherein azobisisobutyronitrile is used as a radical initiator in step (2).

6. The process of claim 1, wherein a catalytic amount of carbonylchlorohydridotris(triphenylphosphine) ruthenium (II) is used in step (3).

7. The process of claim 1, wherein step (4) produces an in situ trapped aldehyde intermediate represented by the compound of formula (XI)

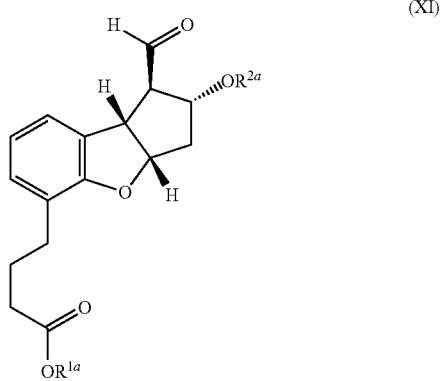

(XI)

wherein $R^{1a}$ and $R^{2a}$ is each defined above.

8. The process of claim 1, wherein sulfuric acid is used in step (5).

9. A process for preparing a compound of the following formula:

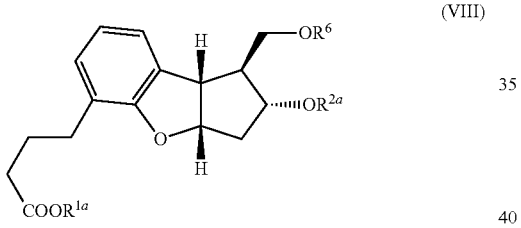

(VIII)

wherein $R^{1a}$ represents a cation, H, or $C_1$-$_{12}$ alkyl and $R^{2a}$ and $R^6$ each represent H, an acetate or a hydroxy protective group, comprising:

(1) performing a Mitsunobu reaction on the compound of the following formula:

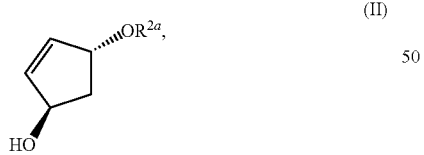

(II)

wherein $R^{2a}$ is defined above,
with a compound of the following formula:

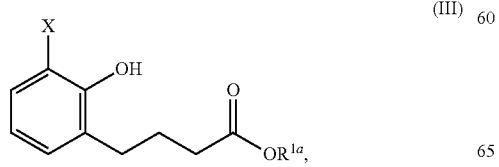

(III)

wherein $R^{1a}$ is defined above, X is a halogen selected from chloro, bromo and iodo,
to form a compound of the following formula:

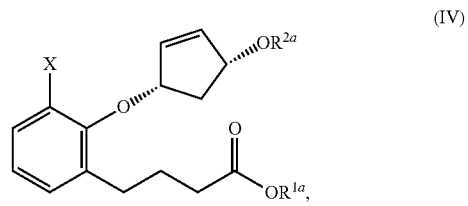

(IV)

wherein $R^{1a}$, $R^{2a}$ and X is each defined above;

(2) radical cyclization of formula (IV) to form a compound of the following formula:

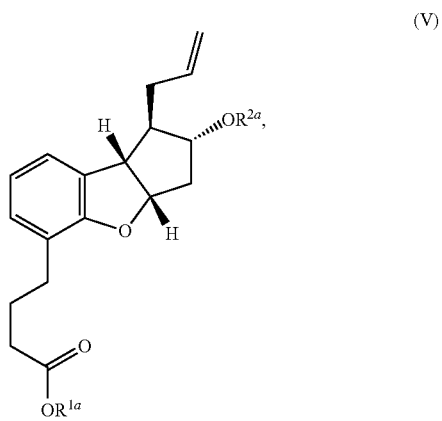

(V)

wherein $R^{1a}$ and $R^{2a}$ is each defined above;

(3) isomerizing the allyl of the compound of formula (V) to form a propenyl resulting in a compound of the following formula:

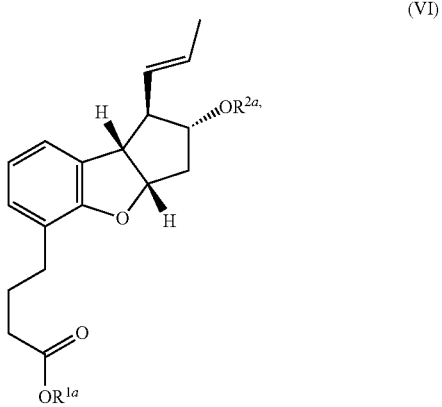

(VI)

wherein $R^{1a}$ and $R^{2a}$ is each defined above;

(4) ozonolysis and in situ reduction to convert the propenyl of the compound of formula (VI) to form an alcohol resulting in a compound of the following formula:

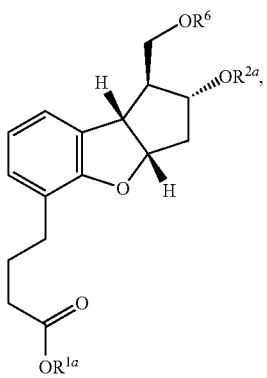

(VII)

wherein $R^{1a}$, $R^{2a}$ and $R^6$ are each defined above;

(5) deprotection of the acetate of the compound of formula (VII) to form a compound of the following formula:

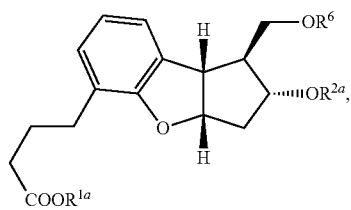

(VIII)

wherein $R^{1a}$, $R^{2a}$ and $R^6$ is each defined above.

10. The process of claim 9, wherein the compound of formula (VIII) is produced as a substantially pure single isomer.

11. The process of claim 9, wherein $R^{2a}$ and $R^6$ each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl.

12. The process of claim 9, wherein $R^{1a}$ is $CH_3$, and $R^{2a}$ and $R^6$ are both H.

13. The process of claim 9, wherein azobisisobutyronitrile is used in step (2) as a radical initiator.

14. The process of claim 9, wherein a catalytic amount of carbonylchlorohydridotris(triphenylphosphine) ruthenium (II) is used in step (3).

15. The process of claim 9, wherein sulfuric acid is used in step (5).

16. A process for preparing a compound of the following formula:

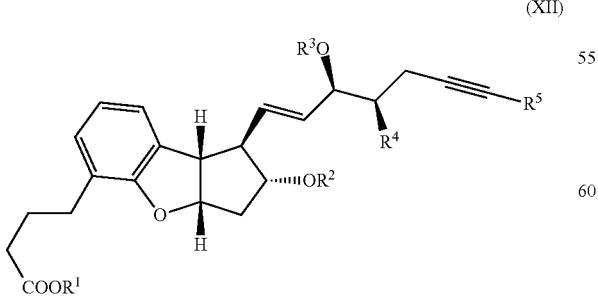

(XII)

wherein $R^1$ represents a cation, H, or $C_{1-12}$ alkyl,
$R^2$ and $R^3$ each represent H or a hydroxy protective group, $R^4$ represents H or $C_{1-3}$ alkyl, and
$R^5$ represents H or $C_{1-6}$ alkyl, comprising:

(1) reacting a compound of the following formula:

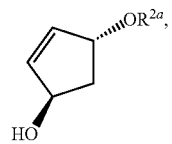

(II)

wherein $R^{2a}$ is H or an hydroxy protective group,
with a compound of the following formula:

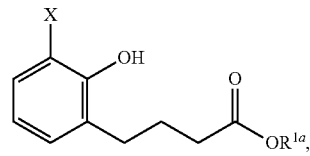

(III)

wherein $R^{1a}$ is a cation, H, or $C_{1-12}$ alkyl, X is a halogen selected from chloro, bromo and iodo,
to form a compound of the following formula:

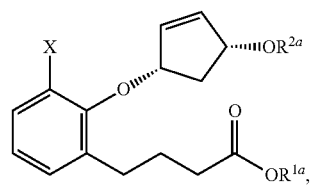

(IV)

wherein $R^{1a}$, $R^{2a}$ and X are each defined above;

(2) cyclizing a compound of formula (IV) to form a compound of the following formula:

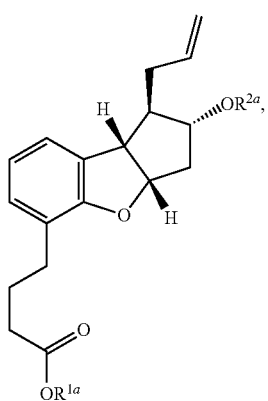

(V)

wherein $R^{1a}$ and $R^{2a}$ are each defined above;

(3) isomerizing an allyl of the compound of formula (V) to form a propenyl resulting in a compound of the following formula:

(VI)

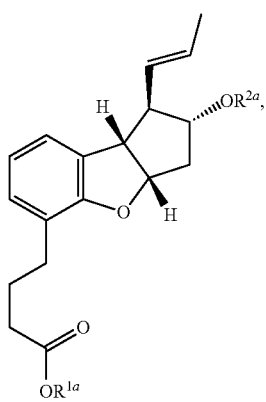

wherein R¹ᵃ and R²ᵃ are each defined above;

(4) ozonolysis and in situ reduction to convert the propenyl of the compound of formula (VI) to form an alcohol resulting in a compound of the following formula:

(VII)

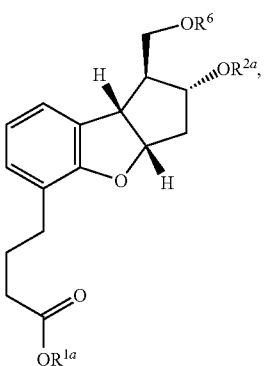

wherein R¹ᵃ and R²ᵃ are each defined above, R⁶ is H or a hydroxy protective group;

(5) deprotecting an acetate of the compound of formula (VII) to form a compound of the following formula:

(VIII)

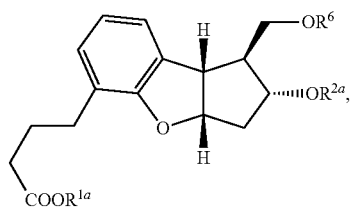

wherein R¹ᵃ, R²ᵃ and R⁶ are each defined above;

(6) selectively deprotecting the primary hydroxy protective group, followed by oxidation of the primary hydroxy group to form an aldehyde, followed by coupling with a side-chain of the formula:

(XIII)

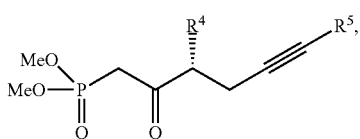

wherein $R^4$ and $R^5$ are each defined above to form a compound of the following formula:

(XIV)

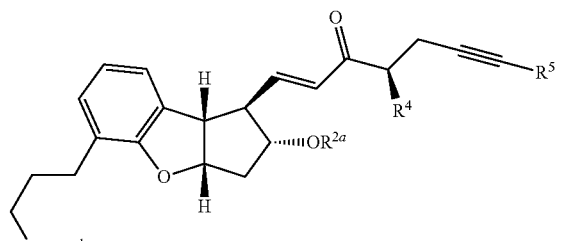

(7) reduction of the ketone, deprotection of any remaining hydroxy protective group and optionally converting the $R^{1a}$ into a cation or H to form a compound of the following formula:

(XII)

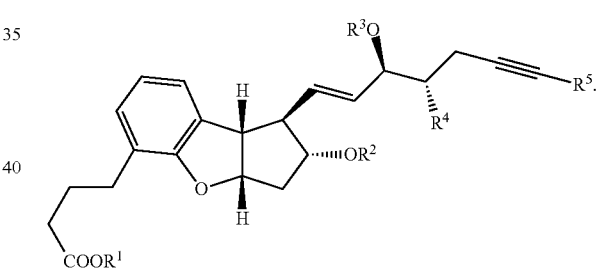

17. The process of claim 16, wherein the compound of formula (XII) is produced as a substantially pure single isomer.

18. The process of claim 16, wherein $R^2$, $R^3$, $R^{2a}$ and $R^6$ each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl.

19. The process of claim 16, wherein $R^{1a}$ is $CH_3$ and $R^{2a}$ and $R^6$ are both H.

20. The process of claim 16, wherein azobisisobutyronitrile is used as a radical initiator in step (2).

21. The process of claim 16, wherein a catalytic amount of carbonylchlorohydridotris(triphenylphosphine) ruthenium (II) is used in step (3).

22. The process of claim 16, wherein sulfuric acid is used in step (5).

23. A process for preparing a compound of the following formula:

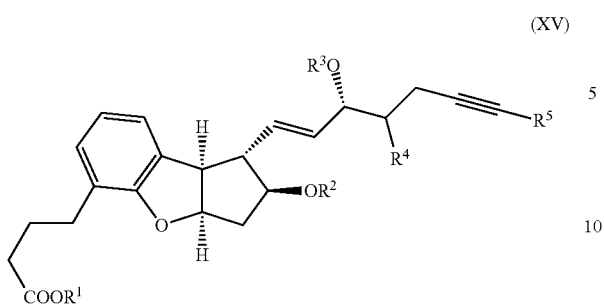
(XV)

wherein $R^1$ represents a cation, H, or $C_{1-12}$ alkyl,
$R^2$ and $R^3$ each represent H or a hydroxy protective group,
$R^4$ represents H or $C_{1-3}$ alkyl, and
$R^5$ represents H or $C_{1-6}$ alkyl, comprising:
(1) reacting a compound of the following formula:

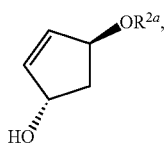
(XVI)

wherein $R^{2a}$ is H or an hydroxy protective group,
with a compound of the following formula:

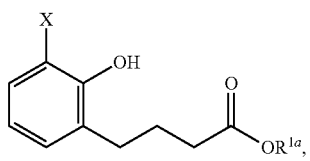
(III)

wherein $R^{1a}$ is a cation, H, or $C_{1-12}$ alkyl, X is a halogen selected from chloro, bromo and iodo,
to form a compound of the following formula:

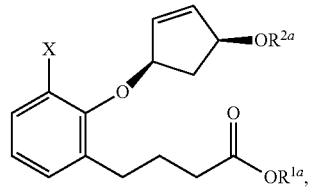
(XVII)

wherein $R^{1a}$, $R^{2a}$ and X are each defined above;
(2) cyclizing a compound of formula (XVII) to form a compound of the following formula:

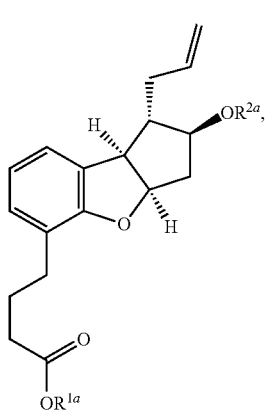
(XVIII)

wherein $R^{1a}$ and $R^{2a}$ are each defined above;
(3) isomerizing an allyl of the compound of formula (XVIII) to form a propenyl resulting in a compound of the following formula:

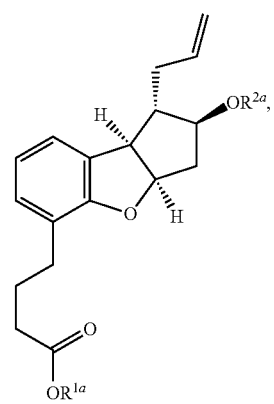
(XIX)

wherein $R^{1a}$ and $R^{2a}$ are each defined above;
(4) ozonolysis and in situ reduction to convert the propenyl of the compound of formula (XIX) to form an alcohol resulting in a compound of the following formula:

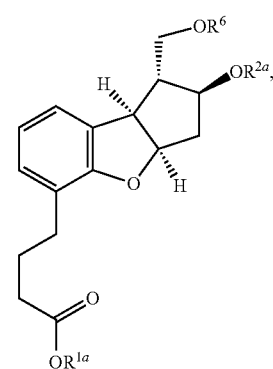
(XX)

wherein $R^{1a}$ and $R^{2a}$ are each defined above, $R^6$ is H or a hydroxy protective group;

(5) deprotecting an acetate of the compound of formula (XX) to form a compound of the following formula:

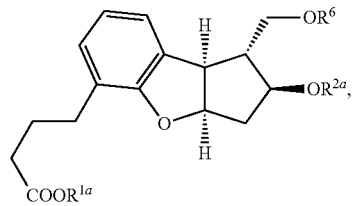
(XXI)

wherein $R^{1a}$, $R^{2a}$ and $R^6$ are each defined above;

(6) selectively deprotecting the primary hydroxy protective group, followed by oxidation of the primary hydroxy group to form an aldehyde, followed by coupling with a side-chain of the formula:

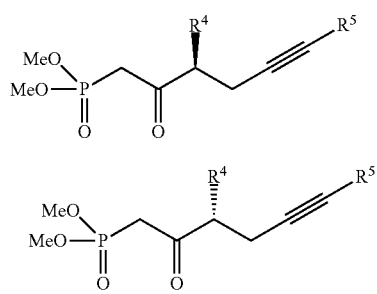
(IX)

or (XXII)

wherein $R^4$ and $R^5$ are each defined above to form a compound of the following formula:

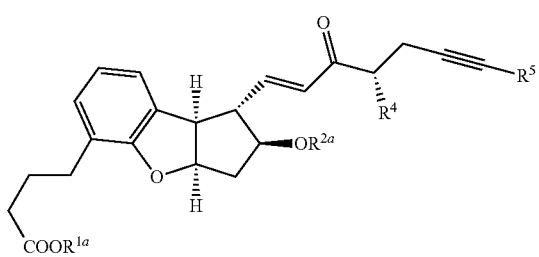
(XXIII)

or (XXIV)

(7) reduction of the ketone, deprotection of any remaining hydroxy protective group and optionally converting the $R^{1a}$ into a cation or H to form a compound of the following formula:

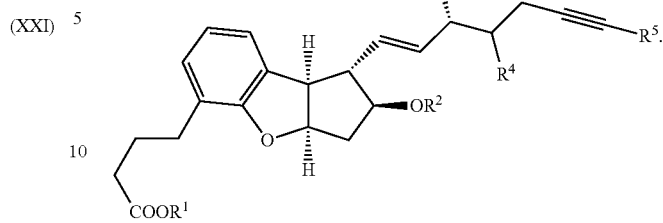
(XV)

24. The process of claim 23, wherein the compound of formula (XV) is produced as a substantially pure single isomer of the formula

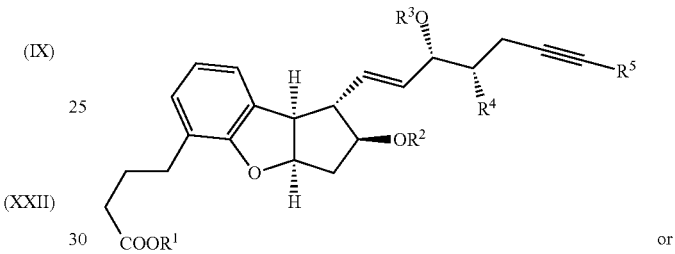
(XXV)

or

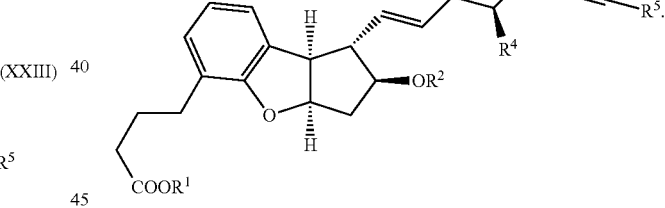
(XXVI)

25. The process of claim 16, wherein $R^2$, $R^3$, $R^{2a}$ and $R^6$ each independently represent acetate, trimethylsilyl, triethylsilyl, t-butyldimethylsilyl, t-butyldiphenylsilyl, phenyldimethylsilyl, tetrahydropyranyl, benzoate ester, benzyl, or substituted benzyl.

26. The process of claim 23, wherein $R^{1a}$ is $CH_3$ and $R^{2a}$ and $R^6$ are both H.

27. The process of claim 23, wherein azobisisobutyronitrile is used as a radical initiator in step (2).

28. The process of claim 23, wherein a catalytic amount of carbonylchlorohydridotris(triphenylphosphine) ruthenium (II) is used in step (3).

29. The process of claim 23, wherein sulfuric acid is used in step (5).

30. A process for preparing a compound of the following formula:

(I)

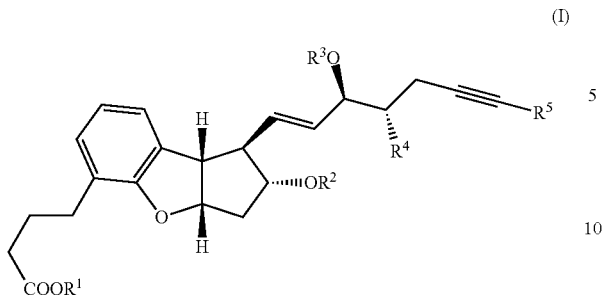

wherein R¹ represents a cation, H, or $C_{1-12}$ alkyl,
R² and R³ each represent H or a hydroxy protective group,
R⁴ represents H or $C_{1-3}$ alkyl, and
R⁵ represents H or $C_{1-6}$ alkyl, comprising:

(1) protecting a hydroxyl group of a compound of the following formula:

(VII)

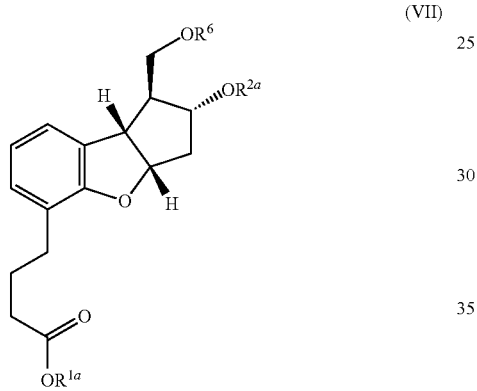

wherein $R^{1a}$ is a cation, H, or $C_{1-12}$ alkyl; $R^{2a}$ and R⁶ are each H or a hydroxy protective group, to produce a compound of the following formula:

(XXVII)

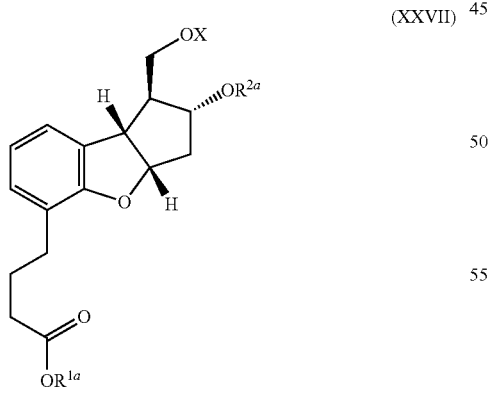

wherein X is a trityl protecting group, tertiary butyldimethyl silyl (TBDMS), triethyl silyl (TES), methoxy methane (MOM), tertiary butyldiphenyl silyl (TBDPS), acetate, benzoate, or benzyl;

(2) protecting a hydroxyl group of the compound of (XXVII) to form a compound of the following formula:

(XXVIII)

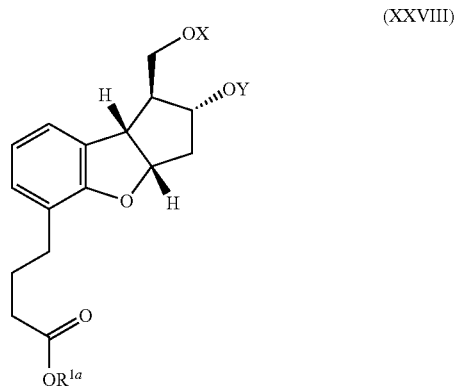

wherein Y is tertiary butyldimethyl silyl (TBDMS), triethyl silyl (TES), methoxy methane (MOM), tertiary butyldiphenyl silyl (TBDPS), acetate, benzoate, or benzyl;

(3) deprotecting one of the hydroxyl protective groups to form a compound of the following formula:

(XXIX)

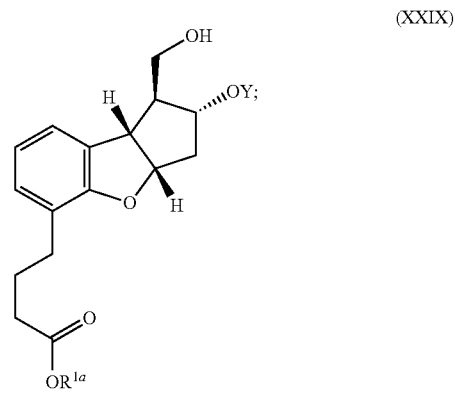

(4) oxidation of a hydroxyl group of the compound to form a compound of the following formula:

(XXX)

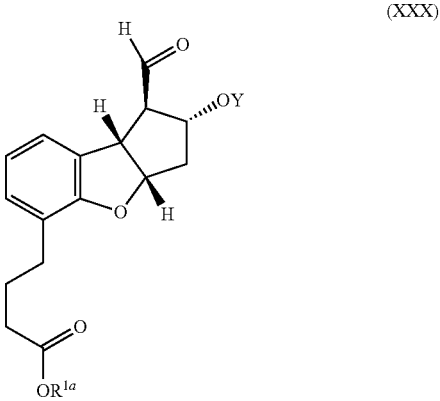

(5) Reacting with stannanes to form a compound of the following formula:

(XXXI)

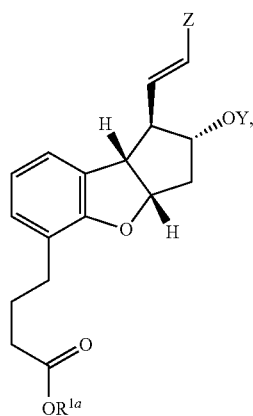

wherein Z is SnBu3;
(6) coupling with a compound of the following formula:

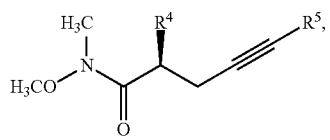
(XXXII)

to form a compound of the following formula:

(XXXIII)

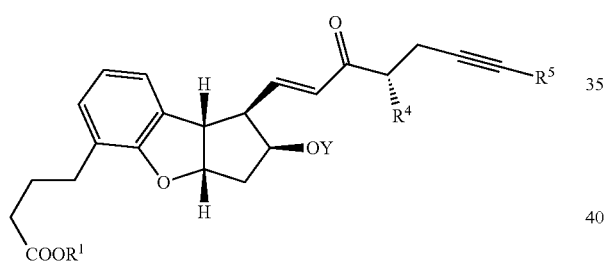

wherein $R^1$, $R^2$, $R^4$ and $R^5$ are each defined above,
(7) deprotecting the protective group Y and reducing the ketone of the compound of the formula (XXXIII) to form a compound of the following formula:

(I)

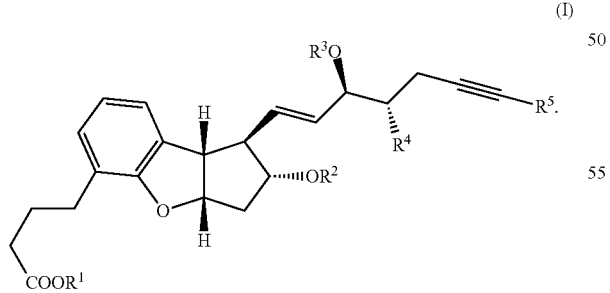

31. The process of claim 30, wherein the compound of formula (I) is produced as a substantially pure single isomer.

32. A process for preparing a compound of the following formula:

(I)

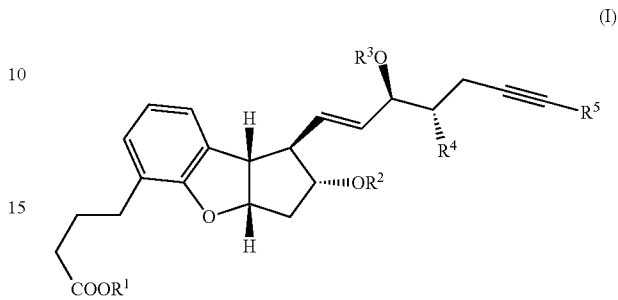

wherein $R^1$ represents a cation, H, or $C_{1-12}$ alkyl,
$R^2$ and $R^3$ each represent H or a hydroxy protective group,
$R^4$ represents H or $C_{1-3}$ alkyl, and
$R^5$ represents H or $C_{1-6}$ alkyl, comprising:
(1) reacting a compound of the following formula:

(XXXIV)

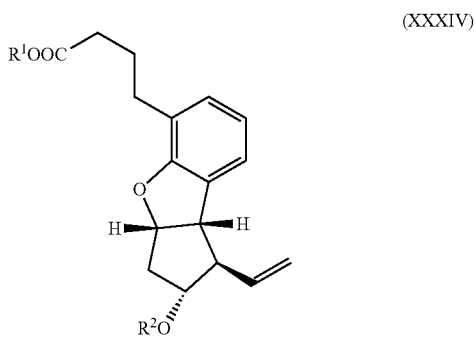

with a compound of the following formula:

(XXXV)

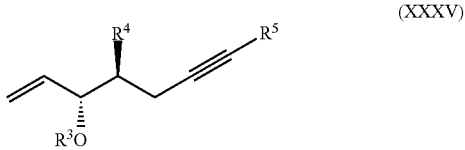

in a Grubbs II metathesis reaction, and
(2) base hydrolysis to produce the compound of formula (I).

33. The process of claim 32, wherein the compound of formula (I) is produced as a substantially pure single isomer.

* * * * *